US010190126B2

(12) United States Patent
Maor et al.

(10) Patent No.: US 10,190,126 B2
(45) Date of Patent: Jan. 29, 2019

(54) TRANSGENIC PLANTS WITH MODIFIED SUGAR CONTENT AND METHODS OF GENERATING SAME

(71) Applicant: A. B. Seeds Ltd., Lod (IL)

(72) Inventors: Rudy Maor, Rechovot (IL); Iris Nesher, Tel-Aviv (IL)

(73) Assignee: A.B. Seeds Ltd. (IL)

( * ) Notice: Subject to any disclaimer, the term of this patent is extended or adjusted under 35 U.S.C. 154(b) by 0 days.

(21) Appl. No.: 14/438,763

(22) PCT Filed: Oct. 28, 2013

(86) PCT No.: PCT/IL2013/050880
§ 371 (c)(1),
(2) Date: Apr. 27, 2015

(87) PCT Pub. No.: WO2014/064704
PCT Pub. Date: May 1, 2014

(65) Prior Publication Data
US 2015/0299717 A1 Oct. 22, 2015

Related U.S. Application Data

(60) Provisional application No. 61/719,415, filed on Oct. 28, 2012.

(51) Int. Cl.
C12N 15/113 (2010.01)
C12N 15/63 (2006.01)
C12N 15/82 (2006.01)

(52) U.S. Cl.
CPC ........ C12N 15/8218 (2013.01); C12N 15/113 (2013.01); C12N 15/8245 (2013.01); C12N 15/8274 (2013.01); C12N 15/8275 (2013.01); C12N 15/8277 (2013.01); C12N 15/8278 (2013.01); C12N 2310/141 (2013.01)

(58) Field of Classification Search
None
See application file for complete search history.

(56) References Cited

U.S. PATENT DOCUMENTS

| 5,811,636 A | 9/1998 | Hanna et al. |
| 6,124,528 A | 9/2000 | Shewmaker et al. |
| 2006/0130176 A1* | 6/2006 | Reyes-Taboada ............ C12N 15/8216 800/279 |
| 2007/0214521 A1* | 9/2007 | Zhu ...................... C07K 14/415 800/289 |
| 2009/0100537 A1 | 4/2009 | Concibido et al. |
| 2009/0293148 A1 | 11/2009 | Ren et al. |
| 2011/0296556 A1 | 12/2011 | Sammons et al. |
| 2011/0314574 A1 | 12/2011 | Messing et al. |
| 2012/0272408 A1 | 10/2012 | Maor et al. |
| 2015/0299724 A1 | 10/2015 | Gill et al. |

FOREIGN PATENT DOCUMENTS

WO   WO 2014/064705 A2   5/2014

OTHER PUBLICATIONS

Zhang et al 2011 Biotechnol let 33:403-409.*
Julander 1945 Plant Physiology 573-599.*
Clough et al., "Floral dip: a simplified method for Agrobacterium-mediated transformation of Arabidopsis thaliana," The Plant Journal, 16(6):735-743 (1998).
Conkling et al., "Isolation of Transcriptionally Regulated Root-Specific Genes from Tobacco," Plant Physiol., 93:1203-1211 (1990).
Cortina, et al., "Tomato transformation and transgenic plant production," Plant Cell, Tissue and Organ Culture, 76:269-275 (2004).
Desfeux et al., "Female Reproductive Tissues Are the Primary Target of Agrobacterium-Mediated Transformation by the Arabidopsis Floral-Dip Method," Plant Physiol.,123:895-904 (2000).
Egli, et al., "Moisture Stress and N Redistribution in Soybean," Agron. J., 75:1027-1031 (1983).
Franco-Zorilla et al., "Target mimicry provides a new mechanism for regulation of microRNA activity," Nature Genetics, 39(8):1033-1037 (2007).
Friedman, et al., "Nutritional and Health Benefits of Soy Proteins," J. Agric. Food Chem, 49(3):1069-1086 (2001).
Han et al., "Molecular Basis for the Recognition of Primary microRNAs by the Drosha-DGCR8 Complex," Cell, 125:887-901 (2006).
International Preliminary Report on Patentability Chapter I dated May 1, 2014, in International Application No. PCT/IL2013/050880.
International Preliminary Report on Patentability Chapter I dated Jul. 8, 2014, in International Application No. PCT/IL2013/050882.
International Search Report dated May 1, 2014, in International Patent Application No. PCT/IL2013/050880.
International Search Report dated Jul. 8, 2014, in International Patent Application No. PCT/IL2013/050882.
Jiang et al., "Osmotic Adjustment and Root Growth Associated with Drought Preconditioning-Enhanced Heat Tolerance in Kentucky Bluegrass," Crop Sci., 41:1168-1173 (2001).
Jones-Rhodes et al., "MircoRNAs and Their Regulatory Roles in Plants," Annual Review of Plant Biology, 57:19-53 (2006).
Kantar et al., "miRNA expression patterns of Triticum dicoccoides in response to shock drought stress," Planta 233:471-484 (2011).

(Continued)

Primary Examiner — Brent T Page
(74) Attorney, Agent, or Firm — Amanda Carmany-Rampey; David Marsh; Arnold & Porter Kaye Scholer LLP

(57) ABSTRACT

This application provides and discloses small RNAs and their target genes that are involved in controlling the levels of sucrose, glucose, and fructose and methods of modulating expression or activity of these mi RNAs and target genes. This application further provides transgenic plants, plant parts, e.g., seeds, that have altered expression of these mi RNAs and target genes and have increased levels of sucrose, increased sucrose to glucose ratios, increased sucrose to hexose ratios, altered carbohydrate levels, or increased Brix in fruit from transgenic plants. This application also provides methods of producing and growing transgenic plants or seeds that have increased levels of sucrose, increased sucrose to glucose ratios, increased sucrose to hexose ratios, altered carbohydrate levels, or increased Brix in fruit from transgenic plants.

8 Claims, 4 Drawing Sheets
Specification includes a Sequence Listing.

(56) References Cited

OTHER PUBLICATIONS

Lam et al., "Site-specific mutations alter in vitro factor binding and change promoter expression pattern in transgenic plants," *Proc. Natl. Acad. Sci USA*, 86:7890-7894 (1989).
Liu et al., "Stomatal control and water use efficiency of soybean (*Glycine max* L. Merr.) during progressive soil drying," *Environmental and Experimental Botany*, 54:33-40 (2005).
Lopez-Bucio et al., "The role of nutrient availability in regulating root architecture," *Current Opinion in Plant Biology*, 6:280-287 ( 2003).
Manavalan et al., "Physiological and Molecular Approaches to Improve Drought Resistance in Soybean," *Plant Cell Physiol.*, 50(7):1260-1276 (2009).
Miron et al., "Sucrose Phosphate Synthase, Sucrose Synthase, and Invertase Activities in Developing Fruit of *Lycopersicon esculentum* Mill. and the Sucrose Accumulating *Lycopersicon hirsutum* Humb. and Bonpl.," *Plant Physiol.*, 95:623-7 (1991).
Morgan et al., "Water Use, Grain Yield, and Osmoregulation in Wheat," *Australian Journal of Plant Physiology.*, 13(4):523-532 (1986).
Purcell et al., "Drought and nitrogen source effects on nitrogen nutrition, seed growth, and yield in soybean," *Journal of Plant Nutrition*, 19:969-993 (1996).
Rosenfeld et al., "MicroRNAs accurately identify cancer tissue origin," *Nature Biotechnology*, 26(4):462-469 (2008).
Samac et al., "Effect of chitinase antisense RNA expression on disease susceptibility of *Arabidopsis* plants," *Plant Molecular. Biology*, 25:587-596 (1994).
Stevens, "Inheritance of Tomato Fruit Quality Components," *Plant Breeding Reviews*, 4:273-311 (2006).
Thompson, et al., "CLUSTAL W: improving the sensitivity of progressive multiple sequence alignment through sequence weighting, position-specific gap penalties and weight matrix choice," *Nucleic Acids Research*, 22(22):4673-4680 (1994).
Wang et al., "Plant responses to drought, salinity and extreme temperatures: towards genetic engineering for stress tolerance," *Planta*, 218:1-14 (2003).
Written Opinion of the International Search Authority dated May 1, 2014, in International Patent Application No. PCT/IL2013/050880.
Written Opinion of the International Search Authority dated Jul. 8, 2014, in International Patent Application No. PCT/IL2013/050882.
Braun et al., Understanding and manipulating sucrose phloem loading, unloading, metabolism, and signaling to enhance crop yield and food security, *Journal of Experimental Botany*, 65:1713-1735 (2014).

\* cited by examiner

SEQUENCE LISTING

<160> NUMBER OF SEQ ID NOS: 543

<210> SEQ ID NO 1
<211> LENGTH: 21
<212> TYPE: DNA
<213> ORGANISM: Brassica napus

```
<400> SEQUENCE: 1
tcattgagcg cagcgttgat g                                            21

<210> SEQ ID NO 2
<211> LENGTH: 21
<212> TYPE: DNA
<213> ORGANISM: Oryza sativa

<400> SEQUENCE: 2
tggaaggggc atgcagagga g                                            21

<210> SEQ ID NO 3
<211> LENGTH: 21
<212> TYPE: DNA
<213> ORGANISM: Solanum lycopersicum

<400> SEQUENCE: 3
tagccaagga tgacttgcct a                                            21

<210> SEQ ID NO 4
<211> LENGTH: 21
<212> TYPE: DNA
<213> ORGANISM: Selaginella moellendorffii

<400> SEQUENCE: 4
gctaggggca gtggtcaagg a                                            21

<210> SEQ ID NO 5
<211> LENGTH: 96
<212> TYPE: RNA
<213> ORGANISM: Brassica napus

<400> SEQUENCE: 5
gaacaucauu gagugcagcg uugaugugau uuacuucucu uuuucauugu ugaauggauu   60
aaagcaauuu acaucaacgu uggcucaauu auguuu                            96

<210> SEQ ID NO 6
<211> LENGTH: 88
<212> TYPE: DNA
<213> ORGANISM: Oryza sativa

<400> SEQUENCE: 6
agtggaaggg gcatgcagag gagcaggaga ttcagtttga agctggactt cactttttgcc  60 tctctctcct gtgcttgcct cttccatt                                     88

<210> SEQ ID NO 7
<211> LENGTH: 149
<212> TYPE: RNA
<213> ORGANISM: Solanum lycopersicum

<400> SEQUENCE: 7
ggucuauaag guuugcauga aguugaagag agucaaguug cagccaagga ugacuugccg   60
gaccaaaagu gugaccauu ucuaguucc ggcaaguugu uuuggcuau aaguuugcuc     120 ucuucuucuc auguuauccu cguuagacc                                   149

<210> SEQ ID NO 8
<211> LENGTH: 98
<212> TYPE: DNA
<213> ORGANISM: Selaginella moellendorffii

<400> SEQUENCE: 8
```

```
caacacaggg ttgctagggg cagtggtcaa ggatctgggg gcccatgtac tgccttccat    60
gggctcctag gtccttgagc gctgccccca gcaaccct                           98

<210> SEQ ID NO 9
<211> LENGTH: 21
<212> TYPE: DNA
<213> ORGANISM: Arabidopsis lyrata

<400> SEQUENCE: 9
tcattgagtg cagcgttgat g                                             21

<210> SEQ ID NO 10
<211> LENGTH: 21
<212> TYPE: DNA
<213> ORGANISM: Arabidopsis lyrata

<400> SEQUENCE: 10
tcattgagtg cagcgttgat g                                             21

<210> SEQ ID NO 11
<211> LENGTH: 21
<212> TYPE: DNA
<213> ORGANISM: Arabidopsis thaliana

<400> SEQUENCE: 11
tcattgagtg cagcgttgat g                                             21

<210> SEQ ID NO 12
<211> LENGTH: 21
<212> TYPE: DNA
<213> ORGANISM: Arabidopsis thaliana

<400> SEQUENCE: 12
tcattgagtg catcgttgat g                                             21

<210> SEQ ID NO 13
<211> LENGTH: 21
<212> TYPE: DNA
<213> ORGANISM: Brachypodium distachyon

<400> SEQUENCE: 13
tcattgagtg cagcgttgat g                                             21

<210> SEQ ID NO 14
<211> LENGTH: 21
<212> TYPE: DNA
<213> ORGANISM: Brachypodium distachyon

<400> SEQUENCE: 14
tcattgagtg cagcgttgat g                                             21

<210> SEQ ID NO 15
<211> LENGTH: 21
<212> TYPE: DNA
<213> ORGANISM: Brachypodium distachyon

<400> SEQUENCE: 15
attgagtgca gcgttgatga a                                             21

<210> SEQ ID NO 16
<211> LENGTH: 22
<212> TYPE: DNA
```

```
<213> ORGANISM: Brassica napus

<400> SEQUENCE: 16
tcattgagtg cagcgttgat gt                                            22

<210> SEQ ID NO 17
<211> LENGTH: 21
<212> TYPE: DNA
<213> ORGANISM: Citrus sinensis

<400> SEQUENCE: 17
tcattgagtg cagcgttgat g                                             21

<210> SEQ ID NO 18
<211> LENGTH: 22
<212> TYPE: DNA
<213> ORGANISM: Gossypium hirsutum

<400> SEQUENCE: 18
ttcattgagt gcagtgttga tt                                            22

<210> SEQ ID NO 19
<211> LENGTH: 21
<212> TYPE: DNA
<213> ORGANISM: Hordeum vulgare

<400> SEQUENCE: 19
ccgttgagtg cagcgttgat g                                             21

<210> SEQ ID NO 20
<211> LENGTH: 21
<212> TYPE: DNA
<213> ORGANISM: Oryza sativa

<400> SEQUENCE: 20
tcattgagtg cagcgttgat g                                             21

<210> SEQ ID NO 21
<211> LENGTH: 21
<212> TYPE: DNA
<213> ORGANISM: Oryza sativa

<400> SEQUENCE: 21
ttgagtgcag cgttgatgaa c                                             21

<210> SEQ ID NO 22
<211> LENGTH: 21
<212> TYPE: DNA
<213> ORGANISM: Oryza sativa

<400> SEQUENCE: 22
ttattgagtg cagcgttgat g                                             21

<210> SEQ ID NO 23
<211> LENGTH: 21
<212> TYPE: DNA
<213> ORGANISM: Oryza sativa

<400> SEQUENCE: 23
ttgagtgcag cgttgatgaa c                                             21

<210> SEQ ID NO 24
<211> LENGTH: 21
```

```
<212> TYPE: DNA
<213> ORGANISM: Picea abies

<400> SEQUENCE: 24
tcattgagtg cagcgttgac g                                              21

<210> SEQ ID NO 25
<211> LENGTH: 21
<212> TYPE: DNA
<213> ORGANISM: Populus trichocarpa

<400> SEQUENCE: 25
tcattgagtg cagcgttgat g                                              21

<210> SEQ ID NO 26
<211> LENGTH: 21
<212> TYPE: DNA
<213> ORGANISM: Populus trichocarpa

<400> SEQUENCE: 26
ccattgagtg cagcgttgat g                                              21

<210> SEQ ID NO 27
<211> LENGTH: 21
<212> TYPE: DNA
<213> ORGANISM: Populus trichocarpa

<400> SEQUENCE: 27
tcattgagtg gagctttgat g                                              21

<210> SEQ ID NO 28
<211> LENGTH: 21
<212> TYPE: DNA
<213> ORGANISM: Ricinus communis

<400> SEQUENCE: 28
tcattgagtg cagcgttgat g                                              21

<210> SEQ ID NO 29
<211> LENGTH: 21
<212> TYPE: DNA
<213> ORGANISM: Sorghum bicolor

<400> SEQUENCE: 29
tcattgagtg cagcgttgat g                                              21

<210> SEQ ID NO 30
<211> LENGTH: 20
<212> TYPE: DNA
<213> ORGANISM: Solanum lycopersicum

<400> SEQUENCE: 30
attgagtgca gcgttgatga                                                20

<210> SEQ ID NO 31
<211> LENGTH: 21
<212> TYPE: DNA
<213> ORGANISM: Theobroma cacao

<400> SEQUENCE: 31
tcattgagtg cagcgttgat g                                              21

<210> SEQ ID NO 32
```

```
<210> SEQ ID NO 32
<211> LENGTH: 21
<212> TYPE: DNA
<213> ORGANISM: Vitis vinifera

<400> SEQUENCE: 32
tcattgagtg cagcgttgat g                                              21

<210> SEQ ID NO 33
<211> LENGTH: 21
<212> TYPE: DNA
<213> ORGANISM: Vitis vinifera

<400> SEQUENCE: 33
tcattgagtg cagcgttgat g                                              21

<210> SEQ ID NO 34
<211> LENGTH: 21
<212> TYPE: DNA
<213> ORGANISM: Zea mays

<400> SEQUENCE: 34
tcattgagcg cagcgttgat g                                              21

<210> SEQ ID NO 35
<211> LENGTH: 21
<212> TYPE: DNA
<213> ORGANISM: Zea mays

<400> SEQUENCE: 35
tcattgagcg cagcgttgat g                                              21

<210> SEQ ID NO 36
<211> LENGTH: 21
<212> TYPE: DNA
<213> ORGANISM: Brachypodium distachyon

<400> SEQUENCE: 36 tggaagggc atgcagagga g                                               21

<210> SEQ ID NO 37
<211> LENGTH: 21
<212> TYPE: DNA
<213> ORGANISM: Medicago truncatula

<400> SEQUENCE: 37 ttgaagggc agggagagga g                                               21

<210> SEQ ID NO 38
<211> LENGTH: 21
<212> TYPE: DNA
<213> ORGANISM: Sorghum bicolor

<400> SEQUENCE: 38 tggaagggc atgcagagga g                                               21

<210> SEQ ID NO 39
<211> LENGTH: 21
<212> TYPE: DNA
<213> ORGANISM: Saccharum spp.

<400> SEQUENCE: 39 tggaagggc atgcagagga g                                               21
```

```
<210> SEQ ID NO 40
<211> LENGTH: 21
<212> TYPE: DNA
<213> ORGANISM: Zea mays

<400> SEQUENCE: 40 tggaagggc atgcagagga g                                              21

<210> SEQ ID NO 41
<211> LENGTH: 21
<212> TYPE: DNA
<213> ORGANISM: Zea mays

<400> SEQUENCE: 41
tggaaggggc atgcagagga g                                             21

<210> SEQ ID NO 42
<211> LENGTH: 21
<212> TYPE: DNA
<213> ORGANISM: Arabidopsis lyrata

<400> SEQUENCE: 42
cagccaagga tgacttgccg a                                             21

<210> SEQ ID NO 43
<211> LENGTH: 21
<212> TYPE: DNA
<213> ORGANISM: Arabidopsis lyrata

<400> SEQUENCE: 43
cagccaagga tgacttgccg g                                             21

<210> SEQ ID NO 44
<211> LENGTH: 21
<212> TYPE: DNA
<213> ORGANISM: Arabidopsis lyrata

<400> SEQUENCE: 44
cagccaagga tgacttgccg g                                             21

<210> SEQ ID NO 45
<211> LENGTH: 21
<212> TYPE: DNA
<213> ORGANISM: Arabidopsis lyrata

<400> SEQUENCE: 45
tgagccaagg atgacttgcc g                                             21

<210> SEQ ID NO 46
<211> LENGTH: 21
<212> TYPE: DNA
<213> ORGANISM: Arabidopsis lyrata

<400> SEQUENCE: 46
tgagccaagg atgacttgcc g                                             21

<210> SEQ ID NO 47
<211> LENGTH: 21
<212> TYPE: DNA
<213> ORGANISM: Arabidopsis lyrata

<400> SEQUENCE: 47
tgagccaagg atgacttgcc g                                             21
```

```
<210> SEQ ID NO 48
<211> LENGTH: 21
<212> TYPE: DNA
<213> ORGANISM: Arabidopsis lyrata

<400> SEQUENCE: 48
tgagccaagg atgacttgcc g                                         21

<210> SEQ ID NO 49
<211> LENGTH: 21
<212> TYPE: DNA
<213> ORGANISM: Arabidopsis lyrata

<400> SEQUENCE: 49
tagccaagga tgacttgcct g                                         21

<210> SEQ ID NO 50
<211> LENGTH: 21
<212> TYPE: DNA
<213> ORGANISM: Arabidopsis lyrata

<400> SEQUENCE: 50
tagccaagga tgacttgcct g                                         21

<210> SEQ ID NO 51
<211> LENGTH: 21
<212> TYPE: DNA
<213> ORGANISM: Arabidopsis lyrata

<400> SEQUENCE: 51
tagccaagga tgacttgcct g                                         21

<210> SEQ ID NO 52
<211> LENGTH: 21
<212> TYPE: DNA
<213> ORGANISM: Arabidopsis lyrata

<400> SEQUENCE: 52
tagccaagga tgacttgcct g                                         21

<210> SEQ ID NO 53
<211> LENGTH: 21
<212> TYPE: DNA
<213> ORGANISM: Arabidopsis lyrata

<400> SEQUENCE: 53
tagccaagga tgacttgcct g                                         21

<210> SEQ ID NO 54
<211> LENGTH: 21
<212> TYPE: DNA
<213> ORGANISM: Arabidopsis lyrata

<400> SEQUENCE: 54
tagccaagga tgacttgcct g                                         21

<210> SEQ ID NO 55
<211> LENGTH: 21
<212> TYPE: DNA
<213> ORGANISM: Arabidopsis lyrata

<400> SEQUENCE: 55
tagccaaaga tgacttgcct g                                         21
```

<210> SEQ ID NO 56
<211> LENGTH: 20
<212> TYPE: DNA
<213> ORGANISM: Antirrhinum majus

<400> SEQUENCE: 56
agccaaggat gacttgccga          20

<210> SEQ ID NO 57
<211> LENGTH: 21
<212> TYPE: DNA
<213> ORGANISM: Aquilegia coerulea

<400> SEQUENCE: 57
tagccaagga tgacttgcct a          21

<210> SEQ ID NO 58
<211> LENGTH: 21
<212> TYPE: DNA
<213> ORGANISM: Aquilegia coerulea

<400> SEQUENCE: 58
tagccaagga tgacttgcct g          21

<210> SEQ ID NO 59
<211> LENGTH: 21
<212> TYPE: DNA
<213> ORGANISM: Aquilegia coerulea

<400> SEQUENCE: 59
cagccaagga tgacttgccg g          21

<210> SEQ ID NO 60
<211> LENGTH: 21
<212> TYPE: DNA
<213> ORGANISM: Aegilops taushii

<400> SEQUENCE: 60
tagccaagga tgaattgcca g          21

<210> SEQ ID NO 61
<211> LENGTH: 21
<212> TYPE: DNA
<213> ORGANISM: Arabidopsis thaliana

<400> SEQUENCE: 61
cagccaagga tgacttgccg a          21

<210> SEQ ID NO 62
<211> LENGTH: 21
<212> TYPE: DNA
<213> ORGANISM: Arabidopsis thaliana

<400> SEQUENCE: 62
cagccaagga tgacttgccg g          21

<210> SEQ ID NO 63
<211> LENGTH: 21
<212> TYPE: DNA
<213> ORGANISM: Arabidopsis thaliana

<400> SEQUENCE: 63

```
cagccaagga tgacttgccg g                                              21

<210> SEQ ID NO 64
<211> LENGTH: 21
<212> TYPE: DNA
<213> ORGANISM: Arabidopsis thaliana

<400> SEQUENCE: 64
tgagccaagg atgacttgcc g                                              21

<210> SEQ ID NO 65
<211> LENGTH: 21
<212> TYPE: DNA
<213> ORGANISM: Arabidopsis thaliana

<400> SEQUENCE: 65
tgagccaagg atgacttgcc g                                              21

<210> SEQ ID NO 66
<211> LENGTH: 21
<212> TYPE: DNA
<213> ORGANISM: Arabidopsis thaliana

<400> SEQUENCE: 66
tgagccaagg atgacttgcc g                                              21

<210> SEQ ID NO 67
<211> LENGTH: 21
<212> TYPE: DNA
<213> ORGANISM: Arabidopsis thaliana

<400> SEQUENCE: 67
tgagccaagg atgacttgcc g                                              21

<210> SEQ ID NO 68
<211> LENGTH: 21
<212> TYPE: DNA
<213> ORGANISM: Arabidopsis thaliana

<400> SEQUENCE: 68
tagccaagga tgacttgcct g                                              21

<210> SEQ ID NO 69
<211> LENGTH: 21
<212> TYPE: DNA
<213> ORGANISM: Arabidopsis thaliana

<400> SEQUENCE: 69
tagccaagga tgacttgcct g                                              21

<210> SEQ ID NO 70
<211> LENGTH: 21
<212> TYPE: DNA
<213> ORGANISM: Arabidopsis thaliana

<400> SEQUENCE: 70
tagccaagga tgacttgcct g                                              21

<210> SEQ ID NO 71
<211> LENGTH: 21
<212> TYPE: DNA
<213> ORGANISM: Arabidopsis thaliana

<400> SEQUENCE: 71
```
tagccaagga tgacttgcct g     21

<210> SEQ ID NO 72
<211> LENGTH: 21
<212> TYPE: DNA
<213> ORGANISM: Arabidopsis thaliana

<400> SEQUENCE: 72
tagccaagga tgacttgcct g     21

<210> SEQ ID NO 73
<211> LENGTH: 21
<212> TYPE: DNA
<213> ORGANISM: Arabidopsis thaliana

<400> SEQUENCE: 73
tagccaagga tgacttgcct g     21

<210> SEQ ID NO 74
<211> LENGTH: 21
<212> TYPE: DNA
<213> ORGANISM: Arabidopsis thaliana

<400> SEQUENCE: 74
tagccaagga tgacttgcct g     21

<210> SEQ ID NO 75
<211> LENGTH: 21
<212> TYPE: DNA
<213> ORGANISM: Brachypodium distachyon

<400> SEQUENCE: 75
cagccaagga tgacttgccg a     21

<210> SEQ ID NO 76
<211> LENGTH: 21
<212> TYPE: DNA
<213> ORGANISM: Brachypodium distachyon

<400> SEQUENCE: 76
tagccaagga tgacttgccg g     21

<210> SEQ ID NO 77
<211> LENGTH: 21
<212> TYPE: DNA
<213> ORGANISM: Brachypodium distachyon

<400> SEQUENCE: 77
cagccaagga tgacttgccg g     21

<210> SEQ ID NO 78
<211> LENGTH: 21
<212> TYPE: DNA
<213> ORGANISM: Brachypodium distachyon

<400> SEQUENCE: 78
tagccaagaa tgacttgcct a     21

<210> SEQ ID NO 79
<211> LENGTH: 21
<212> TYPE: DNA
<213> ORGANISM: Brachypodium distachyon

```
<400> SEQUENCE: 79
tagccaagga tgacttgcct g                                              21

<210> SEQ ID NO 80
<211> LENGTH: 21
<212> TYPE: DNA
<213> ORGANISM: Brachypodium distachyon

<400> SEQUENCE: 80
cagccaagga tgacttgccg g                                              21

<210> SEQ ID NO 81
<211> LENGTH: 21
<212> TYPE: DNA
<213> ORGANISM: Brachypodium distachyon

<400> SEQUENCE: 81
tagccaagga tgacttgcct g                                              21

<210> SEQ ID NO 82
<211> LENGTH: 21
<212> TYPE: DNA
<213> ORGANISM: Brachypodium distachyon

<400> SEQUENCE: 82
tagccaagga tgacttgcct a                                              21

<210> SEQ ID NO 83
<211> LENGTH: 22
<212> TYPE: DNA
<213> ORGANISM: Brachypodium distachyon

<400> SEQUENCE: 83
ccagccaaga atggcttgcc ta                                             22

<210> SEQ ID NO 84
<211> LENGTH: 21
<212> TYPE: DNA
<213> ORGANISM: Brachypodium distachyon

<400> SEQUENCE: 84
tagccaggaa tggcttgcct a                                              21

<210> SEQ ID NO 85
<211> LENGTH: 22
<212> TYPE: DNA
<213> ORGANISM: Brachypodium distachyon

<400> SEQUENCE: 85
tagccaagga tgatttgcct gt                                             22

<210> SEQ ID NO 86
<211> LENGTH: 21
<212> TYPE: DNA
<213> ORGANISM: Brassica napus

<400> SEQUENCE: 86
cagccaagga tgacttgccg a                                              21

<210> SEQ ID NO 87
<211> LENGTH: 21
<212> TYPE: DNA
<213> ORGANISM: Brassica napus
```

<400> SEQUENCE: 87
cagccaagga tgacttgccg a                                              21

<210> SEQ ID NO 88
<211> LENGTH: 21
<212> TYPE: DNA
<213> ORGANISM: Brassica napus

<400> SEQUENCE: 88
tagccaagga tgacttgcct a                                              21

<210> SEQ ID NO 89
<211> LENGTH: 21
<212> TYPE: DNA
<213> ORGANISM: Brassica napus

<400> SEQUENCE: 89
tagccaagga tgacttgcct a                                              21

<210> SEQ ID NO 90
<211> LENGTH: 21
<212> TYPE: DNA
<213> ORGANISM: Brassica napus

<400> SEQUENCE: 90
tagccaagga tgacttgcct a                                              21

<210> SEQ ID NO 91
<211> LENGTH: 21
<212> TYPE: DNA
<213> ORGANISM: Brassica napus

<400> SEQUENCE: 91
tagccaagga tgacttgcct a                                              21

<210> SEQ ID NO 92
<211> LENGTH: 22
<212> TYPE: DNA
<213> ORGANISM: Brassica napus

<400> SEQUENCE: 92
tagccaagga tgacttgcct gc                                             22

<210> SEQ ID NO 93
<211> LENGTH: 22
<212> TYPE: DNA
<213> ORGANISM: Brassica napus

<400> SEQUENCE: 93
tagccaagga tgacttgcct gc                                             22

<210> SEQ ID NO 94
<211> LENGTH: 22
<212> TYPE: DNA
<213> ORGANISM: Brassica napus

<400> SEQUENCE: 94
tagccaagga tgacttgcct gc                                             22

<210> SEQ ID NO 95
<211> LENGTH: 22
<212> TYPE: DNA

<213> ORGANISM: Brassica napus

<400> SEQUENCE: 95
tagccaagga tgacttgcct gc                                          22

<210> SEQ ID NO 96
<211> LENGTH: 22
<212> TYPE: DNA
<213> ORGANISM: Brassica napus

<400> SEQUENCE: 96
tagccaagga tgacttgcct gc                                          22

<210> SEQ ID NO 97
<211> LENGTH: 22
<212> TYPE: DNA
<213> ORGANISM: Brassica napus

<400> SEQUENCE: 97
tagccaagga tgacttgcct gc                                          22

<210> SEQ ID NO 98
<211> LENGTH: 21
<212> TYPE: DNA
<213> ORGANISM: Brassica napus

<400> SEQUENCE: 98
tgagccaaag atgacttgcc g                                           21

<210> SEQ ID NO 99
<211> LENGTH: 21
<212> TYPE: DNA
<213> ORGANISM: Citrus sinensis

<400> SEQUENCE: 99
gagccaagaa tgacttgccg a                                           21

<210> SEQ ID NO 100
<211> LENGTH: 21
<212> TYPE: DNA
<213> ORGANISM: Festuca arundinacea

<400> SEQUENCE: 100
tagccaagga tgacttgcct a                                           21

<210> SEQ ID NO 101
<211> LENGTH: 21
<212> TYPE: DNA
<213> ORGANISM: Gossypium herbaceum

<400> SEQUENCE: 101
tagccaagga tgacttgcct g                                           21

<210> SEQ ID NO 102
<211> LENGTH: 21
<212> TYPE: DNA
<213> ORGANISM: Glycine max

<400> SEQUENCE: 102
cagccaagga tgacttgccg g                                           21

<210> SEQ ID NO 103
<211> LENGTH: 21

```
<212> TYPE: DNA
<213> ORGANISM: Glycine max

<400> SEQUENCE: 103
cagccaagga tgacttgccg a                                              21

<210> SEQ ID NO 104
<211> LENGTH: 21
<212> TYPE: DNA
<213> ORGANISM: Glycine max

<400> SEQUENCE: 104
aagccaagga tgacttgccg a                                              21

<210> SEQ ID NO 105
<211> LENGTH: 23
<212> TYPE: DNA
<213> ORGANISM: Glycine max

<400> SEQUENCE: 105
tgagccaagg atgacttgcc ggt                                            23

<210> SEQ ID NO 106
<211> LENGTH: 20
<212> TYPE: DNA
<213> ORGANISM: Glycine max

<400> SEQUENCE: 106
agccaaggat gacttgccgg                                                20

<210> SEQ ID NO 107
<211> LENGTH: 21
<212> TYPE: DNA
<213> ORGANISM: Glycine max

<400> SEQUENCE: 107
cagccaagga tgacttgccg g                                              21

<210> SEQ ID NO 108
<211> LENGTH: 21
<212> TYPE: DNA
<213> ORGANISM: Glycine soja

<400> SEQUENCE: 108
cagccaagga tgacttgccg g                                              21

<210> SEQ ID NO 109
<211> LENGTH: 21
<212> TYPE: DNA
<213> ORGANISM: Hordeum vulgare

<400> SEQUENCE: 109
aagccaagga tgagttgcct g                                              21

<210> SEQ ID NO 110
<211> LENGTH: 21
<212> TYPE: DNA
<213> ORGANISM: Medicago truncatula

<400> SEQUENCE: 110
cagccaagga tgacttgccg a                                              21

<210> SEQ ID NO 111
```

```
<211> LENGTH: 21
<212> TYPE: DNA
<213> ORGANISM: Medicago truncatula

<400> SEQUENCE: 111
cagccaagga tgacttgccg a                                              21

<210> SEQ ID NO 112
<211> LENGTH: 21
<212> TYPE: DNA
<213> ORGANISM: Medicago truncatula

<400> SEQUENCE: 112
tagccaagga caacttgccg g                                              21

<210> SEQ ID NO 113
<211> LENGTH: 21
<212> TYPE: DNA
<213> ORGANISM: Medicago truncatula

<400> SEQUENCE: 113
aagccaagga tgacttgccg g                                              21

<210> SEQ ID NO 114
<211> LENGTH: 21
<212> TYPE: DNA
<213> ORGANISM: Medicago truncatula

<400> SEQUENCE: 114
ggagccaagg atgacttgcc g                                              21

<210> SEQ ID NO 115
<211> LENGTH: 21
<212> TYPE: DNA
<213> ORGANISM: Medicago truncatula

<400> SEQUENCE: 115
aagccaagga tgacttgcct a                                              21

<210> SEQ ID NO 116
<211> LENGTH: 21
<212> TYPE: DNA
<213> ORGANISM: Medicago truncatula

<400> SEQUENCE: 116
cagccaagga tgacttgccg g                                              21

<210> SEQ ID NO 117
<211> LENGTH: 21
<212> TYPE: DNA
<213> ORGANISM: Medicago truncatula

<400> SEQUENCE: 117
gagccaaaga tgacttgccg g                                              21

<210> SEQ ID NO 118
<211> LENGTH: 21
<212> TYPE: DNA
<213> ORGANISM: Medicago truncatula

<400> SEQUENCE: 118
tgagccaaag atgacttgcc g                                              21
```

```
<210> SEQ ID NO 119
<211> LENGTH: 21
<212> TYPE: DNA
<213> ORGANISM: Medicago truncatula

<400> SEQUENCE: 119
cagccaagga tgacttgccg g                                              21

<210> SEQ ID NO 120
<211> LENGTH: 21
<212> TYPE: DNA
<213> ORGANISM: Medicago truncatula

<400> SEQUENCE: 120
aagccaagga tgacttgccg g                                              21

<210> SEQ ID NO 121
<211> LENGTH: 21
<212> TYPE: DNA
<213> ORGANISM: Medicago truncatula

<400> SEQUENCE: 121
gagccaagga tgacttgccg g                                              21

<210> SEQ ID NO 122
<211> LENGTH: 21
<212> TYPE: DNA
<213> ORGANISM: Medicago truncatula

<400> SEQUENCE: 122
tgagccaaag atgacttgcc g                                              21

<210> SEQ ID NO 123
<211> LENGTH: 21
<212> TYPE: DNA
<213> ORGANISM: Medicago truncatula

<400> SEQUENCE: 123
tgagccaaag atgacttgcc g                                              21

<210> SEQ ID NO 124
<211> LENGTH: 21
<212> TYPE: DNA
<213> ORGANISM: Oryza sativa

<400> SEQUENCE: 124
cagccaagga tgacttgccg g                                              21

<210> SEQ ID NO 125
<211> LENGTH: 21
<212> TYPE: DNA
<213> ORGANISM: Oryza sativa

<400> SEQUENCE: 125
tagccaagga tgaattgccg g                                              21

<210> SEQ ID NO 126
<211> LENGTH: 21
<212> TYPE: DNA
<213> ORGANISM: Oryza sativa

<400> SEQUENCE: 126
tagccaagga tgacttgccg g                                              21
```

-continued

```
<210> SEQ ID NO 127
<211> LENGTH: 21
<212> TYPE: DNA
<213> ORGANISM: Oryza sativa

<400> SEQUENCE: 127
tagccaagga tgacttgcct a                                              21

<210> SEQ ID NO 128
<211> LENGTH: 21
<212> TYPE: DNA
<213> ORGANISM: Oryza sativa

<400> SEQUENCE: 128
tagccaagga tgacttgcct a                                              21

<210> SEQ ID NO 129
<211> LENGTH: 21
<212> TYPE: DNA
<213> ORGANISM: Oryza sativa

<400> SEQUENCE: 129
tagccaagga tgacttgcct g                                              21

<210> SEQ ID NO 130
<211> LENGTH: 21
<212> TYPE: DNA
<213> ORGANISM: Oryza sativa

<400> SEQUENCE: 130
tagccaagga tgacttgcct g                                              21

<210> SEQ ID NO 131
<211> LENGTH: 21
<212> TYPE: DNA
<213> ORGANISM: Oryza sativa

<400> SEQUENCE: 131
tagccaagga tgacttgcct g                                              21

<210> SEQ ID NO 132
<211> LENGTH: 21
<212> TYPE: DNA
<213> ORGANISM: Oryza sativa

<400> SEQUENCE: 132
tagccaagga tgacttgcct g                                              21

<210> SEQ ID NO 133
<211> LENGTH: 21
<212> TYPE: DNA
<213> ORGANISM: Oryza sativa

<400> SEQUENCE: 133
tagccaagga tgacttgcct g                                              21

<210> SEQ ID NO 134
<211> LENGTH: 21
<212> TYPE: DNA
<213> ORGANISM: Oryza sativa

<400> SEQUENCE: 134
tagccaagga tgacttgcct g                                              21
```

<210> SEQ ID NO 135
<211> LENGTH: 21
<212> TYPE: DNA
<213> ORGANISM: Oryza sativa

<400> SEQUENCE: 135
tagccaagaa tgacttgcct a                                              21

<210> SEQ ID NO 136
<211> LENGTH: 21
<212> TYPE: DNA
<213> ORGANISM: Oryza sativa

<400> SEQUENCE: 136
tagccaagaa tgacttgcct a                                              21

<210> SEQ ID NO 137
<211> LENGTH: 22
<212> TYPE: DNA
<213> ORGANISM: Oryza sativa

<400> SEQUENCE: 137
tagccaagga caaacttgcc gg                                             22

<210> SEQ ID NO 138
<211> LENGTH: 21
<212> TYPE: DNA
<213> ORGANISM: Oryza sativa

<400> SEQUENCE: 138
tagccaagga gactgcccat g                                              21

<210> SEQ ID NO 139
<211> LENGTH: 21
<212> TYPE: DNA
<213> ORGANISM: Petunia x hybrida

<400> SEQUENCE: 139
cagccaagga tgacttgccg g                                              21

<210> SEQ ID NO 140
<211> LENGTH: 21
<212> TYPE: DNA
<213> ORGANISM: Populus trichocarpa

<400> SEQUENCE: 140
cagccaagga tgacttgccg a                                              21

<210> SEQ ID NO 141
<211> LENGTH: 21
<212> TYPE: DNA
<213> ORGANISM: Populus trichocarpa

<400> SEQUENCE: 141
tagccaagga cgacttgccc a                                              21

<210> SEQ ID NO 142
<211> LENGTH: 21
<212> TYPE: DNA
<213> ORGANISM: Populus trichocarpa

<400> SEQUENCE: 142
tagccaagga cgacttgccc a                                              21

<210> SEQ ID NO 143
<211> LENGTH: 21
<212> TYPE: DNA
<213> ORGANISM: Populus trichocarpa

<400> SEQUENCE: 143
tagccaagga cgacttgccc a                                              21

<210> SEQ ID NO 144
<211> LENGTH: 21
<212> TYPE: DNA
<213> ORGANISM: Populus trichocarpa

<400> SEQUENCE: 144
tagccaagga cgacttgccc a                                              21

<210> SEQ ID NO 145
<211> LENGTH: 21
<212> TYPE: DNA
<213> ORGANISM: Populus trichocarpa

<400> SEQUENCE: 145
tagccaagga cgacttgccc a                                              21

<210> SEQ ID NO 146
<211> LENGTH: 21
<212> TYPE: DNA
<213> ORGANISM: Populus trichocarpa

<400> SEQUENCE: 146
cagccaagga tgacttgccg a                                              21

<210> SEQ ID NO 147
<211> LENGTH: 21
<212> TYPE: DNA
<213> ORGANISM: Populus trichocarpa

<400> SEQUENCE: 147
cagccaagga tgacttgccg a                                              21

<210> SEQ ID NO 148
<211> LENGTH: 21
<212> TYPE: DNA
<213> ORGANISM: Populus trichocarpa

<400> SEQUENCE: 148
cagccaagga tgacttgccg g                                              21

<210> SEQ ID NO 149
<211> LENGTH: 21
<212> TYPE: DNA
<213> ORGANISM: Populus trichocarpa

<400> SEQUENCE: 149
cagccaagga tgacttgccg g                                              21

<210> SEQ ID NO 150
<211> LENGTH: 21
<212> TYPE: DNA
<213> ORGANISM: Populus trichocarpa

<400> SEQUENCE: 150
cagccaagga tgacttgccg g                                        21

<210> SEQ ID NO 151
<211> LENGTH: 21
<212> TYPE: DNA
<213> ORGANISM: Populus trichocarpa

<400> SEQUENCE: 151
cagccaagga tgacttgccg g                                        21

<210> SEQ ID NO 152
<211> LENGTH: 21
<212> TYPE: DNA
<213> ORGANISM: Populus trichocarpa

<400> SEQUENCE: 152
cagccaagga tgacttgccg g                                        21

<210> SEQ ID NO 153
<211> LENGTH: 21
<212> TYPE: DNA
<213> ORGANISM: Populus trichocarpa

<400> SEQUENCE: 153
tagccaagga tgacttgcct g                                        21

<210> SEQ ID NO 154
<211> LENGTH: 21
<212> TYPE: DNA
<213> ORGANISM: Populus trichocarpa

<400> SEQUENCE: 154
tagccaagga tgacttgcct g                                        21

<210> SEQ ID NO 155
<211> LENGTH: 21
<212> TYPE: DNA
<213> ORGANISM: Populus trichocarpa

<400> SEQUENCE: 155
tagccaagga tgacttgcct g                                        21

<210> SEQ ID NO 156
<211> LENGTH: 21
<212> TYPE: DNA
<213> ORGANISM: Populus trichocarpa

<400> SEQUENCE: 156
tagccaagga tgacttgcct g                                        21

<210> SEQ ID NO 157
<211> LENGTH: 21
<212> TYPE: DNA
<213> ORGANISM: Populus trichocarpa

<400> SEQUENCE: 157
tagccaagga tgacttgcct g                                        21

<210> SEQ ID NO 158
<211> LENGTH: 21
<212> TYPE: DNA
<213> ORGANISM: Populus trichocarpa

```
<400> SEQUENCE: 158
tgagccaagg atgacttgcc g                                              21

<210> SEQ ID NO 159
<211> LENGTH: 21
<212> TYPE: DNA
<213> ORGANISM: Populus trichocarpa

<400> SEQUENCE: 159
aagccaagga tgacttgcct g                                              21

<210> SEQ ID NO 160
<211> LENGTH: 21
<212> TYPE: DNA
<213> ORGANISM: Populus trichocarpa

<400> SEQUENCE: 160
aagccaagga tgacttgcct g                                              21

<210> SEQ ID NO 161
<211> LENGTH: 21
<212> TYPE: DNA
<213> ORGANISM: Populus trichocarpa

<400> SEQUENCE: 161
tagccaagga cgacttgcct g                                              21

<210> SEQ ID NO 162
<211> LENGTH: 21
<212> TYPE: DNA
<213> ORGANISM: Populus trichocarpa

<400> SEQUENCE: 162
tagccaagga tgacttgcct a                                              21

<210> SEQ ID NO 163
<211> LENGTH: 21
<212> TYPE: DNA
<213> ORGANISM: Populus trichocarpa

<400> SEQUENCE: 163
tcagccaagg atgacttgcc g                                              21

<210> SEQ ID NO 164
<211> LENGTH: 21
<212> TYPE: DNA
<213> ORGANISM: Populus trichocarpa

<400> SEQUENCE: 164
gagccaagaa tgacttgccg g                                              21

<210> SEQ ID NO 165
<211> LENGTH: 21
<212> TYPE: DNA
<213> ORGANISM: Populus trichocarpa

<400> SEQUENCE: 165
tagccaagga cgacttgcct a                                              21

<210> SEQ ID NO 166
<211> LENGTH: 21
<212> TYPE: DNA
<213> ORGANISM: Populus trichocarpa
```

<400> SEQUENCE: 166
tagccaagga tgacttgccc a                                              21

<210> SEQ ID NO 167
<211> LENGTH: 21
<212> TYPE: DNA
<213> ORGANISM: Populus trichocarpa

<400> SEQUENCE: 167
tagccaagga tgacttgccc a                                              21

<210> SEQ ID NO 168
<211> LENGTH: 21
<212> TYPE: DNA
<213> ORGANISM: Populus trichocarpa

<400> SEQUENCE: 168
tagccaagga tgacttgctc g                                              21

<210> SEQ ID NO 169
<211> LENGTH: 21
<212> TYPE: DNA
<213> ORGANISM: Populus trichocarpa

<400> SEQUENCE: 169
tagccatgga tgaattgcct g                                              21

<210> SEQ ID NO 170
<211> LENGTH: 21
<212> TYPE: DNA
<213> ORGANISM: Populus trichocarpa

<400> SEQUENCE: 170
cagccaagaa tgatttgccg g                                              21

<210> SEQ ID NO 171
<211> LENGTH: 21
<212> TYPE: DNA
<213> ORGANISM: Phaeodactylum tricornutum

<400> SEQUENCE: 171
cagccaagga tgacttgccg a                                              21

<210> SEQ ID NO 172
<211> LENGTH: 21
<212> TYPE: DNA
<213> ORGANISM: Phaeodactylum tricornutum

<400> SEQUENCE: 172
cagccaagga tgatttgccg a                                              21

<210> SEQ ID NO 173
<211> LENGTH: 21
<212> TYPE: DNA
<213> ORGANISM: Ricinus communis

<400> SEQUENCE: 173
cagccaagga tgacttgccg g                                              21

<210> SEQ ID NO 174
<211> LENGTH: 21
<212> TYPE: DNA

```
<213> ORGANISM: Ricinus communis

<400> SEQUENCE: 174
cagccaagga tgacttgccg g

```
<212> TYPE: DNA
<213> ORGANISM: Sorghum bicolor

<400> SEQUENCE: 182
tagccaagga tgacttgcct g                                              21

<210> SEQ ID NO 183
<211> LENGTH: 21
<212> TYPE: DNA
<213> ORGANISM: Sorghum bicolor

<400> SEQUENCE: 183
tagccaagga tgacttgcct a                                              21

<210> SEQ ID NO 184
<211> LENGTH: 21
<212> TYPE: DNA
<213> ORGANISM: Sorghum bicolor

<400> SEQUENCE: 184
tagccaagaa tgacttgcct a                                              21

<210> SEQ ID NO 185
<211> LENGTH: 21
<212> TYPE: DNA
<213> ORGANISM: Sorghum bicolor

<400> SEQUENCE: 185
tagccaagga tgacttgccg g                                              21

<210> SEQ ID NO 186
<211> LENGTH: 21
<212> TYPE: DNA
<213> ORGANISM: Sorghum bicolor

<400> SEQUENCE: 186
cagccaagga tgacttgccg g                                              21

<210> SEQ ID NO 187
<211> LENGTH: 21
<212> TYPE: DNA
<213> ORGANISM: Sorghum bicolor

<400> SEQUENCE: 187
tagccaagga tgacttgcct g                                              21

<210> SEQ ID NO 188
<211> LENGTH: 21
<212> TYPE: DNA
<213> ORGANISM: Sorghum bicolor

<400> SEQUENCE: 188
tagccaagga tgacttgcct a                                              21

<210> SEQ ID NO 189
<211> LENGTH: 21
<212> TYPE: DNA
<213> ORGANISM: Sorghum bicolor

<400> SEQUENCE: 189
tagccaagga tgacttgcct a                                              21

<210> SEQ ID NO 190
```

-continued

<210> SEQ ID NO 190
<211> LENGTH: 21
<212> TYPE: DNA
<213> ORGANISM: Sorghum bicolor

<400> SEQUENCE: 190
tagccaagga tgatttgcct g                                            21

<210> SEQ ID NO 191
<211> LENGTH: 21
<212> TYPE: DNA
<213> ORGANISM: Sorghum bicolor

<400> SEQUENCE: 191
tagccaagaa tggcttgcct a                                            21

<210> SEQ ID NO 192
<211> LENGTH: 21
<212> TYPE: DNA
<213> ORGANISM: Sorghum bicolor

<400> SEQUENCE: 192
tagccaagaa tggcttgcct a                                            21

<210> SEQ ID NO 193
<211> LENGTH: 21
<212> TYPE: DNA
<213> ORGANISM: Solanum lycopersicum

<400> SEQUENCE: 193
cagccaagga tgacttgccg g                                            21

<210> SEQ ID NO 194
<211> LENGTH: 21
<212> TYPE: DNA
<213> ORGANISM: Solanum lycopersicum

<400> SEQUENCE: 194
tagccaagga tgacttgcct g                                            21

<210> SEQ ID NO 195
<211> LENGTH: 21
<212> TYPE: DNA
<213> ORGANISM: Solanum lycopersicum

<400> SEQUENCE: 195
cagccaagga tgacttgccg a                                            21

<210> SEQ ID NO 196
<211> LENGTH: 21
<212> TYPE: DNA
<213> ORGANISM: Saccharum officinarum

<400> SEQUENCE: 196
tagccaagga tgacttgccg g                                            21

<210> SEQ ID NO 197
<211> LENGTH: 21
<212> TYPE: DNA
<213> ORGANISM: Saccharum spp.

<400> SEQUENCE: 197
tagccaagga tgacttgccg g                                            21

```
<210> SEQ ID NO 198
<211> LENGTH: 21
<212> TYPE: DNA
<213> ORGANISM: Theobroma cacao

<400> SEQUENCE: 198
cagccaagga tgacttgccg a                                              21

<210> SEQ ID NO 199
<211> LENGTH: 21
<212> TYPE: DNA
<213> ORGANISM: Theobroma cacao

<400> SEQUENCE: 199
cagccaagga tgacttgccg g                                              21

<210> SEQ ID NO 200
<211> LENGTH: 21
<212> TYPE: DNA
<213> ORGANISM: Theobroma cacao

<400> SEQUENCE: 200
cagccaagga tgacttgccg a                                              21

<210> SEQ ID NO 201
<211> LENGTH: 21
<212> TYPE: DNA
<213> ORGANISM: Theobroma cacao

<400> SEQUENCE: 201
tagccaagga tgacttgcct a                                              21

<210> SEQ ID NO 202
<211> LENGTH: 21
<212> TYPE: DNA
<213> ORGANISM: Theobroma cacao

<400> SEQUENCE: 202
cagccaagga tgacttgccg a                                              21

<210> SEQ ID NO 203
<211> LENGTH: 21
<212> TYPE: DNA
<213> ORGANISM: Theobroma cacao

<400> SEQUENCE: 203
aagccaagaa tgacttgcct g                                              21

<210> SEQ ID NO 204
<211> LENGTH: 21
<212> TYPE: DNA
<213> ORGANISM: Theobroma cacao

<400> SEQUENCE: 204
tagccaggga tgacttgcct a                                              21

<210> SEQ ID NO 205
<211> LENGTH: 21
<212> TYPE: DNA
<213> ORGANISM: Theobroma cacao

<400> SEQUENCE: 205
tagccaagga tgacttgcct g                                              21
```

<210> SEQ ID NO 206
<211> LENGTH: 21
<212> TYPE: DNA
<213> ORGANISM: Theobroma cacao

<400> SEQUENCE: 206
tagccaagga tgagttgcct g                                    21

<210> SEQ ID NO 207
<211> LENGTH: 21
<212> TYPE: DNA
<213> ORGANISM: Theobroma cacao

<400> SEQUENCE: 207
tagccaagga tgacttgcct g                                    21

<210> SEQ ID NO 208
<211> LENGTH: 21
<212> TYPE: DNA
<213> ORGANISM: Theobroma cacao

<400> SEQUENCE: 208
cagccaagga tgacttgccg g                                    21

<210> SEQ ID NO 209
<211> LENGTH: 21
<212> TYPE: DNA
<213> ORGANISM: Theobroma cacao

<400> SEQUENCE: 209
cagccaagga tgacttgccg g                                    21

<210> SEQ ID NO 210
<211> LENGTH: 21
<212> TYPE: DNA
<213> ORGANISM: Theobroma cacao

<400> SEQUENCE: 210
tgagccaagg atgacttgcc g                                    21

<210> SEQ ID NO 211
<211> LENGTH: 21
<212> TYPE: DNA
<213> ORGANISM: Vitis vinifera

<400> SEQUENCE: 211
cagccaagga tgacttgccg g                                    21

<210> SEQ ID NO 212
<211> LENGTH: 21
<212> TYPE: DNA
<213> ORGANISM: Vitis vinifera

<400> SEQUENCE: 212
tgagccaagg atggcttgcc g                                    21

<210> SEQ ID NO 213
<211> LENGTH: 21
<212> TYPE: DNA
<213> ORGANISM: Vitis vinifera

<400> SEQUENCE: 213
cagccaagga tgacttgccg g                                    21

<210> SEQ ID NO 214
<211> LENGTH: 22
<212> TYPE: DNA
<213> ORGANISM: Vitis vinifera

<400> SEQUENCE: 214
tagccaagga tgacttgcct gc                                            22

<210> SEQ ID NO 215
<211> LENGTH: 21
<212> TYPE: DNA
<213> ORGANISM: Vitis vinifera

<400> SEQUENCE: 215
cagccaagga tgacttgccg a                                             21

<210> SEQ ID NO 216
<211> LENGTH: 21
<212> TYPE: DNA
<213> ORGANISM: Vitis vinifera

<400> SEQUENCE: 216
cagccaagga tgacttgccg a                                             21

<210> SEQ ID NO 217
<211> LENGTH: 21
<212> TYPE: DNA
<213> ORGANISM: Vitis vinifera

<400> SEQUENCE: 217
tgagccaagg atggcttgcc g                                             21

<210> SEQ ID NO 218
<211> LENGTH: 21
<212> TYPE: DNA
<213> ORGANISM: Vitis vinifera

<400> SEQUENCE: 218
gagccaagga tgactggccg t                                             21

<210> SEQ ID NO 219
<211> LENGTH: 21
<212> TYPE: DNA
<213> ORGANISM: Vitis vinifera

<400> SEQUENCE: 219
cagccaagga tgacttgccg g                                             21

<210> SEQ ID NO 220
<211> LENGTH: 21
<212> TYPE: DNA
<213> ORGANISM: Vitis vinifera

<400> SEQUENCE: 220
cagccaagga tgacttgccg g                                             21

<210> SEQ ID NO 221
<211> LENGTH: 21
<212> TYPE: DNA
<213> ORGANISM: Vitis vinifera

<400> SEQUENCE: 221
gagccaagga tgacttgccg t     21

<210> SEQ ID NO 222
<211> LENGTH: 21
<212> TYPE: DNA
<213> ORGANISM: Vitis vinifera

<400> SEQUENCE: 222
gagccaagga tgacttgccg g     21

<210> SEQ ID NO 223
<211> LENGTH: 21
<212> TYPE: DNA
<213> ORGANISM: Vitis vinifera

<400> SEQUENCE: 223
gagccaagga tgacttgccg g     21

<210> SEQ ID NO 224
<211> LENGTH: 21
<212> TYPE: DNA
<213> ORGANISM: Vitis vinifera

<400> SEQUENCE: 224
gagccaagga tgacttgccg c     21

<210> SEQ ID NO 225
<211> LENGTH: 21
<212> TYPE: DNA
<213> ORGANISM: Vitis vinifera

<400> SEQUENCE: 225
gagccaagga tgacttgccg g     21

<210> SEQ ID NO 226
<211> LENGTH: 21
<212> TYPE: DNA
<213> ORGANISM: Vitis vinifera

<400> SEQUENCE: 226
gagccaagga tgacttgccg g     21

<210> SEQ ID NO 227
<211> LENGTH: 21
<212> TYPE: DNA
<213> ORGANISM: Vitis vinifera

<400> SEQUENCE: 227
tgagtcaagg atgacttgcc g     21

<210> SEQ ID NO 228
<211> LENGTH: 21
<212> TYPE: DNA
<213> ORGANISM: Vitis vinifera

<400> SEQUENCE: 228
cagccaagga tgacttgccg g     21

<210> SEQ ID NO 229
<211> LENGTH: 21
<212> TYPE: DNA
<213> ORGANISM: Vitis vinifera

<400> SEQUENCE: 229

```
cgagtcaagg atgacttgcc g                                           21

<210> SEQ ID NO 230
<211> LENGTH: 21
<212> TYPE: DNA
<213> ORGANISM: Vitis vinifera

<400> SEQUENCE: 230
tgagtcaagg atgacttgcc g                                           21

<210> SEQ ID NO 231
<211> LENGTH: 21
<212> TYPE: DNA
<213> ORGANISM: Vitis vinifera

<400> SEQUENCE: 231
aagccaagga tgaattgccg g                                           21

<210> SEQ ID NO 232
<211> LENGTH: 21
<212> TYPE: DNA
<213> ORGANISM: Vitis vinifera

<400> SEQUENCE: 232
cagccaagga tgacttgccg g                                           21

<210> SEQ ID NO 233
<211> LENGTH: 21
<212> TYPE: DNA
<213> ORGANISM: Vitis vinifera

<400> SEQUENCE: 233
tagccaagga tgacttgcct a                                           21

<210> SEQ ID NO 234
<211> LENGTH: 21
<212> TYPE: DNA
<213> ORGANISM: Vitis vinifera

<400> SEQUENCE: 234
tagcgaagga tgacttgcct a                                           21

<210> SEQ ID NO 235
<211> LENGTH: 21
<212> TYPE: DNA
<213> ORGANISM: Zea mays

<400> SEQUENCE: 235
cagccaagga tgacttgccg a                                           21

<210> SEQ ID NO 236
<211> LENGTH: 21
<212> TYPE: DNA
<213> ORGANISM: Zea mays

<400> SEQUENCE: 236
cagccaagga tgacttgccg a                                           21

<210> SEQ ID NO 237
<211> LENGTH: 21
<212> TYPE: DNA
<213> ORGANISM: Zea mays
```

```
<400> SEQUENCE: 237
cagccaagga tgacttgccg g                                              21

<210> SEQ ID NO 238
<211> LENGTH: 21
<212> TYPE: DNA
<213> ORGANISM: Zea mays

<400> SEQUENCE: 238
tagccaagga gactgcctat g                                              21

<210> SEQ ID NO 239
<211> LENGTH: 21
<212> TYPE: DNA
<213> ORGANISM: Zea mays

<400> SEQUENCE: 239
tagccaagga gactgcctac g                                              21

<210> SEQ ID NO 240
<211> LENGTH: 21
<212> TYPE: DNA
<213> ORGANISM: Zea mays

<400> SEQUENCE: 240
tagccaagga tgacttgcct a                                              21

<210> SEQ ID NO 241
<211> LENGTH: 21
<212> TYPE: DNA
<213> ORGANISM: Zea mays

<400> SEQUENCE: 241
tagccaagga tgacttgcct a                                              21

<210> SEQ ID NO 242
<211> LENGTH: 21
<212> TYPE: DNA
<213> ORGANISM: Zea mays

<400> SEQUENCE: 242
tagccaagga tgacttgcct a                                              21

<210> SEQ ID NO 243
<211> LENGTH: 21
<212> TYPE: DNA
<213> ORGANISM: Zea mays

<400> SEQUENCE: 243
tagccaagga tgacttgcct g                                              21

<210> SEQ ID NO 244
<211> LENGTH: 21
<212> TYPE: DNA
<213> ORGANISM: Zea mays

<400> SEQUENCE: 244
tagccaagga tgacttgcct g                                              21

<210> SEQ ID NO 245
<211> LENGTH: 21
<212> TYPE: DNA
<213> ORGANISM: Zea mays
```

<400> SEQUENCE: 245
tagccaagga tgacttgcct g                                              21

<210> SEQ ID NO 246
<211> LENGTH: 21
<212> TYPE: DNA
<213> ORGANISM: Zea mays

<400> SEQUENCE: 246
tagccaagga tgacttgcct a                                              21

<210> SEQ ID NO 247
<211> LENGTH: 21
<212> TYPE: DNA
<213> ORGANISM: Zea mays

<400> SEQUENCE: 247
tagccaagga tgacttgcct a                                              21

<210> SEQ ID NO 248
<211> LENGTH: 21
<212> TYPE: DNA
<213> ORGANISM: Zea mays

<400> SEQUENCE: 248
tagccaagga tgacttgccg g                                              21

<210> SEQ ID NO 249
<211> LENGTH: 21
<212> TYPE: DNA
<213> ORGANISM: Zea mays

<400> SEQUENCE: 249
tagccaagaa tgacttgcct a                                              21

<210> SEQ ID NO 250
<211> LENGTH: 21
<212> TYPE: DNA
<213> ORGANISM: Zea mays

<400> SEQUENCE: 250
tagccaagga tgacttgccg g                                              21

<210> SEQ ID NO 251
<211> LENGTH: 21
<212> TYPE: DNA
<213> ORGANISM: Zea mays

<400> SEQUENCE: 251
tagccaagaa tggcttgcct a                                              21

<210> SEQ ID NO 252
<211> LENGTH: 21
<212> TYPE: DNA
<213> ORGANISM: Zea mays

<400> SEQUENCE: 252
cagccaagga tgacttgccg g                                              21

<210> SEQ ID NO 253
<211> LENGTH: 21
<212> TYPE: DNA

```
<213> ORGANISM: Zea mays

<400> SEQUENCE: 253
cagccaagga tgacttgccg a                                          21

<210> SEQ ID NO 254
<211> LENGTH: 21
<212> TYPE: DNA
<213> ORGANISM: Zea mays

<400> SEQUENCE: 254
cagccaagga tgacttgccg a                                          21

<210> SEQ ID NO 255
<211> LENGTH: 21
<212> TYPE: DNA
<213> ORGANISM: Zea mays

<400> SEQUENCE: 255
cagccaagga tgacttgccg a                                          21

<210> SEQ ID NO 256
<211> LENGTH: 126
<212> TYPE: DNA
<213> ORGANISM: Arabidopsis lyrata

<400> SEQUENCE: 256
tcctggattt gaatgaacat cattgagtgc agcgttgatg taatttcctt ttttttcat   60 tgttgaatgg aattaaaaga atttacaccg gcgttgcgct caattatgtt tttcttattt  120
tcagga                                                          126

<210> SEQ ID NO 257
<211> LENGTH: 131
<212> TYPE: DNA
<213> ORGANISM: Arabidopsis lyrata

<400> SEQUENCE: 257
cctgggtttg aataaacatc attgagtgca gcgttgatgt aagtttactt attttattcc   60
attgttgaat gaattaaaat gatacagaat acatcagcgt tgcattcaat tatgtttttc  120
taattttcag g                                                    131

<210> SEQ ID NO 258
<211> LENGTH: 107
<212> TYPE: DNA
<213> ORGANISM: Arabidopsis thaliana

<400> SEQUENCE: 258
tgaatgaaca tcattgagtg cagcgttgat gtaatttcgt tttgttttc attgttgaat    60 ggattaaaag aatttatacc agcgttgcgc tcaattatgt ttttcta             107

<210> SEQ ID NO 259
<211> LENGTH: 109
<212> TYPE: DNA
<213> ORGANISM: Arabidopsis thaliana

<400> SEQUENCE: 259
tgaatgaaca tcattgagtg catcgttgat gtaatttac ttattttatt ccattgttga    60
attaattaaa gaagtatata tcagcgttgc attcaattat gttttcta            109
```

```
<210> SEQ ID NO 260
<211> LENGTH: 124
<212> TYPE: DNA
<213> ORGANISM: Brachypodium distachyon

<400> SEQUENCE: 260
gaagaggcgc aaaggcatca ttgagtgcag cgttgatgaa caggggccag gcgaccggcg    60
gccggtccgg ttcggttcac cggcgctgca cacagtgacg cccttgcatt ctctggcccg   120
attc                                                                124

<210> SEQ ID NO 261
<211> LENGTH: 124
<212> TYPE: DNA
<213> ORGANISM: Brachypodium distachyon

<400> SEQUENCE: 261
gaagaggcgc aaaggcatca ttgagtgcag cgttgatgaa caggggccag gcgaccggcg    60
gccggtccgg ttcggttcac cggcgctgca cacagtgacg cccttgcatt ctctggcccg   120
attc                                                                124

<210> SEQ ID NO 262
<211> LENGTH: 292
<212> TYPE: DNA
<213> ORGANISM: Brachypodium distachyon

<400> SEQUENCE: 262
gcgaagagga attagaagag gcgcaaaggc atcattgagt gcagcgttga tgaacagggg    60
ccaggcgacc ggcggccggt ccggttcggt tcaccggcgc tgcacacagt gacgcccttg   120
cattctctgg cccgattcat tgtgtgcga agaggaatta gaagaggcgc aaaggcatca   180
ttgagtgcag cgttgatgaa caggggccag gcgaccggcg gccggtccgg ttcggttcac   240
cggcgctgca cacagtgacg cccttgcatt ctctggcccg attcatttgt gt           292

<210> SEQ ID NO 263
<211> LENGTH: 96
<212> TYPE: DNA
<213> ORGANISM: Brassica napus

<400> SEQUENCE: 263
gaacatcatt gagtgcagcg ttgatgtgat ttacttatct ttttcattgt tgaatggatt    60
aaagcaattt acatcaacgt tggctcaatt atgttt                              96

<210> SEQ ID NO 264
<211> LENGTH: 156
<212> TYPE: DNA
<213> ORGANISM: Citrus sinensis

<400> SEQUENCE: 264
ccagattgaa aaaacatca ttgagtgcag cgttgatgaa tatttgtcgg tgctttgcca    60
atatttctct atactagcca ggattctttc accagcgctg cactcgatca tgttttttag   120
ctctgctggt tcaggattat ccagataata cgcaca                             156

<210> SEQ ID NO 265
<211> LENGTH: 79
<212> TYPE: DNA
<213> ORGANISM: Gossypium hirsutum

<400> SEQUENCE: 265
```

```
ttcattgagt gcagtgttga ttaggcgtag caagtaggtc ttgccgctgt ccactggcaa    60
tgagaaacct gcctgtgaa                                                 79

<210> SEQ ID NO 266
<211> LENGTH: 113
<212> TYPE: DNA
<213> ORGANISM: Hordeum vulgare

<400> SEQUENCE: 266
cgcagaggtg ccgttgagtg cagcgttgat gaaccgtccg gccatggccc gtccgcctcc    60
accgaggccg gagcggttca ccggcgctgc acgcaatgac gcctctgctt tct          113

<210> SEQ ID NO 267
<211> LENGTH: 114
<212> TYPE: DNA
<213> ORGANISM: Oryza sativa

<400> SEQUENCE: 267
atcaaatgca tcattgagtg cagcgttgat gaacaacggt aaccggtcca tgttgatgcg    60
catttggccg gtgatctgat catcatcagc gcttcactca atcatgcgtt tggc          114

<210> SEQ ID NO 268
<211> LENGTH: 114
<212> TYPE: DNA
<213> ORGANISM: Oryza sativa

<400> SEQUENCE: 268
atcaaatgca tcattgagtg cagcgttgat gaacaacggt aaccggtcca tgttgatgcg    60
catttggccg gtgatctgat catcatcagc gcttcactca atcatgcgtt tggc          114

<210> SEQ ID NO 269
<211> LENGTH: 118
<212> TYPE: DNA
<213> ORGANISM: Oryza sativa

<400> SEQUENCE: 269
agggaaggca ttattgagtg cagcgttgat gaacctgccg gccggctaaa ttaattagca    60
agaaagtctg aaactggctc aaaggttcac cagcactgca cccaatcacg cctttgct     118

<210> SEQ ID NO 270
<211> LENGTH: 118
<212> TYPE: DNA
<213> ORGANISM: Oryza sativa

<400> SEQUENCE: 270
agggaaggca ttattgagtg cagcgttgat gaacctgccg gccggctaaa ttaattagca    60
agaaagtctg aaactggctc aaaggttcac cagcactgca cccaatcacg cctttgct     118

<210> SEQ ID NO 271
<211> LENGTH: 134
<212> TYPE: DNA
<213> ORGANISM: Picea abies

<400> SEQUENCE: 271
agccgtggca accacatcat tgagtgcagc gttgacgata gaaattccac caatagattt    60
gataatatct atctatttgt ggaatgccat tgatattgtt aaccctgcac tcaatagtat   120
gtttgccaat ggct                                                    134
```

<210> SEQ ID NO 272
<211> LENGTH: 120
<212> TYPE: DNA
<213> ORGANISM: Populus trichocarpa

<400> SEQUENCE: 272

```
tggagaacca tcattgagtg cagcgttgat gaaatcctcc attttgtgct attaaactgt      60 taccaacccct ttatggggca tggcatcatt tcaccagcgc tgcattcaat catgtttttc    120
```

<210> SEQ ID NO 273
<211> LENGTH: 114
<212> TYPE: DNA
<213> ORGANISM: Populus trichocarpa

<400> SEQUENCE: 273

```
taattataca ccattgagtg cagcgttgat gaaattctct tgttagctta cttagctatt     60
ttctcacgat ggcgtggaat catttcacca gcgctgcatt caaccatgtt tttc          114
```

<210> SEQ ID NO 274
<211> LENGTH: 71
<212> TYPE: DNA
<213> ORGANISM: Populus trichocarpa

<400> SEQUENCE: 274

```
caagtttagt tcattgagtg gagctttgat gacaatttgt tttaaaagct ctactgtatt     60
cgaacaatat g                                                          71
```

<210> SEQ ID NO 275
<211> LENGTH: 157
<212> TYPE: DNA
<213> ORGANISM: Ricinus communis

<400> SEQUENCE: 275

```
aaacatcatt gagtgcagcg ttgatgaatt cccctacatg acatatttct gttggttaat     60
tcattaccaa tatcccttct ttaaaaaaag aagtaaacct ttttgggaat agatggtttt    120
ggatgatttc accagcgctg cattcaatca tgtttttt                            157
```

<210> SEQ ID NO 276
<211> LENGTH: 91
<212> TYPE: DNA
<213> ORGANISM: Sorghum bicolor

<400> SEQUENCE: 276

```
tcattgagtg cagcgttgat gagccagctg gccggccagc cgtgcgtccg ccgccggcgc     60
cggccacggc tcaccggcgc tgcactcaat t                                    91
```

<210> SEQ ID NO 277
<211> LENGTH: 116
<212> TYPE: DNA
<213> ORGANISM: Solanum lycopersicum

<400> SEQUENCE: 277

```
cagagtactt agaaacatga ttgagtgcag cgttgatgac atatttgaga agtcctgcat     60
ttgggccttc ctcattttc atcaacgcta aactcgatca tgttttaat tctctg          116
```

<210> SEQ ID NO 278
<211> LENGTH: 123
<212> TYPE: DNA
<213> ORGANISM: Theobroma cacao

```
<400> SEQUENCE: 278
attcccagat ggaagacaca tcattgagtg cagcgttgat gaattctttc acttttttgcc      60 aactctatct cagatgaatt cgccagcgct gcactcaatc atgtgttttg ctctttctgg     120
aaa                                                                   123

<210> SEQ ID NO 279
<211> LENGTH: 118
<212> TYPE: DNA
<213> ORGANISM: Vitis vinifera

<400> SEQUENCE: 279
gaagaaaaca tcattgagtg cagcgttgat gaaactgaag tattccattt ttcagcttct      60
ttgaagtccg gcaagatggg ttctggttga ttccattggc gctgcactca atcatgtc       118

<210> SEQ ID NO 280
<211> LENGTH: 118
<212> TYPE: DNA
<213> ORGANISM: Vitis vinifera

<400> SEQUENCE: 280
gaagaaaaca tcattgagtg cagcgttgat gaaactgaag tattccattt ttcagcttct      60
ttgaagtccg gcaagatggg ttctggttga ttccattggc gctgcactca atcatgtc       118

<210> SEQ ID NO 281
<211> LENGTH: 141
<212> TYPE: DNA
<213> ORGANISM: Zea mays

<400> SEQUENCE: 281
gtcattgagc gcagcgttga tgatgcggag catgtacgtc ttcccgggct tcactttcag      60
cttgaacgtg tctggtgcat gcatatcata agtatggata tgagttagta taaagaatca    120
tagccgttag cgctcattaa c                                                141

<210> SEQ ID NO 282
<211> LENGTH: 80
<212> TYPE: DNA
<213> ORGANISM: Zea mays

<400> SEQUENCE: 282
tcattgagcg cagcgttgat gagccagccg ccgtgcctcc cctgtcggct gcggcggctc      60
accagcgctg cactcaatta                                                  80

<210> SEQ ID NO 283
<211> LENGTH: 160
<212> TYPE: DNA
<213> ORGANISM: Brachypodium distachyon

<400> SEQUENCE: 283
tttggggttg ggattggggg ctggagcagc agcggtggaa ggggcatgca gaggagcagg      60
gatgatgggg ggttgtactc tgcttcttcc cctctcgttc tcctgtgcct gcctcttcca    120
ttcctgctgc taccgccgtg ctcggtgggc agggctgggc                            160

<210> SEQ ID NO 284
<211> LENGTH: 74
<212> TYPE: DNA
<213> ORGANISM: Medicago truncatula

<400> SEQUENCE: 284
```

```
tcttcccctc ccctataaac tctcaaacaa agtcttagac tttgtttgcg agtttgaagg      60
ggcagggaga ggag                                                        74
```

<210> SEQ ID NO 285
<211> LENGTH: 84
<212> TYPE: DNA
<213> ORGANISM: Sorghum bicolor

<400> SEQUENCE: 285

```
tggaaggggc atgcagagga gcacgaggct tggctggaag ccgacctacg cctcgctggc      60
tctcctgtgc ctgcctcttc catt                                             84
```

<210> SEQ ID NO 286
<211> LENGTH: 92
<212> TYPE: DNA
<213> ORGANISM: Saccharum spp.

<400> SEQUENCE: 286

```
tggaaggggc atgcagagga gcacgaggct tggctaaaag ccgacctgtg ctatgctacc      60
cctcgctggc tctcctgtgc ctgcctcttc ca                                    92
```

<210> SEQ ID NO 287
<211> LENGTH: 123
<212> TYPE: DNA
<213> ORGANISM: Zea mays

<400> SEQUENCE: 287

```
gtggaagggg catgcagagg aggagcacga gcgaggtgtg gctggaagaa gcagccgggg      60
cctgtgtgct atatacccct cgcaagctct cctcactcct ctcctgtgcc tgcctcttcc     120
att                                                                   123
```

<210> SEQ ID NO 288
<211> LENGTH: 78
<212> TYPE: DNA
<213> ORGANISM: Zea mays

<400> SEQUENCE: 288

```
gtggaagggg catgcagagg agcacgaacg aggtgtggtt ggcccctcgt tagctctcct      60
gtgcctgcct cttccatt                                                    78
```

<210> SEQ ID NO 289
<211> LENGTH: 263
<212> TYPE: DNA
<213> ORGANISM: Arabidopsis lyrata

<400> SEQUENCE: 289

```
aacgcgtatg tgacgaaagt agtgtgcagc caaggatgac ttgccgattt aaatgatctt      60
tctttatact ctattaagac attttaagtt tcaaatttct ttggttcttc aaggattaag    120
gaagaaagta ggctatatat gtagatatat atattatgct gtattaaata tatgtacaag    180
ataagaccaa aaaagaaaaa gtaacaatca tgatcggcaa gttgtccttg gctacacgtt    240
actttgtgtc gcgcataggt gtt                                            263
```

<210> SEQ ID NO 290
<211> LENGTH: 173
<212> TYPE: DNA
<213> ORGANISM: Arabidopsis lyrata

<400> SEQUENCE: 290
gtgcccaacg gagtagaatt gcatgaagtg gagtagagta taatgcagcc aaggatgact    60
tgccggaacg ttgttaatca tacgtataaa ttatgtgatg aacatatttc tggcaagttg   120
tccttcggct acattttgct ctcttcttct catgcaaact ctctttggga tat          173

<210> SEQ ID NO 291
<211> LENGTH: 292
<212> TYPE: DNA
<213> ORGANISM: Arabidopsis lyrata

<400> SEQUENCE: 291
gtctcatcta aagccttgaa tgtgggaaaa aggccattgt tgttcagcca aggatgactt    60
gccggtagct ttgtatattt actctatatt cggtttatat tatggagatt atgctttata   120
tatatatata catagtttta attgattttt tttcgtacgt acgtaatcta atacgaaaaa   180
gtatttactt atttatatgt gtgttggtga gatgtgtaaa caaagcaagc ccggcaagtc   240
atctctggct atgcaactgc ctcttcctct cattctaggc ttacgatgac ac           292

<210> SEQ ID NO 292
<211> LENGTH: 155
<212> TYPE: DNA
<213> ORGANISM: Arabidopsis lyrata

<400> SEQUENCE: 292
gtatctttga gtcttacatg gaaaaaatag agaatgagat tgagccaagg atgacttgcc    60
gatttttatc aacaaatctt aactgattat ggtgcccggc aagttgacct tggctctgtt   120
tccttctctt cttttcgatg tcaaactcta gatat                              155

<210> SEQ ID NO 293
<211> LENGTH: 174
<212> TYPE: DNA
<213> ORGANISM: Arabidopsis lyrata

<400> SEQUENCE: 293
gtcactaatt gtatcataga gtcttgcatg gaaaaaatag agaatgagat tgagccaagg    60
atgacttgcc gaatttatta acaaatctca aatgattatg gtgcccggca agttgacctt   120
ggctctgttt ccttctcttc ttttcgatgt caaactctag atatatcaat cgat         174

<210> SEQ ID NO 294
<211> LENGTH: 184
<212> TYPE: DNA
<213> ORGANISM: Arabidopsis lyrata

<400> SEQUENCE: 294
tgtatcagag ggtcttgcat gaaggaataa agaatggaat tgagccaagg atgacttgcc    60
ggtttaaaca caaccggatt atgaccattg atttggtctc attcacaatc tgttgattcg   120
tgtctggcaa gttgaccttg gctctgcttc gttctctatt cttccatgtt agattccaga   180
tata                                                                184

<210> SEQ ID NO 295
<211> LENGTH: 202
<212> TYPE: DNA
<213> ORGANISM: Arabidopsis lyrata

<400> SEQUENCE: 295
atgatgatga tgagtctcta gttgtatcag agggtcttgc atggaagagt agagaatgag    60

```
gttgagccaa ggatgacttg ccgggttttt taccaatgaa tcttaactga ttttggtgtc    120
cggcaagttg accttggctc tgtttccttc tcttcttttc gatgtcagac tccgcgatat    180
atatctattt catcatcgtc at                                              202
```

<210> SEQ ID NO 296
<211> LENGTH: 205
<212> TYPE: DNA
<213> ORGANISM: Arabidopsis lyrata

<400> SEQUENCE: 296

```
tagaaaatca tataagagaa aatggtgaca tgaagaatga gaacttgtgt ggtagccaag     60
gatgacttgc ctgcgtttta acaatacaat atcaaagact actcgatcga tcgatagtct    120
tagagttggt tagtcgtcag gcagtctcct tggctattca acaattctt gttctcctca    180 tttcacatct ctctttcgtt ttttg                                           205
```

<210> SEQ ID NO 297
<211> LENGTH: 210
<212> TYPE: DNA
<213> ORGANISM: Arabidopsis lyrata

<400> SEQUENCE: 297

```
gaaggagatg tcaaagatga gtaggagaat catatttggt agccaaggat gacttgcctg     60
attcctttgc gtaaaatggt tagtgtcatg tttgacaaag tgactatcaa ttacatcaag    120
cgatgaccat tttgcttata aaaagatgt caggcagtct ccttggatat ccttatatgt    180
tcttctcttt catctcagac attcatcttc                                      210
```

<210> SEQ ID NO 298
<211> LENGTH: 300
<212> TYPE: DNA
<213> ORGANISM: Arabidopsis lyrata

<400> SEQUENCE: 298

```
gaatgaggca aaacatattg agtaatggag tgtataatga ggaagagagg tctaacatgg     60
cgaaaagagt catgtttaat agccaaggat gacttgcctg atcttttca cctccatgat    120 tcaatttgaa gttcatgcgt tttggattat tatgcatcta aaaggtataa taattcgaaa    180
atcatgttga atcatgcggg ttaggtttca ggcagtctcc ttggctatct tgacatgctt    240
ttttcatcca tgttataccct gttttttcttt ctgtctctaa agtcactatt aagtctcttc    300
```

<210> SEQ ID NO 299
<211> LENGTH: 203
<212> TYPE: DNA
<213> ORGANISM: Arabidopsis lyrata

<400> SEQUENCE: 299

```
gaaggagatg tcaaagatga ataagagaac cacatttggt agccaaggat gacttgcctg     60
tttctttgaa caaatggtt ggtgtcatgt ttgatgtgac tacaagttat atcaagaatg    120 acatttttgct tataaaaaga catcaggcag tctccttggc tatccttata tgttcttctt    180
tctcatctca gacatttacc ttc                                            203
```

<210> SEQ ID NO 300
<211> LENGTH: 272
<212> TYPE: DNA
<213> ORGANISM: Arabidopsis lyrata

<400> SEQUENCE: 300

```
gttaagaaat gtatgatgaa gatgagaggt ctaacatggc gaaaagagtc atgtttaata      60
gccaaggatg acttgcctga tcttttcac ctccatgatt caatttgaat ttcatgggtt     120
ttggattatt atgcatctaa aaggtgtaat aattcgaaaa tcaagttgaa tcttgcgggt    180
taggtttcag gcagtctcct tggctatctt gacatactct tttcatccat gttataccta   240
attttctttt tttattgagg atatttgagg at                                   272
```

<210> SEQ ID NO 301
<211> LENGTH: 230
<212> TYPE: DNA
<213> ORGANISM: Arabidopsis lyrata

<400> SEQUENCE: 301

```
tcattattta gaaggaaatg tcaaagatga ataggagaat catatttggt agccaaggat      60
gacttgcctg tttctttgag taaaatggtt attgtcatgt ttgacaagtg actataagtt   120
atatcaagta acgaccattt tactcatcaa aagacatgag gcagtcttct tggctatcct   180
tatatgttct tctgtctcat ctcagacgtt aaccttcatc taaaataaga                230
```

<210> SEQ ID NO 302
<211> LENGTH: 252
<212> TYPE: DNA
<213> ORGANISM: Arabidopsis lyrata

<400> SEQUENCE: 302

```
gaagtgtata acgaggaaaa gaggtctaac atggcgaaaa gagtcatgtt tagtagccaa      60
agatgacttg cctgatcttt ttcacctcca tgattcaatt tgaattccat gggttttgga    120
ttattatgca ttttaaaagc ataatagttc gaaaatcatg ttgaatcttg cgggttaggt    180
ttcaggcagt ctctttggct atcttgacat gctttttca ttcatgttat acctattttt    240
ctttctgtct tc                                                         252
```

<210> SEQ ID NO 303
<211> LENGTH: 100
<212> TYPE: DNA
<213> ORGANISM: Antirrhinum majus

<400> SEQUENCE: 303

```
aggttacgag gtatagccaa ggatgacttg ccgacgaaag taagtacatt catgtatttt      60
gtaaggtcgg caagttatct ttggctacat ctctacctaa                          100
```

<210> SEQ ID NO 304
<211> LENGTH: 158
<212> TYPE: DNA
<213> ORGANISM: Aquilegia coerulea

<400> SEQUENCE: 304

```
gcatgaaagt aggaggcgtg tttagtagcc aaggatgact tgcctaccaa gggtctcatt      60
ttaaggcatt atcttccttg gataatgcgt ctggaatcct cgactggtta ataggcagtc    120
tccttggcca acttgactgc ctcctattac tcatgcta                             158
```

<210> SEQ ID NO 305
<211> LENGTH: 180
<212> TYPE: DNA
<213> ORGANISM: Aquilegia coerulea

<400> SEQUENCE: 305

```
tagccaagga tgacttgcct gtatcctctt agaggccggc ctgcgcgcct gtctctatat      60
tatcatacat tggaatatat catccttgtg tggttaatag gcgggcctgc ctgtctctat     120
attatcatac attggaatat atcatccttg tgtggttaat aggcagtctc cttggctaac    180
```

<210> SEQ ID NO 306
<211> LENGTH: 111
<212> TYPE: DNA
<213> ORGANISM: Aquilegia coerulea

<400> SEQUENCE: 306

```
aatgcagcca aggatgactt gccggaacgt tgttaaccat gcatatgaat aatgtgatga     60
ttaattatgt gatgaacata tttctggcaa gttgtccttc ggctacattt t             111
```

<210> SEQ ID NO 307
<211> LENGTH: 144
<212> TYPE: DNA
<213> ORGANISM: Aegilops taushii

<400> SEQUENCE: 307

```
gagtggtatc atcttttagc tcttgcatgt ggggaggagg acatgtagcc aaggatgaat     60
tgccagcgcg gagtgatccg tcgcgcaggc aagtcattac tggctacgtg tttgcctcgt    120
ttcctcatgc tggagcgaag atgt                                           144
```

<210> SEQ ID NO 308
<211> LENGTH: 226
<212> TYPE: DNA
<213> ORGANISM: Arabidopsis thaliana

<400> SEQUENCE: 308

```
gtgacgaaag tagtgtgcag ccaaggatga cttgccgatt taaatgatct ttctttatac     60
tctattaaga caatttagtt tcaaactttt ttttttttt tttttttgaag gattcaggaa    120 gaaattagga tatattattc cgtataaaat acaagatata taaaaccaaa aagaaaaagt    180
aacatgatcg gcaagttgtc cttggctaca cgttactttg tgtcgc                   226
```

<210> SEQ ID NO 309
<211> LENGTH: 181
<212> TYPE: DNA
<213> ORGANISM: Arabidopsis thaliana

<400> SEQUENCE: 309

```
cccaacggag tagaattgca tgaagtggag tagagtataa tgcagccaag gatgacttgc     60
cggaacgttg ttaaccatgc atatgaataa tgtgatgatt aattatgtga tgaacatatt    120
tctggcaagt tgtccttcgg ctacattttg ctctcttctt ctcatgcaaa ctttccttgg    180
g                                                                    181
```

<210> SEQ ID NO 310
<211> LENGTH: 411
<212> TYPE: DNA
<213> ORGANISM: Arabidopsis thaliana

<400> SEQUENCE: 310

```
tcgtccatta tgagtattaa ttatggttag ggaatcttac agaatgaaaa tgaaggtgtg     60
aatggattgt ctcatctaaa gccttgaatg tgggaaaaag gccattgttg ttcagccaag    120
gatgacttgc cggtagcttg tattatgatt actctatatt cgatttatat tatggagatg    180
```

```
atggtttata tatatttact tatctacata gttttagttg attttttttc gtacgtaata      240
taatacgaaa aagtatttac ttatttatat atgtgtgttg gggcaagaag tgtaaccaag      300
ctagcccggc aagtcatcta tggctatgca actgtctctt cctctcattc taggcttacg      360
atgacacgta aaaatccca aatatcacta atatgatatg aatatggatg a               411
```

<210> SEQ ID NO 311
<211> LENGTH: 154
<212> TYPE: DNA
<213> ORGANISM: Arabidopsis thaliana

<400> SEQUENCE: 311

```
gtatcataga gtcttgcatg gaaaaattaa agaatgagat tgagccaagg atgacttgcc       60
gatgttatca acaaatctta actgattttg gtgtccggca agttgacctt ggctctgttt      120
ccttcttttc ttttcaatgt caaactctag atat                                  154
```

<210> SEQ ID NO 312
<211> LENGTH: 217
<212> TYPE: DNA
<213> ORGANISM: Arabidopsis thaliana

<400> SEQUENCE: 312

```
tgatgatgat gatgagtcac taattaattg tatcatagag tcttgcatgg aaaaatagaa       60
aatgagattg agccaaggat gacttgccga ttttctcaac gaatcttact gattatggta      120
tccggcaagt tgactttggc tctgtttcct tcccttcttt tcgatgtcaa actctagata      180
cctaaccaca tatcatatat atcatcatca ttcatca                              217
```

<210> SEQ ID NO 313
<211> LENGTH: 167
<212> TYPE: DNA
<213> ORGANISM: Arabidopsis thaliana

<400> SEQUENCE: 313

```
gggtcttgca tgaaggaata acgaatggaa ttgagccaag gatgacttgc cggtttaaac       60
ccaaccggtt tatgaccatt gatttggtct cattcacaat ctgttgattc gtgtctggca      120
agttgacctt ggctctgctt cgttctctat tcttccatgt tagattc                   167
```

<210> SEQ ID NO 314
<211> LENGTH: 379
<212> TYPE: DNA
<213> ORGANISM: Arabidopsis thaliana

<400> SEQUENCE: 314

```
tgcctataaa taccttcatc acgagtatga caagatcaca agacaagaaa agaaaggtag       60
agaaaacatg ataatgatga ttacgatgat gagagtctct agttgtatca gagggtcttg      120
catggaagaa tagagaatga ggttgagcca aggatgactt gccgggtttt tttaccaatg      180
aatctaatta actgattctg gtgtccggca agttgacctt ggctctgttt ccttctcttc      240
ttttggatgt cagactccaa gatatctatc atcatgaatc gtgatcaaac tttgtaattt      300
cattgaaatg tgttttttctt gatgcgaatt ttttggctta cggttttttcg atttgaatga      360 tcagattttt gttttttgca                                                  379
```

<210> SEQ ID NO 315
<211> LENGTH: 190
<212> TYPE: DNA
<213> ORGANISM: Arabidopsis thaliana

<400> SEQUENCE: 315

```
tcatataaga gaaaatggtg acatgaagaa tgagaacttg tgtggtagcc aaggatgact    60
tgcctgcgtt ttagaccata tatcaaag actcactcga tcgatagtct tagagttggt    120
tggtcgtcag gcagtctcct tggctattca acaattctc attctcttca ttcacatttc    180
tctttttgg                                                           190
```

<210> SEQ ID NO 316
<211> LENGTH: 206
<212> TYPE: DNA
<213> ORGANISM: Arabidopsis thaliana

<400> SEQUENCE: 316

```
gaaggagatg tcaaagatga atagaagaat catatttggt agccaaggat gacttgcctg    60
actctttgtg taaaatgttt agtgtcttgt ttgaagtcac tataagttgt atcaagcaat   120
gaccattttg cttataaaaa agatatcagg cagtctcctt ggctatcctt atatgttctt   180
ctctttcatc tcagacattc accttc                                        206
```

<210> SEQ ID NO 317
<211> LENGTH: 221
<212> TYPE: DNA
<213> ORGANISM: Arabidopsis thaliana

<400> SEQUENCE: 317

```
gagtataatg aggaagagag gtctaacatg gcgaaaagag tcatgtttag tagccaagga    60
tgacttgcct gatcttttc acctccatga ttcaatttgt aattcatggg ttttggatta   120
ttatacattc aaaagtataa taatttgaaa tcatgttgaa tcttgcgggt taggtttcag   180
gcagtctcct tggctatctt gacatgcttt tttcattcac g                       221
```

<210> SEQ ID NO 318
<211> LENGTH: 213
<212> TYPE: DNA
<213> ORGANISM: Arabidopsis thaliana

<400> SEQUENCE: 318

```
ttagaaggag atgtcaaaga tgaataggag aacaatattt ggtagccaag gatgacttgc    60
ctgcttctct gaacaaaatg gtcgatgtca tgttttgaag tgactataag ttataccaag   120
aaatgaccat tttgtttata aatagacatc aggcagtctc cttggctatc cttatatgtt   180
cttctttctc aactcagata tttaccttca tcc                                213
```

<210> SEQ ID NO 319
<211> LENGTH: 211
<212> TYPE: DNA
<213> ORGANISM: Arabidopsis thaliana

<400> SEQUENCE: 319

```
atgaagaaga gaggtctaat atggcgaaaa gagtcatgtt taatagccaa ggatgacttg    60
cctgatcttt ttcacctcca tgattcaatt ttaagttcgt ggattttgga ttattatgcg   120
tttaaaaggt ataataattt gagatcatgt tgaatcttgc gggttaggtt tcaggcagtc   180
tctttggcta tcttgacatg ctttcttcat c                                  211
```

<210> SEQ ID NO 320
<211> LENGTH: 212
<212> TYPE: DNA

<213> ORGANISM: Arabidopsis thaliana

<400> SEQUENCE: 320

```
tagaaggaga agtcaaagat gaatagaaga atcatatttg gtagccaagg atgacttgcc      60
tgtttctttg agtaaaatgg gttagtgtca tgtttgacaa gtgactataa gttatatcaa     120
gcaatgacca ttttactcat caaaagacat caggcagtct ccttggctat ccttatatgt     180
tcttctctct catctcagac gtttaccttc at                                    212
```

<210> SEQ ID NO 321
<211> LENGTH: 215
<212> TYPE: DNA
<213> ORGANISM: Arabidopsis thaliana

<400> SEQUENCE: 321

```
gatgaagaag agaggtctaa catggcggaa agcgtcatgt ttagtagcca aggatgactt      60
gcctgatctt tttcgcctcc acgattcaat ttcaaattca tgcattttgg attattatac     120
cttttaaagt ataataggtc aaatatcatg ttgaatcttg cgggttaggt ttcaggcagt     180
ctctttggct atcttgacat gcttttttcca tccat                               215
```

<210> SEQ ID NO 322
<211> LENGTH: 121
<212> TYPE: DNA
<213> ORGANISM: Brachypodium distachyon

<400> SEQUENCE: 322

```
gcagagaagg ggatgcagcc aaggatgact tgccgactcc tggtgttggg ggaattgcag      60
ctttgttgag ccttgagtta gccggcaggt tgtccttggc tacacctagt tctcttcttc     120
t                                                                     121
```

<210> SEQ ID NO 323
<211> LENGTH: 106
<212> TYPE: DNA
<213> ORGANISM: Brachypodium distachyon

<400> SEQUENCE: 323

```
gagatagaga gtggaatgta gccaaggatg acttgccggg tatgtgcatg tacgcttcag      60
ggaattatat gcatccctgg tctgaatcca tgctgatatt tcccgg                    106
```

<210> SEQ ID NO 324
<211> LENGTH: 151
<212> TYPE: DNA
<213> ORGANISM: Brachypodium distachyon

<400> SEQUENCE: 324

```
ttgccatacg ctaagaggca gagaagggga tgcagccaag gatgacttgc cggctcctgg      60
tgttggggga attgcagctt tgttgagcct tgagttagcc ggcaggttgt ccttggctac     120
acctagttct cttcttctgg tgtttggccc t                                    151
```

<210> SEQ ID NO 325
<211> LENGTH: 187
<212> TYPE: DNA
<213> ORGANISM: Brachypodium distachyon

<400> SEQUENCE: 325

```
atggagatgg agagcctccc ttgatttttgg tagccaagaa tgacttgcct atgcttgccc      60
tctgctaacc agctagccat gcatggtaac caatggacaa atttcttgtg gttggcgtgg     120
```

```
ttagtgtggt tgcatgggtg ggtcttcttg gctagccaga gcggctctca tccaccatgc    180
caggcca                                                              187

<210> SEQ ID NO 326
<211> LENGTH: 164
<212> TYPE: DNA
<213> ORGANISM: Brachypodium distachyon

<400> SEQUENCE: 326
ccttacatgg tgataagggg tttggccctg atagccaagg atgacttgcc tgtgcatgtc    60
ctcccttgat cgcttgcata atttcatata tgcatgtgat ctcgatttat cacaggcagt    120
ctccttggct agcctgggtg cctcttatcc tccatgctag gcct                    164

<210> SEQ ID NO 327
<211> LENGTH: 151
<212> TYPE: DNA
<213> ORGANISM: Brachypodium distachyon

<400> SEQUENCE: 327
gggccatgca ggacgaggca cagagcagga tgcagccaag gatgacttgc cggccggctg    60
gccggcaatg tcgccgccgg cgtgacatga tgcttgcccg gcaagtttgt ccttggctac    120
accttgctct ctgcccatca tgtgttgccc t                                   151

<210> SEQ ID NO 328
<211> LENGTH: 181
<212> TYPE: DNA
<213> ORGANISM: Brachypodium distachyon

<400> SEQUENCE: 328
ggtgttgcgt gggcagagaa gaagccttac atggcagcaa ggggcttatc tctgatagcc    60
aaggatgact tgcctgtgtc atacttcaag gcttggcaac atgatgcatg agcctttgtt    120
gtagtctcat aggcagtctc cttggctagc ctgagtggct cttgcggctc atgccaggct    180
g                                                                    181

<210> SEQ ID NO 329
<211> LENGTH: 164
<212> TYPE: DNA
<213> ORGANISM: Brachypodium distachyon

<400> SEQUENCE: 329
cttgcatgag ggccagagcc tgcttcctcc ggtagccaag gatgacttgc ctatatttgc    60
tccttcagaa gtcctggtta attacatgcc aggtttcaga tgagtttggc gataggcagt    120
caccttggct agcctgagtg gctcttgcct cttatggaag gcct                    164

<210> SEQ ID NO 330
<211> LENGTH: 175
<212> TYPE: DNA
<213> ORGANISM: Brachypodium distachyon

<400> SEQUENCE: 330
tggagacgag gagccccttt gcaggctcta ccagccaaga atggcttgcc tatgcccacg    60
ttctgtttca tcaccactgg gcttaatctt ggagccctgg tgatggatga gatgtgattg    120
tatggtcaag ccatcttggc tagaagagag atcctcgtcc cccatgctag gctgc        175

<210> SEQ ID NO 331
```

<211> LENGTH: 183
<212> TYPE: DNA
<213> ORGANISM: Brachypodium distachyon

<400> SEQUENCE: 331

```
cttacatgga gataaggagc ctacctctgt tagccaggaa tggcttgcct acgcacacat      60
ttttcggttc atcacagggg caaaactaac ttggagatag cccctagtat gatggacgga     120
gtgtggctgc atggtcaagc cttcctgact aggagagtgc tcctcatccc ccatgctagg     180
ctg                                                                   183
```

<210> SEQ ID NO 332
<211> LENGTH: 174
<212> TYPE: DNA
<213> ORGANISM: Brachypodium distachyon

<400> SEQUENCE: 332

```
tctttgcatg gaagtaggag gccatctttg atagccaagg atgatttgcc tgtaaaaccg      60
attgtcgtcg cctctcggtg ccgttccagg cactcgaagg gagggcggca gcaacaggtt     120
ctatgggcaa gtcagcctgg ctacccgagt acctcttacc catattccat gcca           174
```

<210> SEQ ID NO 333
<211> LENGTH: 132
<212> TYPE: DNA
<213> ORGANISM: Brassica napus

<400> SEQUENCE: 333

```
tgtgaccaaa gtagtgtgca gccaaggatg acttgccgat ttaaaatatc tgataagtat      60
tttatttcgt attttaaaga aaaaaatcat gatcggcaag ttgtccttgg ctatacgttt     120
ctttgtgtcg cg                                                         132
```

<210> SEQ ID NO 334
<211> LENGTH: 188
<212> TYPE: DNA
<213> ORGANISM: Brassica napus

<400> SEQUENCE: 334

```
gtgaccaaag tagtgtgcag ccaaggatga cttgccgatt tgaaatatat ttttaatact      60
ttactaagac atcttttcag tttcaaattt gtcttggaga ggctaggaag aaattacaat     120
ttatttcgta gtttaaagaa aaaatatgat cggcaagttt ccttggcta catgtttctt     180
tgtgtcgc                                                              188
```

<210> SEQ ID NO 335
<211> LENGTH: 176
<212> TYPE: DNA
<213> ORGANISM: Brassica napus

<400> SEQUENCE: 335

```
agatgaatag aagaatcata tttggtagcc aaggatgact tgcctatttc ttgagagtaa      60
aatgggcatg gtgtcatgtt aaaagttact gtaggtagtt tcaatttgac cattttcctt     120
acaaatgata ttaggcagtc tccttggcta tccttatatg ttcttctctc tcatct         176
```

<210> SEQ ID NO 336
<211> LENGTH: 220
<212> TYPE: DNA
<213> ORGANISM: Brassica napus

<400> SEQUENCE: 336

```
gaaggagatg tcaaagatga ataggagatt tctatttggt agccaaggat gacttgccta    60
cttctttgcg aaggaaaatg gtcacggtgt catgtttgaa agtgaatata catttttaag   120
agtatatcaa ttagtgacca ttttgcgtat aaaaagatat taggcagtct ccttggctat   180
ccttatatgt tcttctttct catctcagac atttaccttc                         220
```

<210> SEQ ID NO 337
<211> LENGTH: 276
<212> TYPE: DNA
<213> ORGANISM: Brassica napus

<400> SEQUENCE: 337

```
gtttcaggca gtctccttgg ctatcttgac atgcttttt cttccatgtt ataccttctt    60
tctttgtatt tttcgaatcc aaataatatt tttttctata aatttactac gaaaatcctt   120
taaacaatct ctaacaaagt atgttattag aaaactacca cttttgcat ttattacaaa   180 tgcatgtacg tggtgagtgt atgcattctt tagaaggaaa tgtcaaaggt gaatagaaga   240
tcatatttgg tagccaagga tgacttgcct atttct                             276
```

<210> SEQ ID NO 338
<211> LENGTH: 201
<212> TYPE: DNA
<213> ORGANISM: Brassica napus

<400> SEQUENCE: 338

```
gtcaaagatg aataggagaa ttctatttgg tagccaagga tgacttgcct acttctttgc    60
gaaggaaaat ggtcacggtg tcatgtttga aagtgaatat atatttataa gagtatatca   120
attagtgacc attttgcgta taaaaagata ttaggcagtc ccttggcta tccttatatg   180 ttcttctttc tcatctcaga c                                             201
```

<210> SEQ ID NO 339
<211> LENGTH: 168
<212> TYPE: DNA
<213> ORGANISM: Brassica napus

<400> SEQUENCE: 339

```
gagaaacggt gacatgaaga atgagaagtt gtgtggtagc caaggatgac ttgcctgcgt    60
ctttaacacc atatcaaaga ctttatcgat agtctctgag ttggttaggc tgtaggcagt   120
ctccttggct attcagacac tcctctttct cctcatttca catttctc                168
```

<210> SEQ ID NO 340
<211> LENGTH: 176
<212> TYPE: DNA
<213> ORGANISM: Brassica napus

<400> SEQUENCE: 340

```
gagaaatggt gacatgaaga atgagaagtt gtgtggtagc caaggatgac ttgcctgcgt    60
cttagaccat atctatcaaa gactaaaaga ttgatagtct tcgatgaatt ggttaatcgg   120
taggcagtct cctcggctat tcagacagtt ctctttctcc tcatttcaca tttctc       176
```

<210> SEQ ID NO 341
<211> LENGTH: 174
<212> TYPE: DNA
<213> ORGANISM: Brassica napus

<400> SEQUENCE: 341

```
agagtcatgt ttagtagcca aggatgactt gcctgctctt tttcacctcc atgattcaat      60
tttatgtaca gttttggatt actatgcttc taaagagtat agtaattcaa atcttgttg      120 aatctttgag ggtaacagtt tcaggcagtc tccttggcta tcttgacatg cttt           174
```

<210> SEQ ID NO 342
<211> LENGTH: 167
<212> TYPE: DNA
<213> ORGANISM: Brassica napus

<400> SEQUENCE: 342

```
gtgtttagta gccaaggatg acttgcctgc tcttgttcac ctccacgatt caactttata     60
cgttgaaggg ttttggatta ttgtgcattc aacatgtata ataatttgaa atcatgttga    120
atctttgtgg gttaggtttc aggcagtctc cttggctatt ttgacat                  167
```

<210> SEQ ID NO 343
<211> LENGTH: 155
<212> TYPE: DNA
<213> ORGANISM: Brassica napus

<400> SEQUENCE: 343

```
aaacggtgac atgaagaatg agaagttgtg tggtagccaa ggatgacttg cctgcgtctt     60
aacaccatat cacagacttt atcgatagtc tctgagttgg ttaggctgta ggcagtctcc    120
tcggctattc agacactcct ctttctcctc atttc                               155
```

<210> SEQ ID NO 344
<211> LENGTH: 199
<212> TYPE: DNA
<213> ORGANISM: Brassica napus

<400> SEQUENCE: 344

```
catggcgaaa agagtcgtgt ttagtagcca aggatgactt gcctgctctt gttcacctcc     60
acgattcaac tttatacgtt gaagggtttt ggattattgt gcattcaaca tgtataataa    120
tttgaaatca tgttgaatct tgtgggtta ggtttcaggc agtctccttg ctatttttga     180
catacttttt tcatccatg                                                 199
```

<210> SEQ ID NO 345
<211> LENGTH: 163
<212> TYPE: DNA
<213> ORGANISM: Brassica napus

<400> SEQUENCE: 345

```
tatatgtatc agagagtcat gcatgggaaa atagagaatg ataatgagcc aaagatgact     60
tgccgatttt accaaagaat ttaaaactga taatggtgac tggcaagtcg actttggctc    120
tgtttccttc tcttctttc gatgtaagac tctagatatc tat                       163
```

<210> SEQ ID NO 346
<211> LENGTH: 755
<212> TYPE: DNA
<213> ORGANISM: Citrus sinensis

<400> SEQUENCE: 346

```
atcaagtgct acctatatata cagaatagaa agaataacaa aggttggaaa ttggtctagg     60
gtttcttata tgaagggata aatagaggat ctagagccaa gaatgacttg ccgacggcat    120
tgaccataat atcatacggc aggccattct tgtctcaact ccgctctcta tcttctcatc    180
tgagactctc ggacactgac aaccaacctc agcaatgcag caccagatga ttctttctat    240
```

```
tctcaggtga tctatgatac tatgctcatc taatgagctc tgcgtcacat ttttattttt      300
cccccatttt tctgacttct cctccttgag ccattttttcc agatccatga acagtacaaa     360
atctctatta caaccaacag agttaagcaa tgctgttctt aatcataagc ttattttagg      420
gtggcatata ttttgcaata atctagttag aaataattaa aagttttttc ttggagcttt      480
ggcgtttctc ctggcatttg tacaaccttt tatgcaaaca gttgtagaat tggggatgac      540
acaatctttg gttggagtgt gattttatgc tgtatttatt atgcacacaa tagcaggctc      600
gtcgatcctc tgttcatgca agaactagag cgaaggaata gatagcttga ttatcgaaca      660
aattaaaata attaatcgtg catcaatttt gacaaggagt gaggaacctc tcctcatctg      720
cattatcatg aaattttaat aattttgtac atatc                                 755
```

```
<210> SEQ ID NO 347
<211> LENGTH: 150
<212> TYPE: DNA
<213> ORGANISM: Festuca arundinacea

<400> SEQUENCE: 347
ggcacgaggg caaagcctta catggctgca agggccttac ctctgatagc caaggatgac       60
ttgcctatgt cttcttcctc cctcagatgc ctaattagcc ttggaggtgt ggggtctcat      120
gggcagtcac cttggctagc ctgagtggct                                        150

<210> SEQ ID NO 348
<211> LENGTH: 189
<212> TYPE: DNA
<213> ORGANISM: Gossypium herbaceum

<400> SEQUENCE: 348
tatagagagg aagaaaaggt ctaacatgaa gataaagagt cttgtttggt agccaaggat       60
gacttgcctg cacctaatgt ccacgaggtt ttaatacatc aaaaaccctg gttgggtccc      120
aggcagtcac cttggctaac tagacaggct gttttcattc atgctaggcc tcatcttccg      180
ccccattgg                                                               189

<210> SEQ ID NO 349
<211> LENGTH: 121
<212> TYPE: DNA
<213> ORGANISM: Glycine max

<400> SEQUENCE: 349
aagaggaaga gagagtgatg cagccaagga tgacttgccg gcgttattat ttgctcatgt       60
tcatgctcac cggtttcctt gccggcaagt tgtgtttggc tatgttttgc tctcttcttc      120
t                                                                       121

<210> SEQ ID NO 350
<211> LENGTH: 183
<212> TYPE: DNA
<213> ORGANISM: Glycine max

<400> SEQUENCE: 350
tatgatgctg cagccaagga tgacttgccg ataaattctt tctctaattt gactttcaat       60
tcatgtttgt caattgatag tgcattagtt ctaatatatg catttgatta tatagaacac      120
tattgtgaaa gtgtctttag ggatagggta aattcggcaa gtcatctttg gctacatgtc      180
tat                                                                     183
```

<210> SEQ ID NO 351
<211> LENGTH: 115
<212> TYPE: DNA
<213> ORGANISM: Glycine max

<400> SEQUENCE: 351
aagtgggatg aagccaagga tgacttgccg acattaattt gccattaagc taacgagtta    60
ggtagaatca tttgttagat tttcccggca ggtcatcctc tggctatatt tggct         115

<210> SEQ ID NO 352
<211> LENGTH: 88
<212> TYPE: DNA
<213> ORGANISM: Glycine max

<400> SEQUENCE: 352
agattagtgg atgtgagcca aggatgactt gccggttgta aatagcacc cggtttaagt    60 ccttcttggt tcttatttac tattctta                                       88

<210> SEQ ID NO 353
<211> LENGTH: 120
<212> TYPE: DNA
<213> ORGANISM: Glycine max

<400> SEQUENCE: 353
gtcttgcatg aagaggtaga gagagtgctt ttgagccaag gatgacttgc cggcgtaatt    60
acgggtattg ccagcgagac atccttgttc acttatgctc tcttttcact catataagac   120

<210> SEQ ID NO 354
<211> LENGTH: 111
<212> TYPE: DNA
<213> ORGANISM: Glycine max

<400> SEQUENCE: 354
cagccaagga tgacttgccg gcattagcca agtgaatgag catcatatat atatatatat    60
atatatatat atatatgact catgttcttg tcggcaagtt ggccttggct a             111

<210> SEQ ID NO 355
<211> LENGTH: 103
<212> TYPE: DNA
<213> ORGANISM: Glycine soja

<400> SEQUENCE: 355
cagccaagga tgacttgccg gcattagcca agtgaatgag catcatatat atatatatat    60 atatatga ctcatgttct tgtcggcaag ttggccttgg cta                        103

<210> SEQ ID NO 356
<211> LENGTH: 83
<212> TYPE: DNA
<213> ORGANISM: Hordeum vulgare

<400> SEQUENCE: 356
taacacgcca gaaataaagc caaggatgag ttgcctgatc atcaggactc atggaggtag    60
ggctttctgt ttttggtgag ttt                                            83

<210> SEQ ID NO 357
<211> LENGTH: 121
<212> TYPE: DNA
<213> ORGANISM: Medicago truncatula

<400> SEQUENCE: 357

```
aagaggcaga gagagtaatg cagccaagga tgacttgccg acaacattgg cgaatgttca      60
tgtgatttct gcctcattgt gccggcaagt tgtccttggc tatgttagtc tctcatcttc     120
t                                                                    121

<210> SEQ ID NO 358
<211> LENGTH: 121
<212> TYPE: DNA
<213> ORGANISM: Medicago truncatula

<400> SEQUENCE: 358
aagaggcaga gagagtaatg cagccaagga tgacttgccg acaacgttgg cgaatgttca      60
tgtgatttct gcctcattgt gccggccagt tgtccttggc tatgttagtc tctcatcttc     120
t                                                                    121

<210> SEQ ID NO 359
<211> LENGTH: 82
<212> TYPE: DNA
<213> ORGANISM: Medicago truncatula

<400> SEQUENCE: 359
tagccaagga caacttgccg gcacaatgag gcagaaatca catgaacatt cgccaatgtt      60
gtcggcaagt catccttggc tg                                              82

<210> SEQ ID NO 360
<211> LENGTH: 95
<212> TYPE: DNA
<213> ORGANISM: Medicago truncatula

<400> SEQUENCE: 360
aagccaagga tgacttgctg ggctaaaaac cattacatgg gacctgatga gtatgtccct      60
tgtttagttt ccggcaggcg ggttatccta ggctt                                95

<210> SEQ ID NO 361
<211> LENGTH: 101
<212> TYPE: DNA
<213> ORGANISM: Medicago truncatula

<400> SEQUENCE: 361
gaaatggagc caaggatgac ttgccggtat attagtttgt cgctaaagct aactagcttt      60
agttgttggg tactcccggc aggtcatcct tcggctatat t                        101

<210> SEQ ID NO 362
<211> LENGTH: 139
<212> TYPE: DNA
<213> ORGANISM: Medicago truncatula

<400> SEQUENCE: 362
tttataagcc aaggatgact tgcctagcta aaaaccattt acattaattg gggacttaat      60
ttgtatatgt tatgtctgat cgatgatgag tatgtccctt gtttagttta ttagcaggca     120
ggtatcctag gcttttga                                                  139

<210> SEQ ID NO 363
<211> LENGTH: 211
<212> TYPE: DNA
<213> ORGANISM: Medicago truncatula

<400> SEQUENCE: 363
```

```
atatgcagcc aaggatgact tgccggcgag cctctttcga tacttttatg acataattaa      60
tcatgtggat agccaaggta ctaaactcac tttgcactaa aacaaatatt tttgctttag     120
tgcaaactta gtttaggcgc ttcgcaacgg ctagtcaaat gtcctagttc caatgtgatt     180
ggttgtccgg caagtcgtct ctggctacgt a                                    211
```

<210> SEQ ID NO 364
<211> LENGTH: 86
<212> TYPE: DNA
<213> ORGANISM: Medicago truncatula

<400> SEQUENCE: 364

```
gatttgagcc aaagatgact tgccggcatg ctgcctgaaa agcaagaagg gtgttgtttt      60
gctggcagtt gtcattggtt catgtt                                           86
```

<210> SEQ ID NO 365
<211> LENGTH: 89
<212> TYPE: DNA
<213> ORGANISM: Medicago truncatula

<400> SEQUENCE: 365

```
agatttgagc caaagatgac ttgccggcat gctgcctgaa aagcaagaag ggtgttgttt      60
tgctggcagt tgtcattggt tcatgtttg                                        89
```

<210> SEQ ID NO 366
<211> LENGTH: 77
<212> TYPE: DNA
<213> ORGANISM: Medicago truncatula

<400> SEQUENCE: 366

```
gagtgcagcc aaggatgact tgccggtaat atatctaatt ccttggtttc ttccggcaag      60
ttgttcttga ctacatt                                                     77
```

<210> SEQ ID NO 367
<211> LENGTH: 240
<212> TYPE: DNA
<213> ORGANISM: Medicago truncatula

<400> SEQUENCE: 367

```
agatgaagcc aaggatgact tgccggtata atagtaattt gccacaaatc tagatagcta      60
ttagctatgt ttggatgggc ggtgagatta acaaaattac agcagcattg tgattttgtt     120
gatgctttaa agtgtagttt ttatcaaaat tacagtggtt cactgtaatt atgagaatct     180
caccgtcaat ctaaatatgc atttagtttc atttccggca ggtcatcctt cggctatatt     240
```

<210> SEQ ID NO 368
<211> LENGTH: 100
<212> TYPE: DNA
<213> ORGANISM: Medicago truncatula

<400> SEQUENCE: 368

```
aaatggagcc aaggatgact tgccggtata ttagtttgtc gctaaagcta actagcttta      60
gttgttgggt actcccggca ggtcatcctt cggctatatt                           100
```

<210> SEQ ID NO 369
<211> LENGTH: 89
<212> TYPE: DNA
<213> ORGANISM: Medicago truncatula

<400> SEQUENCE: 369

```
agatttgagc caaagatgac ttgccggcat gctgcctgaa aagcaagaag ggtgttgttt      60
tgctggcagt tgtcattggt tcatgtttg                                        89

<210> SEQ ID NO 370
<211> LENGTH: 89
<212> TYPE: DNA
<213> ORGANISM: Medicago truncatula

<400> SEQUENCE: 370
agatttgagc caaagatgac ttgccggcat gctgcctgaa aagcaagaag ggtgttgttt      60
tgctggcagt tgtcattggt tcatgtttg                                        89

<210> SEQ ID NO 371
<211> LENGTH: 112
<212> TYPE: DNA
<213> ORGANISM: Oryza sativa

<400> SEQUENCE: 371
gaacgggatg cagccaagga tgacttgccg gctcctggta ttggggaat ctcagctttg       60 ctgaagcgcc ttggagttag ccggcaagtc tgtccttggc tacacctagc tc             112

<210> SEQ ID NO 372
<211> LENGTH: 103
<212> TYPE: DNA
<213> ORGANISM: Oryza sativa

<400> SEQUENCE: 372
atttatcgtg tagccaagga tgaattgccg gcgtttcacg ctgttgatgg tgcgtgcata      60
tataagttgg cgccggcaag tcatttcagg ctacatgttt gcc                       103

<210> SEQ ID NO 373
<211> LENGTH: 132
<212> TYPE: DNA
<213> ORGANISM: Oryza sativa

<400> SEQUENCE: 373
gctggttgtg tagccaagga tgacttgccg gcctggtttg tgttcatcag caatccagca     60
tatgctgtat tgccgtgtgt gatcgatcga tgcatggacc ggcaagttat tttctttggc    120
tacattacaa cc                                                        132

<210> SEQ ID NO 374
<211> LENGTH: 170
<212> TYPE: DNA
<213> ORGANISM: Oryza sativa

<400> SEQUENCE: 374
gctgattcgg tagccaagga tgacttgcct aatgcctatg tgcatgtgtt tatacgctgc     60
tcatctgcat tttgattatc ccctgatcag tcctgtcgtc aattatatgt gtgtgtagta   120
ctctgtactc atacatatat aggcatgtct tccttggcta ttcggagcgg              170

<210> SEQ ID NO 375
<211> LENGTH: 126
<212> TYPE: DNA
<213> ORGANISM: Oryza sativa

<400> SEQUENCE: 375
ctgcctctgg tagccaagga tgacttgcct attgtgctct tctgaatgat gcagtgccat     60
```

```
gatcagtgtg gcctggctgg ttcagatgag ccgagatagg cagtctcctt ggctagcctg    120
agtggc                                                               126

<210> SEQ ID NO 376
<211> LENGTH: 122
<212> TYPE: DNA
<213> ORGANISM: Oryza sativa

<400> SEQUENCE: 376
ttagctctgg tagccaagga tgacttgcct gtgtccttgt gtgtaaggat cattaattat    60
tattcagaaa atgatccttt cagcaggttt catgggcagt ctccttggct agcctgagtg   120
at                                                                  122

<210> SEQ ID NO 377
<211> LENGTH: 108
<212> TYPE: DNA
<213> ORGANISM: Oryza sativa

<400> SEQUENCE: 377
gtagctctgg tagccaagga tgacttgcct gtgtccttgt gtagaggatc attcagaaaa    60
tgagccttga actggttcat aggcagtctc cttggctagt ctgagtcg               108

<210> SEQ ID NO 378
<211> LENGTH: 125
<212> TYPE: DNA
<213> ORGANISM: Oryza sativa

<400> SEQUENCE: 378
tcgcatctgg tagccaagga tgacttgcct gtgtctctgc tcatgtgcag tagaagaaga    60
tgcatttcta gctgctttct gcatatgtga tctcacaggc agtctccttg gctagcctga   120
gcggc                                                               125

<210> SEQ ID NO 379
<211> LENGTH: 156
<212> TYPE: DNA
<213> ORGANISM: Oryza sativa

<400> SEQUENCE: 379
tctgtctaga tagccaagga tgacttgcct gtggcctctt ggagagagag gtgtagctta    60
attagcagca tggtttgagc attgcttgat cggttgatcg cttcgcttgc tctgcatgag   120
atcttacagg cagtctcctt ggctagtctg ggcggc                             156

<210> SEQ ID NO 380
<211> LENGTH: 108
<212> TYPE: DNA
<213> ORGANISM: Oryza sativa

<400> SEQUENCE: 380
ttatctctga tagccaagga tgacttgcct gtgtcctccc tgaaggatta gcaatttaat    60
gatcctttaa gctggttcat gggcagtctc cttggctagc ctgagtgg               108

<210> SEQ ID NO 381
<211> LENGTH: 138
<212> TYPE: DNA
<213> ORGANISM: Oryza sativa

<400> SEQUENCE: 381
tgagtcctgg tagccaagga tgacttgcct gtatatttat atatatatgt gtgtgtgatc    60
```

-continued aatggatgga ttgatcaagc tgcttgcagg ctcatgcata tatatgtaca ggcagtctcc    120
ttggctagcc cggctacc                                                 138

<210> SEQ ID NO 382
<211> LENGTH: 177
<212> TYPE: DNA
<213> ORGANISM: Oryza sativa

<400> SEQUENCE: 382 ctcccttttgg tagccaagaa tgacttgcct atgtgttttg ccttgtgttg gctcatccat    60
ccatctatca gccgttgcag atttgcagtg gcagattaaa gggtttcaga agaaattct     120 tgtgatggat gtgcaatgtg ctgcatggg ccggtcttct tggctagcca gagtggc       177

<210> SEQ ID NO 383
<211> LENGTH: 173
<212> TYPE: DNA
<213> ORGANISM: Oryza sativa

<400> SEQUENCE: 383 ctcccttttgg tagccaagaa tgacttgcct acgcttttgc cctctgttgg ctcatccatc    60
cgtctatcta tctgccatgg cagatggcag attaagggtt tctgaaagaa attcttgtga   120
taggatgtgc aatgaggctg catgggccgg tcttcttggc tagccagagt ggc           173

<210> SEQ ID NO 384
<211> LENGTH: 126
<212> TYPE: DNA
<213> ORGANISM: Oryza sativa

<400> SEQUENCE: 384
gagcaaggtg tagccaagga caaacttgcc ggatcaacag agaaggactg ccagtctccg    60
gccaattaat taacctcgcc gtcggccatc gccggccggc aagtcatcct tggctgcatc   120
ctgctc                                                              126

<210> SEQ ID NO 385
<211> LENGTH: 108
<212> TYPE: DNA
<213> ORGANISM: Oryza sativa

<400> SEQUENCE: 385
ccactcaggc tagccaagga gactgcccat gaaccagctt aaaggatcat taaattgcta    60
atccttcagg gaggacacag gcaagtcatc cttggctatc agagataa                108

<210> SEQ ID NO 386
<211> LENGTH: 146
<212> TYPE: DNA
<213> ORGANISM: Petunia x hybrida

<400> SEQUENCE: 386
aggttagtga aatgcagcca aggatgactt gccggcaagc ttgatcaact ctactttttt    60
aagtactttt tattatagtt aaaaactaag aagtggagat taataacttt gactggcaag   120 tcattttttgg ctacatctct gcctca                                       146

<210> SEQ ID NO 387
<211> LENGTH: 165
<212> TYPE: DNA
<213> ORGANISM: Populus trichocarpa

```
<400> SEQUENCE: 387
aagtggtatg cagccaagga tgacttgccg acttaactga tctgtataaa ttaatgcatg    60
tgtagtcaaa attactacta ctatatatta atctgatctg tgaccacaaa ttaactaact   120
actagctagt aattagttgg caagttgtcc atggctacat gctgc                  165

<210> SEQ ID NO 388
<211> LENGTH: 107
<212> TYPE: DNA
<213> ORGANISM: Populus trichocarpa

<400> SEQUENCE: 388
cttgtttggt agccaaggac gacttgccca ccaccatctc agttgggtcc aatatattac    60
tgggcacctt ccatttggtt ttgggcaagc accttggcta gctgaca               107

<210> SEQ ID NO 389
<211> LENGTH: 107
<212> TYPE: DNA
<213> ORGANISM: Populus trichocarpa

<400> SEQUENCE: 389
tcttgtttgt agccaaggac gacttgccca caatatgtat cgtgagcgtt tccaatttgc    60
aacctcatac ttggtttgtt ttgggcagtc tccttggcta tgcagat               107

<210> SEQ ID NO 390
<211> LENGTH: 101
<212> TYPE: DNA
<213> ORGANISM: Populus trichocarpa

<400> SEQUENCE: 390
gatgttcggt agccaaggac gacttgccca cactatgaga caagtggtta gaattagcaa    60
cttcttaatt ggttatggga agtctccttg gctatgctga c                     101

<210> SEQ ID NO 391
<211> LENGTH: 107
<212> TYPE: DNA
<213> ORGANISM: Populus trichocarpa

<400> SEQUENCE: 391
cttgtttggt agccaaggac gacttgccca ccaccatctt agttgggtcc aatatattac    60
tgggcacctt ccatttggtt ttgggcaagc accttggcta gctgaca               107

<210> SEQ ID NO 392
<211> LENGTH: 107
<212> TYPE: DNA
<213> ORGANISM: Populus trichocarpa

<400> SEQUENCE: 392
cctgtttggt agccaaggac gacttgccca ccaccatctt agttgggtcc agtatattac    60
tgggcacctt ccatttggtt ttgggcaagc accttggcta gctgaca               107

<210> SEQ ID NO 393
<211> LENGTH: 113
<212> TYPE: DNA
<213> ORGANISM: Populus trichocarpa

<400> SEQUENCE: 393
aagattgatg cagccaagga tgacttgccg acgactcgtt tttgctttca tcaatatacg    60
cataattaag aagagatgaa tccgttggca ggttgttctt ggctacattt ttc         113
```

<210> SEQ ID NO 394
<211> LENGTH: 102
<212> TYPE: DNA
<213> ORGANISM: Populus trichocarpa

<400> SEQUENCE: 394
aagtttgatg cagccaagga tgacttgccg acgactcaat ttttgcttcc atatggtaga    60
agagatgaat aggttggcag gttttccttg gctacatttt cc                       102

<210> SEQ ID NO 395
<211> LENGTH: 111
<212> TYPE: DNA
<213> ORGANISM: Populus trichocarpa

<400> SEQUENCE: 395
gagtcgaatg cagccaagga tgacttgccg gcatttcctc ctaagtagcg agcccggcaa    60
ggcttctatt tggcacgccc ggccggcggg ttgtccttgg ctatatttgg t             111

<210> SEQ ID NO 396
<211> LENGTH: 166
<212> TYPE: DNA
<213> ORGANISM: Populus trichocarpa

<400> SEQUENCE: 396
tatcgtggcg cagccaagga tgacttgccg gcaagctcct cacacgtatt ttgtttcgag    60
tttcattgat ggcattgcta gatagatata tatgatttcg taattcaaac ttttgggcca   120
ttgtctggtt gaaatgatcg gcaagctgtc cttggctatg tctcta                   166

<210> SEQ ID NO 397
<211> LENGTH: 239
<212> TYPE: DNA
<213> ORGANISM: Populus trichocarpa

<400> SEQUENCE: 397
ttatgtggtg cagccaagga tgacttgccg gaataagcta tgatcaatag ctatagctat    60 ggtattttttc atcctaggtt tggctatata tatatatata tatagccagt taattgctat   120
aaatctcagc acatttatgt tttatatgtc tgcacacaga cacacacatc attgaatgtt   180
gatgttccac ctcctatgat cagtagtcaa tcggcaagtc atctctggct actcaactc    239

<210> SEQ ID NO 398
<211> LENGTH: 106
<212> TYPE: DNA
<213> ORGANISM: Populus trichocarpa

<400> SEQUENCE: 398
gagtagaatg cagccaagga tgacttgccg gcatttcctc ctaggtagct agcaagcctt    60
ctatttggca tgcctgtccg gcaggttgtc cttggctaaa ttttgt                   106

<210> SEQ ID NO 399
<211> LENGTH: 118
<212> TYPE: DNA
<213> ORGANISM: Populus trichocarpa

<400> SEQUENCE: 399
gagtgtaatt cagccaagga tgacttgccg gcagcacggg atctcagagc ttaataacta    60
gaagatcaag gctgtcatta cttttccggc cggcaagttg cccttggcta cattgtac     118

```
<210> SEQ ID NO 400
<211> LENGTH: 123
<212> TYPE: DNA
<213> ORGANISM: Populus trichocarpa

<400> SEQUENCE: 400
tcttgtttgg tagccaagga tgacttgcct gctccattgt aggaggtttc cgaaaaaatg      60
cagacatgta taatttcgaa acccctgttt cgtttcaggc agtctccttg gctaacttga     120
ctg                                                                  123

<210> SEQ ID NO 401
<211> LENGTH: 137
<212> TYPE: DNA
<213> ORGANISM: Populus trichocarpa

<400> SEQUENCE: 401
tcttgtttga tagccaagga tgacttgcct gctacttgca agagtttctg caaagagatc      60
agaaccaaat atgcatggaa ttatatgtaa tgaaactctt gtttgattgc caggcagtct     120
ccttggctag cctgaca                                                   137

<210> SEQ ID NO 402
<211> LENGTH: 203
<212> TYPE: DNA
<213> ORGANISM: Populus trichocarpa

<400> SEQUENCE: 402
tcttgtttgg tagccaagga tgacttgcct gtagcctccc tcggattcat gaacacgagc      60
atttatgtgg tgctcaaaag aaaaggagag aatgatccca gctggcagcg acaaggtcaa     120
tccattgaag tagcgagaag caggtgattt atagctagaa tccacaagag gttcccagca     180
agtgtccttg gctaacgaga cgg                                            203

<210> SEQ ID NO 403
<211> LENGTH: 143
<212> TYPE: DNA
<213> ORGANISM: Populus trichocarpa

<400> SEQUENCE: 403
tcttgtttga tagccaagga tgacttgcct gctacataca agagatcatt atgcataaat      60
agaacgaaat atgtacatgg tattaattaa tgcagtgaaa actcttgttt ggttgccagg     120
cagtctcctt ggctaagctg aca                                            143

<210> SEQ ID NO 404
<211> LENGTH: 119
<212> TYPE: DNA
<213> ORGANISM: Populus trichocarpa

<400> SEQUENCE: 404
tcttgtttgg tagccaagga tgacttgcct gctcccttca aggaggtttc atgaaatgca      60
gacatgatct ctcgaaaccc ctgttgggtt tcaggcggtc tccttggcta acttgacag      119

<210> SEQ ID NO 405
<211> LENGTH: 107
<212> TYPE: DNA
<213> ORGANISM: Populus trichocarpa

<400> SEQUENCE: 405
agagtggatt tgagccaagg atgacttgcc gcagatgcat ggtccttgct gctgatcaca      60
```

```
taccaagggg ggttttgggt ggcaagcatc cttggttctc cttcgct            107
```

<210> SEQ ID NO 406
<211> LENGTH: 104
<212> TYPE: DNA
<213> ORGANISM: Populus trichocarpa

<400> SEQUENCE: 406

```
ccttgcgtgg aagccaagga tgacttgcct gagaattttta ggaaggtttc tatatgaaag    60 cttttttatta gttttgcagg aagtcaacct tggctttcct atag                    104
```

<210> SEQ ID NO 407
<211> LENGTH: 104
<212> TYPE: DNA
<213> ORGANISM: Populus trichocarpa

<400> SEQUENCE: 407

```
ccttgcgtgg aagccaagga tgacttgcct gagaattttta ggaaggtttc tatatgaaag    60 cttttttatta gttttgcagg aagtcaacct tggctttcct atag                    104
```

<210> SEQ ID NO 408
<211> LENGTH: 115
<212> TYPE: DNA
<213> ORGANISM: Populus trichocarpa

<400> SEQUENCE: 408

```
tcttgttagt tagccaagga cgacttgcct gttcctagca atttgggatt tgccctggac    60
taagaggcag gaccctcatt ccgggtttca ggcagtctcc ttggctaggt tgaca         115
```

<210> SEQ ID NO 409
<211> LENGTH: 119
<212> TYPE: DNA
<213> ORGANISM: Populus trichocarpa

<400> SEQUENCE: 409

```
gagggtttgg tagccaagga tgacttgcct atttcctcca taaggcttta aaaagcatga    60
aatgtggttt agagctcaat tgaagggttc ataggcagtc tactttggtt atcctagct    119
```

<210> SEQ ID NO 410
<211> LENGTH: 120
<212> TYPE: DNA
<213> ORGANISM: Populus trichocarpa

<400> SEQUENCE: 410

```
agagtgtgat tcagccaagg atgacttgcc ggcagcaggt aagagcaaag ctccgttttt    60
ggaagttcaa ggatatctta acttttccgg ccggcaagct gtccttggct acattgtact   120
```

<210> SEQ ID NO 411
<211> LENGTH: 108
<212> TYPE: DNA
<213> ORGANISM: Populus trichocarpa

<400> SEQUENCE: 411

```
ctagagtccg agccaagaat gacttgccgg caggctagca tttgctagct acagggcaag    60
atgtatgcta aagtgacatt ccgccaggtt gttcttggct ctactttg               108
```

<210> SEQ ID NO 412
<211> LENGTH: 122
<212> TYPE: DNA

<213> ORGANISM: Populus trichocarpa

<400> SEQUENCE: 412

```
gagggttggg tagccaagga cgacttgcct atttcctcca tggggtcctg aaaagaatga      60
aatactgtcg ttcagagctc attggtaggg ttcataggca gtctcctttg gctatcctaa     120
ct                                                                    122
```

<210> SEQ ID NO 413
<211> LENGTH: 110
<212> TYPE: DNA
<213> ORGANISM: Populus trichocarpa

<400> SEQUENCE: 413

```
cgtgtttggt agccaaggat gacttgccca ctccattgaa agagttttc aagcatatgg       60
tagtgtagaa cttttctttg gttctgggca gtcatcttgg ctatgctgac                110
```

<210> SEQ ID NO 414
<211> LENGTH: 109
<212> TYPE: DNA
<213> ORGANISM: Populus trichocarpa

<400> SEQUENCE: 414

```
cgtgtttggt agccaaggat gacttgccca ctctatggaa agagttctca agcacacggc      60
agagaggacc cttacttcgg ctctgggcag tcaccttggc tatgctgac                 109
```

<210> SEQ ID NO 415
<211> LENGTH: 118
<212> TYPE: DNA
<213> ORGANISM: Populus trichocarpa

<400> SEQUENCE: 415

```
tgctgttttc tagccaagga tgacttgctc gttagccctt gaaagatgtt tcaaatttag      60
gctgcatatg ctcagaacct ttttctggct tcaggcaatc atcttggcta aatgacag      118
```

<210> SEQ ID NO 416
<211> LENGTH: 123
<212> TYPE: DNA
<213> ORGANISM: Populus trichocarpa

<400> SEQUENCE: 416

```
tcttgtttag tagccatgga tgaattgcct gcttccaaaa tgaggtgtca agccgagata      60
aacatacaag tttgatccct cattggggtt cccaggcagt catcagcttg gctaacttga    120
cag                                                                   123
```

<210> SEQ ID NO 417
<211> LENGTH: 118
<212> TYPE: DNA
<213> ORGANISM: Populus trichocarpa

<400> SEQUENCE: 417

```
tagtagaatg cagccaagaa tgatttgccg gcgccggcca gcacttgttg caaagcaact      60
aagcaagggc ttcaaatgtt tttggcaccc cggcaagttg ttcttggcta catttgga     118
```

<210> SEQ ID NO 418
<211> LENGTH: 101
<212> TYPE: DNA
<213> ORGANISM: Phaeodactylum tricornutum

<400> SEQUENCE: 418

```
cagccaagga tgacttgccg acgactcgct tttgcttttg cttccatcaa tataggcata      60
atcaagaaga gatgaatccg ttggcaggtt gttcttggct a                         101

<210> SEQ ID NO 419
<211> LENGTH: 84
<212> TYPE: DNA
<213> ORGANISM: Phaeodactylum tricornutum

<400> SEQUENCE: 419
cagccaagga tgatttgccg acgactcagt ttttgcttcc atatggtagg agagatgaag      60
aggttggcag gttttccttg gcta                                             84

<210> SEQ ID NO 420
<211> LENGTH: 92
<212> TYPE: DNA
<213> ORGANISM: Ricinus communis

<400> SEQUENCE: 420
gaatacagcc aaggatgact tgccggcatc aatttatata tatatatata tatatatata      60
tttatcggca agctgttctt ggctatattc at                                    92

<210> SEQ ID NO 421
<211> LENGTH: 93
<212> TYPE: DNA
<213> ORGANISM: Ricinus communis

<400> SEQUENCE: 421
taattcagcc aaggatgact tgccggcaca gcctatatat gtcttctact cacagctgct      60
agctaccggc aagttgttct tggctacatt gta                                   93

<210> SEQ ID NO 422
<211> LENGTH: 114
<212> TYPE: DNA
<213> ORGANISM: Ricinus communis

<400> SEQUENCE: 422
ggacctgagc caaggatgac ttgccgcgca tatataaaat tctttctgtc gccagcaatc      60
atcgatagcc tgaaaagggt tttccgtggc aagacattct tggctctact tcac           114

<210> SEQ ID NO 423
<211> LENGTH: 91
<212> TYPE: DNA
<213> ORGANISM: Sorghum bicolor

<400> SEQUENCE: 423
cagccaagga tgacttgccg atcgatcgat gcaaactcct ctgatgtctg atctcatcag      60
attatcgttg tcggaaagtt gttcttggct a                                     91

<210> SEQ ID NO 424
<211> LENGTH: 102
<212> TYPE: DNA
<213> ORGANISM: Sorghum bicolor

<400> SEQUENCE: 424
cagccaagga tgacttgccg gatatgtgca tgcatatgtt acaaggcagc atatgcaccc      60
tgttacaagc ctgcctgttc tccggcaagt tgtccttggc ta                        102

<210> SEQ ID NO 425
```

<211> LENGTH: 126
<212> TYPE: DNA
<213> ORGANISM: Sorghum bicolor

<400> SEQUENCE: 425

```
tggcgagagc ctgcctttgg tagccaagga tgacttgcct acacggcctt gcgagttccg    60
gttgcatggc cagttcagtt gggtttgtgg gcggtcacct tggctagcct gagtggctct   120
tgcctg                                                              126
```

<210> SEQ ID NO 426
<211> LENGTH: 125
<212> TYPE: DNA
<213> ORGANISM: Sorghum bicolor

<400> SEQUENCE: 426

```
tggcgagagc ctgcctttgg tagccaagga tgacttgcct acatggcatt gcgagttccg    60
gttgcatggc cagttcagct gagtttgtgg gcggtcacct tgggacggta tcgataagct   120
tgata                                                               125
```

<210> SEQ ID NO 427
<211> LENGTH: 240
<212> TYPE: DNA
<213> ORGANISM: Sorghum bicolor
<220> FEATURE:
<221> NAME/KEY: misc_feature
<222> LOCATION: (205)..(205)
<223> OTHER INFORMATION: n is a, t, g, or c

<400> SEQUENCE: 427

```
agagtggttg gtagctctgg tagccaagga tgacttgcct gtgtgccggc ctcgatcgat    60
ctcccggccc tctcaaggat cgatcatcgt gcgtgcgtgt cgatcgatcg tcgtcgtcgt   120
cgtcacctct ggcagagagc gagacgatga tcgatcgatt agccgcgcgc cttgggttgt   180
tggggtgtgg tcgcggtctc acagncagtc tccttggcta gccctgactc actcttatca   240
```

<210> SEQ ID NO 428
<211> LENGTH: 148
<212> TYPE: DNA
<213> ORGANISM: Sorghum bicolor

<400> SEQUENCE: 428

```
cgatgagagc actgctctgg tagccaagga tgacttgcct gtggcctcca ctccacctgc    60
ggcaggaggc tcttcttctg cgcgcgcgtg tgtgtgtggt tgtcgatcgc aggcagtctc   120
cttggctagc ctcagcggct ctcatcct                                      148
```

<210> SEQ ID NO 429
<211> LENGTH: 152
<212> TYPE: DNA
<213> ORGANISM: Sorghum bicolor

<400> SEQUENCE: 429

```
gcgataagag tctgcccaga tagccaagga tgacttgcct gtggcctctt ggcttggctt    60
gagagcttat taactctgtg cacgtttaat ttgctcttct tgtggcctcg atcacaggca   120
gtctccttgg ctagtccggg cggctcttat ct                                 152
```

<210> SEQ ID NO 430
<211> LENGTH: 155
<212> TYPE: DNA
<213> ORGANISM: Sorghum bicolor

```
<400> SEQUENCE: 430
gcgataagag tctgcccaga tagccaagga tgacttgcct gtggcctctt ggcttggctt      60
gagagcttat taactctgtg cacgtttaat ttggctcttc ttggggcctc gatcacaggg     120
cagtctccct tggctagtcc ggggcgggct cctta                                155

<210> SEQ ID NO 431
<211> LENGTH: 169
<212> TYPE: DNA
<213> ORGANISM: Sorghum bicolor

<400> SEQUENCE: 431
gatggagagc cccctttgc tagccaagaa tgacttgcct atgcatgccc tctgttggca       60
attcctccag ccatggagat tgcacaaggt gaattttgc ggcatagatg atggatgcaa      120
tgtggctgca tgggcaggtc ttcttggcta gccagagtgc tctcatcca                 169

<210> SEQ ID NO 432
<211> LENGTH: 123
<212> TYPE: DNA
<213> ORGANISM: Sorghum bicolor

<400> SEQUENCE: 432
tgtagccaag gatgacttgc cggccgatcg atgcctcatc cctgtccggg aacgtcatgc      60
atgtgatgca aactgtgagg ccgcatcgtc gatcgaccgg caggttcttc tctttggcta    120
cac                                                                   123

<210> SEQ ID NO 433
<211> LENGTH: 97
<212> TYPE: DNA
<213> ORGANISM: Sorghum bicolor

<400> SEQUENCE: 433
cagccaagga tgacttgccg gctcctcaaa tttgaagcgt cgtctaagct gctgaggctt      60
aataaaaact tagtcggcaa gtctgtcctt ggctaca                               97

<210> SEQ ID NO 434
<211> LENGTH: 97
<212> TYPE: DNA
<213> ORGANISM: Sorghum bicolor

<400> SEQUENCE: 434
gctagccaag gagactgcct atgaaccatc tatctcaaag gctcacattt ctgatccttc      60
ggcacaaagg acacaggcaa gtcatccttg gctatca                              97

<210> SEQ ID NO 435
<211> LENGTH: 92
<212> TYPE: DNA
<213> ORGANISM: Sorghum bicolor

<400> SEQUENCE: 435
tagccaagga tgacttgcct atatcctctc taaaggatca gcaaatattg aggcttctag      60
tggtctcata tgggcagtct ccttggctag cc                                   92

<210> SEQ ID NO 436
<211> LENGTH: 93
<212> TYPE: DNA
<213> ORGANISM: Sorghum bicolor
```

<400> SEQUENCE: 436
ggtagccaag gatgacttgc ctatatcctc tatgaaggat cagcaaatat cgaggctttg    60
agtggtctca tgggcagtct ccttggctag cct    93

<210> SEQ ID NO 437
<211> LENGTH: 103
<212> TYPE: DNA
<213> ORGANISM: Sorghum bicolor

<400> SEQUENCE: 437
atagccaagg atgatttgcc tgtagcaacc tctgagtgct cctgctgcca tggcagtcag    60
gagcgccaag tgggtgcttc tccgggcaaa tcatctgggc tag    103

<210> SEQ ID NO 438
<211> LENGTH: 105
<212> TYPE: DNA
<213> ORGANISM: Sorghum bicolor

<400> SEQUENCE: 438
ttagccaaga atggcttgcc tatctccatt atttggttca tcagagggac ctctgatccc    60
tcatgatgga tgaaatgtgg atgatggcag cccttctggc taagt    105

<210> SEQ ID NO 439
<211> LENGTH: 104
<212> TYPE: DNA
<213> ORGANISM: Sorghum bicolor

<400> SEQUENCE: 439
ttagccaaga atggcttgcc tatctccatt attttgttca tcgatgcagg cctagggatc    60
gtcatggatg aaatgtggat gatggcatcc attcttggct aagt    104

<210> SEQ ID NO 440
<211> LENGTH: 149
<212> TYPE: DNA
<213> ORGANISM: Solanum lycopersicum

<400> SEQUENCE: 440
ggtctataag gtttgcatga agttgaagag agtcaagttg cagccaagga tgacttgccg    60
gaccaaaagt tgtgaccatt ttctagttcc ggcaagttgt ttttggctat aagtttgctc    120
tcttcttctc atgttatcct cgttagacc    149

<210> SEQ ID NO 441
<211> LENGTH: 205
<212> TYPE: DNA
<213> ORGANISM: Solanum lycopersicum

<400> SEQUENCE: 441
ttttaatttg gtttcaggca gtctccttgg ctaccttgac atgctctttt cttttatgca    60
agatatcttt tcaaaataga agttttagtc atcgttaaaa tatcgagacg gggttacaag    120
tcttatttaa aagaagagaa gtctagcatg atgagaagag tcttatttgg tagccaagga    180
tgacttgcct gcaccgtact tgaaa    205

<210> SEQ ID NO 442
<211> LENGTH: 147
<212> TYPE: DNA
<213> ORGANISM: Solanum lycopersicum

<400> SEQUENCE: 442

```
gtctagagag ttattgtatg aagaggtagg gagtggagtg cagccaagga tgacttgccg    60
agatgttgta gcctaatgca atgacatatc ggcaggtcat ctttggctac attttattct   120
ctcctattca tgtaaaactt tatagac                                        147

<210> SEQ ID NO 443
<211> LENGTH: 143
<212> TYPE: DNA
<213> ORGANISM: Saccharum officinarum

<400> SEQUENCE: 443
tagccaagga tgacttgccg gcaatgcttc gatggatccc taatcccgt ccggccggga    60 acgtcgcacg tatgtatgta tgcgtgcata tgctgcgaac tgtgaggcat ccatatcgac   120
cggcaggttc ttctcttggg cta                                            143

<210> SEQ ID NO 444
<211> LENGTH: 146
<212> TYPE: DNA
<213> ORGANISM: Saccharum spp.

<400> SEQUENCE: 444
gtagccaagg atgacttgcc ggccgatgct tcgatggatc cctcatcccc gtccggccgg    60
gaacgtcgca cgtatgtatg tatgcgtgca tatgctgcga actgtgaggc atccatatcg   120
accggcaggt tcttctcttt ggctac                                         146

<210> SEQ ID NO 445
<211> LENGTH: 147
<212> TYPE: DNA
<213> ORGANISM: Theobroma cacao

<400> SEQUENCE: 445
taggcacaga aagtgaagtg cagccaagga tgacttgccg attctccctc ttgcatccat    60
tcagttttgc caacaccagc aactcatatg tagagacgaa tttaaatcgg caggttgtcc   120
ttggctacat gtttctttct gctccac                                        147

<210> SEQ ID NO 446
<211> LENGTH: 193
<212> TYPE: DNA
<213> ORGANISM: Theobroma cacao

<400> SEQUENCE: 446
ggaaatgagg ctatgtgctg cagccaagga tgacttgccg gaaaagctat attttacatt    60
atattaccct gttccctgat attaactata tgcttctgta tcaattttaa ctataaatta   120
ataaaattta taataaatgt tataagagtt tatcggcaag tcgtctctgg ctatatcact   180
gtttcatttt ctc                                                       193

<210> SEQ ID NO 447
<211> LENGTH: 142
<212> TYPE: DNA
<213> ORGANISM: Theobroma cacao

<400> SEQUENCE: 447
taggcctaga aaggatggtg cagccaagga tgacttgccg actactccct ccagcctttg    60
ctgtactgtt ttttatattg aaaaaatgga tatagatgaa gtgggcaagt cgtctttggc   120
tacatttttc tttctcctcc tc                                             142
```

<210> SEQ ID NO 448
<211> LENGTH: 152
<212> TYPE: DNA
<213> ORGANISM: Theobroma cacao

<400> SEQUENCE: 448
agattaagag tcttgttggg tagccaagga tgacttgcct atatccaaaa aggattttga        60
ggaaagaaaa gctgaatctg ataaatctca tcagagtcct tttaatggtt tctgggcagt       120
ctcctttggc tatcctgact ggctcttatc tt                                     152

<210> SEQ ID NO 449
<211> LENGTH: 147
<212> TYPE: DNA
<213> ORGANISM: Theobroma cacao

<400> SEQUENCE: 449
taggcacaga aagtgaagtg cagccaagga tgacttgccg attctttctc ttatatccat        60
tcagttttac caacactagc aactcatatg taaagacgaa tttaaatcgg caagttgtcc       120
ttggctacat gtttcttttt gctccac                                           147

<210> SEQ ID NO 450
<211> LENGTH: 141
<212> TYPE: DNA
<213> ORGANISM: Theobroma cacao

<400> SEQUENCE: 450
aagaagagag cctcgctgga aagccaagaa tgacttgcct gcttcctcct tgaggtttca        60
aaatttcaat gaaactttta aaacccgcca ttctggctcg cgggcagtct tcttcgcttt       120
cttgacaggc tattcttttc c                                                 141

<210> SEQ ID NO 451
<211> LENGTH: 144
<212> TYPE: DNA
<213> ORGANISM: Theobroma cacao

<400> SEQUENCE: 451
gataaagagt ctttgtttgg tagccaggga tgacttgcct acggcttttc aggtggttaa        60
tattgatgct atgattatga atgtaaaacc cctggctctg gtctgcaggc agtcaccttg       120
gctatgctaa caggctcttt tctc                                              144

<210> SEQ ID NO 452
<211> LENGTH: 139
<212> TYPE: DNA
<213> ORGANISM: Theobroma cacao

<400> SEQUENCE: 452
aggtaaagag tcatgcttgg tagccaagga tgacttgcct gcacctttcc ccaaggattc        60
aagtaaatgg ctaagaaacc tgaaactcct ttcaggttgc caggcagtca cctaggctaa       120
tctagcaggt tcttttccc                                                    139

<210> SEQ ID NO 453
<211> LENGTH: 115
<212> TYPE: DNA
<213> ORGANISM: Theobroma cacao

<400> SEQUENCE: 453
aagataagag ttctgtttgg tagccaagga tgagttgcct gctccttcca agaggtttca        60

```
aatcttgttg ggttgccagg cattcacctt ggctaacttg actggctctt ttctt        115
```

<210> SEQ ID NO 454
<211> LENGTH: 141
<212> TYPE: DNA
<213> ORGANISM: Theobroma cacao

<400> SEQUENCE: 454

```
agataaagag tcttgtttga tagccaagga tgacttgcct gtacctcaca gcaggtttct    60
cttaggttaa aagttcttcc ttggaagccc ctgtctagtt tcaggcaatt atccttggct   120
aacctgacag gctcttctct a                                             141
```

<210> SEQ ID NO 455
<211> LENGTH: 132
<212> TYPE: DNA
<213> ORGANISM: Theobroma cacao

<400> SEQUENCE: 455

```
aagaggtaga cagtgtggtg cagccaagga tgacttgccg gctaatccct aggaggcatg    60
catttgcctt gtttctctgc tttagattat tccggctagt tgtccttggc tacggtgcgc   120
tgtcttcttc tc                                                       132
```

<210> SEQ ID NO 456
<211> LENGTH: 122
<212> TYPE: DNA
<213> ORGANISM: Theobroma cacao

<400> SEQUENCE: 456

```
gagaggtaga gaatttagtg cagccaagga tgacttgccg gcgtagacaa tactcaaata    60
ctaattatta ttgtattttt ccggcaagtc tgtccttggc tacattggtt tctcttcttc   120
tc                                                                  122
```

<210> SEQ ID NO 457
<211> LENGTH: 124
<212> TYPE: DNA
<213> ORGANISM: Theobroma cacao

<400> SEQUENCE: 457

```
aagaaaggga cagtggagtt tgagccaagg atgacttgcc gggatatttg ctgcggagca    60
gtatatgcct caactgtctt ccgaaaagtc attttggct caccttcgct ctcatgtttt    120
ccat                                                                124
```

<210> SEQ ID NO 458
<211> LENGTH: 124
<212> TYPE: DNA
<213> ORGANISM: Vitis vinifera

<400> SEQUENCE: 458

```
gagagtggaa tgcagccaag gatgacttgc cggaatttat atatagtgag aagagaagag    60
gctatatgct ttcacatata tagtgaaccc tggcaagttg tccttggcta catttgattc   120
tctt                                                                124
```

<210> SEQ ID NO 459
<211> LENGTH: 105
<212> TYPE: DNA
<213> ORGANISM: Vitis vinifera

```
<400> SEQUENCE: 459
ggggtcgaat tgagccaagg atggcttgcc gtcatctgca gcaagagttg gagactttta    60
actgtgcgtg cacggttagt catccttggc tcatttggcc cttct                   105

<210> SEQ ID NO 460
<211> LENGTH: 90
<212> TYPE: DNA
<213> ORGANISM: Vitis vinifera

<400> SEQUENCE: 460
gggagtagaa tgcagccaag gatgacttgc cggagatggg gcattcctcg ttaatccggc    60
aagttgtcct tggctacatt gggctctctt                                     90

<210> SEQ ID NO 461
<211> LENGTH: 149
<212> TYPE: DNA
<213> ORGANISM: Vitis vinifera

<400> SEQUENCE: 461
gtcttgtctg atagccaagg atgacttgcc tgccctatcc caagtgggtc aatttctttc    60 tttttccaa gtagtgtttg atatttgata tatcatgaat ccggttgttt gggttccagg    120
cagtcacctt ggctaatttt acaggctct                                     149

<210> SEQ ID NO 462
<211> LENGTH: 184
<212> TYPE: DNA
<213> ORGANISM: Vitis vinifera

<400> SEQUENCE: 462
gatattatgg tgcagccaag gatgacttgc cgaaaataat ttgctcgatc gttaatgtgc    60
ttctccagtt tctattgcaa tttatgcata gggcaatata tatatccttt atagcttgtt   120
aattcagata ttgactgagg aatcaataat gggcaagttg tgtttggcta catgtttatc   180
tcat                                                                184

<210> SEQ ID NO 463
<211> LENGTH: 121
<212> TYPE: DNA
<213> ORGANISM: Vitis vinifera

<400> SEQUENCE: 463
gaaagtatgg tgcagccaag gatgacttgc cgactctcta cttagccatc tgcctttctc    60
caaggaggct tgcagtactg atgaagccgg caagttgtct ttggctacat gcttctttct   120
g                                                                   121

<210> SEQ ID NO 464
<211> LENGTH: 101
<212> TYPE: DNA
<213> ORGANISM: Vitis vinifera

<400> SEQUENCE: 464
agggtggaat tgagccaagg atggcttgcc gtcctttgtc actatttgag gcattaactg    60
gtcacgcacg gagggttatc cttgactcct ttagctcctc t                       101

<210> SEQ ID NO 465
<211> LENGTH: 105
<212> TYPE: DNA
<213> ORGANISM: Vitis vinifera
```

<400> SEQUENCE: 465 aggg tggaat tgagccaagg atgactggcc gtcattttc agttggtatt tgaggcttta    60
actggtcatg cacggctggt tatccctgtc tcctttagct cctct    105

<210> SEQ ID NO 466
<211> LENGTH: 122
<212> TYPE: DNA
<213> ORGANISM: Vitis vinifera

<400> SEQUENCE: 466
gagagtggag tgcagccaag gatgacttgc cggaattcac atatagagtg gaatgaggca    60
atagaccggc ctcttctcat ggtgtccctg gcaggttgtc cttggctacc tttcgctctc    120
tt    122

<210> SEQ ID NO 467
<211> LENGTH: 122
<212> TYPE: DNA
<213> ORGANISM: Vitis vinifera

<400> SEQUENCE: 467
gagagtggag tgcagccaag gatgacttgc cggaattcac atatagagtg gaatgaggca    60
agaggccggc ctcttcccat ggtgtccctg gcaggttgtc cttggctacc tttcgttctc    120
tt    122

<210> SEQ ID NO 468
<211> LENGTH: 103
<212> TYPE: DNA
<213> ORGANISM: Vitis vinifera

<400> SEQUENCE: 468
agggtggaat tgagccaagg atgacttgcc gtcctttgca tcaagcattg aagctttaac    60
tgggcatgca cggctagtta ttcttggctc atttggcccc tct    103

<210> SEQ ID NO 469
<211> LENGTH: 102
<212> TYPE: DNA
<213> ORGANISM: Vitis vinifera

<400> SEQUENCE: 469
agagtggaag tgagccaagg atgacttgcc ggcagctgca gcaaggcatt aaggtttaac    60
tggccataac tggcaagcat ccgaggctct gtttcaccct ct    102

<210> SEQ ID NO 470
<211> LENGTH: 101
<212> TYPE: DNA
<213> ORGANISM: Vitis vinifera

<400> SEQUENCE: 470
tgagtggaat agagccaagg atgacttgcc ggcaactgca gcaaggcata gggtttaact    60
ggtcataact ggcaagcatc tgaggctcta tttcaccctc t    101

<210> SEQ ID NO 471
<211> LENGTH: 103
<212> TYPE: DNA
<213> ORGANISM: Vitis vinifera

<400> SEQUENCE: 471

```
agggtggatt tgagccaagg atgacttgcc gccatcagca gcaagcattg aagctttaac      60
tgggcatgga cagcgagtta ttcttggctc atgcggcccc tct                       103

<210> SEQ ID NO 472
<211> LENGTH: 102
<212> TYPE: DNA
<213> ORGANISM: Vitis vinifera

<400> SEQUENCE: 472
agtgtggaat tgagccaagg atgacttgcc ggcagctgca gcaaggcatt aaggtttaac      60
tggctataac tggcaagcat ccgaggctct gtttcaccct ct                        102

<210> SEQ ID NO 473
<211> LENGTH: 97
<212> TYPE: DNA
<213> ORGANISM: Vitis vinifera

<400> SEQUENCE: 473
agggtggaat agagccaagg atgacttgcc ggcatttgca gtaagtctat attaactgga      60
acagccggca tgtaatcctg gctctatttg gtcctct                              97

<210> SEQ ID NO 474
<211> LENGTH: 109
<212> TYPE: DNA
<213> ORGANISM: Vitis vinifera

<400> SEQUENCE: 474
agggtggaat tgagtcaagg atgacttgcc gatatatatt tgcagaaggc atgcaggggc      60
ttttagctat gtgtaaccgg caagttgact tgactcagtt tggccctct                 109

<210> SEQ ID NO 475
<211> LENGTH: 99
<212> TYPE: DNA
<213> ORGANISM: Vitis vinifera

<400> SEQUENCE: 475
gaaagtggat tgcagccaag gatgacttgc cggcacttgg cattaggcac catcgatcat      60
cttcccggca agttgttcct ggctacattc tgctctctt                            99

<210> SEQ ID NO 476
<211> LENGTH: 110
<212> TYPE: DNA
<213> ORGANISM: Vitis vinifera

<400> SEQUENCE: 476
agggtggaat cgagtcaagg atgacttgcc gatatatatt tgcggaagga cttgcatggg      60
cctttagcta tgtgtaaccg gcaagttgac ttgactcagt ttggccctct                110

<210> SEQ ID NO 477
<211> LENGTH: 110
<212> TYPE: DNA
<213> ORGANISM: Vitis vinifera

<400> SEQUENCE: 477
agggtggaat tgagtcaagg atgacttgcc gttatatatt tgcagaaggg cacgcagggg      60
cctttagcta tgtgttaccg gcaagttgac ttgactctgt ttggccctct                110

<210> SEQ ID NO 478
<211> LENGTH: 96
```

```
<212> TYPE: DNA
<213> ORGANISM: Vitis vinifera

<400> SEQUENCE: 478
agggaggaac aaagccaagg atgaattgcc ggcgatgaaa gtaggcagct ttgtccatgg    60
atcggcaatt tatttcttgg ctatgttggg ctctct                              96

<210> SEQ ID NO 479
<211> LENGTH: 143
<212> TYPE: DNA
<213> ORGANISM: Vitis vinifera

<400> SEQUENCE: 479
ggttatgtgg tgcagccaag gatgacttgc cggcaactcc ctttattgta ctcatgcatg    60
ctcatactta tactgttgtg ggcatcattt aagtggcaaa atggtggtc ggcgagtcat    120 tcttagctac atttctgcct cat                                            143

<210> SEQ ID NO 480
<211> LENGTH: 125
<212> TYPE: DNA
<213> ORGANISM: Vitis vinifera

<400> SEQUENCE: 480
gtctcgtctg gtagccaagg atgacttgcc taaatccacc aggtttcaaa acactgaatg    60
taattatcca caaagcgatt ccgtggtctt taggcagtca ttccttcggc taaactgacc   120
ggctc                                                                125

<210> SEQ ID NO 481
<211> LENGTH: 248
<212> TYPE: DNA
<213> ORGANISM: Vitis vinifera

<400> SEQUENCE: 481
cgttgtttgg tagcgaagga tgacttgcct acagcctcct taaggtttca aaataccgag    60
cttgtctacc tttgatcaaa tgattcaaga acaaaagaa agaaaggcc atggcagcca   120 tccatcagag tcaacatgag aatcatgttc tatagaaatt ggagtcattc ttgagaatga   180
acacgacact attagcttgg aatctataat gtggtttatg gcaagtctcc ttggcacctg   240
atggcctc                                                             248

<210> SEQ ID NO 482
<211> LENGTH: 130
<212> TYPE: DNA
<213> ORGANISM: Zea mays

<400> SEQUENCE: 482
taggctcggg gactatggtg cagccaagga tgacttgccg atcgatgtga cgcctcttga    60
tctcgtcgtc gtcagatcgt cgccgatcat cggcaagttg ttcttggcta caccgtggct   120
cctgctcctg                                                           130

<210> SEQ ID NO 483
<211> LENGTH: 156
<212> TYPE: DNA
<213> ORGANISM: Zea mays

<400> SEQUENCE: 483
taggctcggg gactacggtg cagccaagga tgacttgccg atctatcgtc gatcaacgag    60
```

```
cgacgcctct gatgtctgat ctcgacatct atcgtcgtca gaccatcatc atctatcggc    120
aagttgttct tggctacacc gtggctcctg ctcctg                              156

<210> SEQ ID NO 484
<211> LENGTH: 134
<212> TYPE: DNA
<213> ORGANISM: Zea mays

<400> SEQUENCE: 484
atgaggtaga gaacgggatg cagccaagga tgacttgccg gctcctggaa cctggaggcg    60
tctcagcttg ctgtgctgtg gcttagaact tagtcggcaa gtctgtcctt ggctacacct   120
agttctcttc ctct                                                      134

<210> SEQ ID NO 485
<211> LENGTH: 128
<212> TYPE: DNA
<213> ORGANISM: Zea mays

<400> SEQUENCE: 485
gcaatagggg ccactcaggc tagccaagga gactgcctat gaacctctca atggtccaca    60
cattcaggtc ctttgtaaac aaaggacata ggcaagtcat ccttggctat cagaggtagg   120
cccttatt                                                             128

<210> SEQ ID NO 486
<211> LENGTH: 128
<212> TYPE: DNA
<213> ORGANISM: Zea mays

<400> SEQUENCE: 486
gcaatagggg ccactcaggc tagccaagga gactgcctac gaaccaacac aaaggtccac    60
aattctgatc ctttgtaaac aaaggacata ggcaagtcat ccttggctat cagaggcagg   120
cccttatt                                                             128

<210> SEQ ID NO 487
<211> LENGTH: 150
<212> TYPE: DNA
<213> ORGANISM: Zea mays

<400> SEQUENCE: 487
accagagctg attcgttcag tagccaagga tgacttgcct aggtatatat gcatgggcta    60
tggctacatg cctgagagcc agtctcttgt gacgctgagc atgtatagtg taggcatgtc   120
ttccttggct actcggagcg gctctagtca                                    150

<210> SEQ ID NO 488
<211> LENGTH: 140
<212> TYPE: DNA
<213> ORGANISM: Zea mays

<400> SEQUENCE: 488
cagagctagc ctgcctctgg tagccaagga tgacttgcct acatggtctc gctagttccg    60
gttgttgcat gcatgccact atgccagtcc tgctgggttt gtgggcggtc tccttggcta   120
gcctgagtgg ctcttgcctg                                                140

<210> SEQ ID NO 489
<211> LENGTH: 128
<212> TYPE: DNA
<213> ORGANISM: Zea mays
```

```
<400> SEQUENCE: 489
caataagggc ctgcctctga tagccaagga tgacttgcct atgtcctttg tttacaaagg    60
atcagaattg tggacctttg tgttggttcg taggcagtct ccttggctag cctgagtggc   120
ccctattg                                                            128

<210> SEQ ID NO 490
<211> LENGTH: 191
<212> TYPE: DNA
<213> ORGANISM: Zea mays

<400> SEQUENCE: 490
gatgagagtg gtagctctgg tagccaagga tgacttgcct gtgtgctggc cacgctcccc    60
tcatgcaagg accatctcgt gtcgaccgac gagcgagcga gcgatcgatc gatgagagga   120
tgacgaagct tggggtgtac gttggtctct cacgggcagt ctccttggct agccctgact   180
cactcttacc g                                                       191

<210> SEQ ID NO 491
<211> LENGTH: 151
<212> TYPE: DNA
<213> ORGANISM: Zea mays

<400> SEQUENCE: 491
gcgataagag tctgtccaga tagccaagga tgacttgcct gtggcttctt ggcttggctt    60
ggctcgggca aaaccttgtg cacgttttat tgctcgcctc gtggcctcga tcacaggcag   120
tctccttggc tagtccgggc gggcccctta t                                 151

<210> SEQ ID NO 492
<211> LENGTH: 133
<212> TYPE: DNA
<213> ORGANISM: Zea mays

<400> SEQUENCE: 492
cgatgagagc actgtctctgg tagccaagga tgacttgcct gtggcctcca tcagtcgcag    60
aggacgctgt tcttctgctt gtggttgtcg atcgcaggca gtctccttgg ctagcccgag   120
cggctctcat cca                                                     133

<210> SEQ ID NO 493
<211> LENGTH: 89
<212> TYPE: DNA
<213> ORGANISM: Zea mays

<400> SEQUENCE: 493
tagccaagga tgacttgcct atgtcctttg tttacaaagg atcagaattg tggacctttg    60
tgttggttcg taggcagtct ccttggcta                                    89

<210> SEQ ID NO 494
<211> LENGTH: 89
<212> TYPE: DNA
<213> ORGANISM: Zea mays

<400> SEQUENCE: 494
tagccaagga tgacttgcct atgtcctttg tttacaaagg acctgaatgt gtggaccatt    60
gagaggttca taggcagtct ccttggcta                                    89

<210> SEQ ID NO 495
```

<211> LENGTH: 191
<212> TYPE: DNA
<213> ORGANISM: Zea mays

<400> SEQUENCE: 495

```
gtagccaagg atgacttgcc ggccgacata tgcctctctc gttcgtccct gaccggccgg    60
gaaacacatc acgccgcatg catgcatgca tgcatatgtg tgtacgtact acgtgtgcat   120
gcatgcatgt gctgccgcgc gcagcaaact gcgaggaatc gtccgtccgg caggttcttc   180
tctttggcta c                                                        191
```

<210> SEQ ID NO 496
<211> LENGTH: 145
<212> TYPE: DNA
<213> ORGANISM: Zea mays

<400> SEQUENCE: 496

```
cccggcagct cgatcgtgtg ctagctcatc agcttacact tagcaagcaa atgaagcatg    60
cagttctcgc catgagtata aattatcatc tgaggccttg catgtgggga tgaggctgtt   120
atgtagccaa ggatgacttg ccggg                                         145
```

<210> SEQ ID NO 497
<211> LENGTH: 131
<212> TYPE: DNA
<213> ORGANISM: Zea mays

<400> SEQUENCE: 497

```
tgtagccaag gatgacttgc cggccgatgc ctcctcgata taatcgtc gcacatccct     60
gggcggccgg gaacgtcgca tgcatgcaaa ctgttggggc atcggccggc aggttcttct   120
ctttggctac a                                                        131
```

<210> SEQ ID NO 498
<211> LENGTH: 69
<212> TYPE: DNA
<213> ORGANISM: Zea mays

<400> SEQUENCE: 498

```
cgcgtagcca aggatgactt gccggcatta tatttcttgg cccgccggca agtcatctgg    60
ggctacgcg                                                            69
```

<210> SEQ ID NO 499
<211> LENGTH: 95
<212> TYPE: DNA
<213> ORGANISM: Zea mays

<400> SEQUENCE: 499

```
cagccaagga tgacttgccg gctcctggaa cctggaggcg tctcagcttg ctgtgctgtg    60
gcttagaact tagtcggcaa gtctgtcctt ggcta                               95
```

<210> SEQ ID NO 500
<211> LENGTH: 150
<212> TYPE: DNA
<213> ORGANISM: Zea mays

<400> SEQUENCE: 500

```
cagccaagga tgacttgccg acctattttt cttttaacat tccaatgtaa atccatggca    60
tatatatatg gttgtatatc atattgaagt ccagatctag aacattataa taatgttat   120
atagggttta tcggcaagtc atcattggct                                    150
```

<210> SEQ ID NO 501
<211> LENGTH: 116
<212> TYPE: DNA
<213> ORGANISM: Zea mays

<400> SEQUENCE: 501
cagccaagga tgacttgccg atctatcgtc gatcaacgag cgacgcctct gatgtctgat    60
ctcgacatct atcgtcgtca gaccatcatc atctatcggc aagttgttct tggcta       116

<210> SEQ ID NO 502
<211> LENGTH: 90
<212> TYPE: DNA
<213> ORGANISM: Zea mays

<400> SEQUENCE: 502
cagccaagga tgacttgccg atcgatgtga cgcctcttga tctcgtcgtc gtcagatcgt    60
cgccgatcat cggcaagttg ttcttggcta                                    90

<210> SEQ ID NO 503
<211> LENGTH: 338
<212> TYPE: PRT
<213> ORGANISM: Solanum tuberosum

<400> SEQUENCE: 503

Met Ala Asn Gly Lys Ile Lys Ile Gly Ile Asn Gly Phe Gly Arg Ile
1               5                   10                  15

Gly Arg Leu Val Ala Arg Val Ala Leu Gln Arg Asp Asp Val Glu Leu
            20                  25                  30

Val Ala Val Asn Asp Pro Phe Ile Ser Thr Asp Tyr Met Thr Tyr Met
        35                  40                  45

Phe Lys Tyr Asp Ser Val His Gly Gln Trp Lys His His Glu Leu Lys
    50                  55                  60

Val Lys Asp Glu Lys Thr Leu Leu Phe Gly Glu Lys Ala Val Thr Val
65                  70                  75                  80

Phe Gly Ile Arg Asn Pro Glu Asp Ile Pro Trp Gly Glu Ala Gly Ala
                85                  90                  95

Asp Phe Val Val Glu Ser Thr Gly Val Phe Thr Asp Lys Asp Lys Ala
            100                 105                 110

Ala Ala His Leu Lys Gly Gly Ala Lys Lys Val Val Ile Ser Ala Pro
        115                 120                 125

Ser Lys Asp Ala Pro Met Phe Val Val Gly Val Asn Glu Asn Glu Tyr
    130                 135                 140

Lys Pro Glu Leu Asp Ile Val Ser Asn Ala Ser Cys Thr Thr Asn Cys
145                 150                 155                 160

Leu Ala Pro Leu Ala Lys Val Ile Asn Asp Arg Phe Gly Ile Val Glu
                165                 170                 175

Gly Leu Met Thr Thr Val His Ala Met Thr Ala Thr Gln Lys Thr Val
            180                 185                 190

Asp Gly Pro Ser Met Lys Asp Trp Arg Gly Gly Arg Ala Ala Ser Phe
        195                 200                 205

Asn Ile Ile Pro Ser Ser Thr Gly Ala Ala Lys Ala Val Gly Lys Val
    210                 215                 220

Leu Pro Ser Leu Asn Gly Lys Leu Thr Gly Met Ala Phe Arg Val Pro
225                 230                 235                 240

Thr Ala Asp Val Ser Val Val Asp Leu Thr Val Arg Leu Glu Lys Glu

```
                        245                 250                 255
Ala Ser Tyr Glu Asp Ile Lys Ala Ala Ile Lys Glu Glu Ser Glu Gly
                260                 265                 270

Lys Leu Lys Gly Ile Leu Gly Tyr Thr Glu Asp Asp Val Val Ser Thr
                275                 280                 285

Asp Phe Val Gly Asp Ser Arg Ser Ser Ile Phe Asp Ala Lys Ala Gly
            290                 295                 300

Ile Ala Leu Ser Lys Asn Phe Val Lys Leu Val Ser Trp Tyr Asp Asn
305                 310                 315                 320

Glu Trp Gly Tyr Ser Ser Arg Val Ile Asp Leu Ile Cys His Met Ala
                325                 330                 335

Lys Ala

<210> SEQ ID NO 504
<211> LENGTH: 338
<212> TYPE: PRT
<213> ORGANISM: Solanum tuberosum

<400> SEQUENCE: 504

Met Ala Asn Gly Lys Ile Lys Ile Gly Ile Asn Gly Phe Gly Arg Ile
1               5                   10                  15

Gly Arg Leu Val Ala Arg Val Ala Leu Gln Arg Asp Asp Val Glu Leu
                20                  25                  30

Val Ala Val Asn Asp Pro Phe Ile Ser Thr Asp Tyr Met Thr Tyr Met
                35                  40                  45

Phe Lys Tyr Asp Ser Val His Gly Gln Trp Lys His His Glu Leu Lys
            50                  55                  60

Val Lys Asp Glu Lys Thr Leu Leu Phe Gly Glu Lys Ala Val Thr Val
65                  70                  75                  80

Phe Gly Ile Arg Asn Pro Glu Asp Ile Pro Trp Gly Glu Ala Gly Ala
                85                  90                  95

Asp Phe Val Val Glu Ser Thr Gly Val Phe Thr Asp Lys Asp Lys Ala
                100                 105                 110

Ala Ala His Leu Lys Gly Gly Ala Lys Lys Val Val Ile Ser Ala Pro
            115                 120                 125

Ser Lys Asp Ala Pro Met Phe Val Val Gly Val Asn Glu Asn Glu Tyr
130                 135                 140

Lys Pro Glu Leu Asp Ile Val Ser Asn Ala Ser Cys Thr Thr Asn Cys
145                 150                 155                 160

Leu Ala Pro Leu Ala Lys Val Ile Asn Asp Arg Phe Gly Ile Val Glu
                165                 170                 175

Gly Leu Met Thr Thr Val His Ala Met Thr Val Thr Gln Lys Thr Val
                180                 185                 190

Asp Gly Pro Ser Met Lys Asp Trp Arg Gly Gly Arg Ala Ala Ser Phe
            195                 200                 205

Asn Ile Ile Pro Ser Ser Thr Gly Ala Ala Lys Ala Val Gly Lys Val
            210                 215                 220

Leu Pro Ser Leu Asn Gly Lys Leu Thr Gly Met Ala Phe Arg Val Pro
225                 230                 235                 240

Thr Ala Asp Val Ser Val Asp Leu Thr Val Arg Leu Glu Lys Glu
                245                 250                 255

Ala Ser Tyr Glu Asp Ile Lys Ala Ala Ile Lys Glu Glu Ser Glu Gly
                260                 265                 270

Lys Leu Lys Gly Ile Leu Gly Tyr Thr Glu Asp Asp Val Val Ser Thr
```

```
            275                 280                 285
Asp Phe Val Gly Asp Ser Arg Ser Ser Ile Phe Asp Ala Lys Ala Gly
290                 295                 300

Ile Ala Leu Ser Lys Asn Phe Val Lys Leu Val Ser Trp Tyr Asp Asn
305                 310                 315                 320

Glu Trp Gly Tyr Ser Ser Arg Val Ile Asp Leu Ile Cys His Met Ala
                325                 330                 335

Lys Ala

<210> SEQ ID NO 505
<211> LENGTH: 340
<212> TYPE: PRT
<213> ORGANISM: Nicotiana langsdorffii x Nicotiana sanderae

<400> SEQUENCE: 505

Met Ala Ser Asp Lys Lys Ile Lys Ile Gly Ile Asn Gly Phe Gly Arg
1               5                   10                  15

Ile Gly Arg Leu Val Ala Arg Val Ala Leu Gln Arg Asp Asp Val Glu
                20                  25                  30

Leu Val Ala Val Asn Asp Pro Phe Ile Ser Thr Asp Tyr Met Thr Tyr
            35                  40                  45

Met Phe Lys Tyr Asp Ser Val His Gly Gln Trp Lys His His Glu Leu
        50                  55                  60

Lys Val Lys Asp Glu Lys Thr Leu Leu Phe Gly Glu Lys Ser Val Arg
65                  70                  75                  80

Val Phe Gly Ile Arg Asn Pro Glu Glu Ile Pro Trp Ala Glu Ala Gly
                85                  90                  95

Ala Asp Phe Val Val Glu Ser Thr Gly Val Phe Thr Asp Lys Asp Lys
            100                 105                 110

Ala Ala Ala His Leu Lys Gly Gly Ala Lys Lys Val Ile Ser Ala
        115                 120                 125

Pro Ser Lys Asp Ala Pro Met Phe Val Val Gly Val Asn Glu Lys Glu
130                 135                 140

Tyr Lys Pro Glu Tyr Asp Ile Val Ser Asn Ala Ser Cys Thr Thr Asn
145                 150                 155                 160

Cys Leu Ala Pro Leu Ala Lys Val Ile Asn Asp Arg Phe Gly Ile Val
                165                 170                 175

Glu Gly Leu Met Thr Thr Val His Ser Leu Thr Ala Thr Gln Lys Thr
            180                 185                 190

Val Asp Gly Pro Ser Met Lys Asp Trp Arg Gly Gly Arg Ala Ala Ser
        195                 200                 205

Phe Asn Ile Ile Pro Ser Ser Thr Gly Ala Ala Lys Ala Val Gly Lys
210                 215                 220

Val Leu Pro Ala Leu Asn Gly Lys Leu Thr Gly Met Ala Phe Arg Val
225                 230                 235                 240

Pro Thr Val Asp Val Ser Val Val Asp Leu Thr Val Arg Leu Glu Lys
                245                 250                 255

Glu Ala Ser Tyr Asp Glu Ile Lys Ala Ala Ile Lys Glu Glu Ser Glu
            260                 265                 270

Gly Lys Leu Lys Gly Ile Leu Gly Phe Thr Glu Asp Asp Val Val Ser
        275                 280                 285

Thr Asp Phe Val Gly Asp Ser Arg Ser Ser Ile Phe Asp Ala Lys Ala
290                 295                 300

Gly Ile Ala Leu Ser Lys Asn Phe Val Lys Leu Val Ser Trp Tyr Asp
```

```
                305                 310                 315                 320
Asn Glu Trp Gly Tyr Ser Ser Arg Val Ile Asp Leu Ile Cys His Met
                    325                 330                 335

Ala Ser Val Ala
            340

<210> SEQ ID NO 506
<211> LENGTH: 338
<212> TYPE: PRT
<213> ORGANISM: Thellungiella halophila

<400> SEQUENCE: 506

Met Thr Gly Ala Lys Ile Lys Ile Gly Ile Asn Gly Phe Gly Arg Ile
1               5                   10                  15

Gly Arg Leu Val Ala Arg Val Val Leu Gln Arg Asp Asp Val Glu Leu
                20                  25                  30

Val Ala Val Asn Asp Pro Phe Ile Thr Thr Glu Tyr Met Thr Tyr Met
            35                  40                  45

Phe Lys Tyr Asp Ser Val His Gly Gln Trp Lys His His Glu Leu Lys
    50                  55                  60

Val Lys Asp Glu Lys Thr Leu Leu Phe Gly Glu Lys Pro Val Thr Val
65                  70                  75                  80

Phe Gly Ile Lys Asn Pro Glu Asp Ile Pro Trp Gly Glu Ala Gly Ala
                85                  90                  95

Asp Phe Val Val Glu Ser Thr Gly Val Phe Thr Asp Lys Asp Lys Ala
            100                 105                 110

Ala Ala His Leu Lys Gly Gly Ala Lys Lys Val Val Ile Ser Ala Pro
        115                 120                 125

Ser Lys Asp Ala Pro Met Phe Val Val Gly Val Asn Glu His Glu Tyr
130                 135                 140

Lys Ser Asp Leu Asp Ile Val Ser Asn Ala Ser Cys Thr Thr Asp Cys
145                 150                 155                 160

Leu Ala Pro Leu Ala Lys Val Ile Asn Asp Arg Phe Gly Ile Val Glu
                165                 170                 175

Gly Leu Met Thr Thr Val His Ser Ile Thr Ala Thr Gln Lys Thr Val
            180                 185                 190

Asp Gly Pro Ser Met Lys Asp Trp Arg Gly Gly Arg Ala Ala Ser Phe
        195                 200                 205

Asn Ile Ile Pro Ser Ser Thr Gly Ala Ala Lys Ala Val Gly Lys Val
    210                 215                 220

Leu Pro Gln Leu Asn Gly Lys Leu Thr Gly Met Ser Phe Arg Val Pro
225                 230                 235                 240

Thr Val Asp Val Ser Val Val Asp Leu Thr Val Arg Leu Glu Lys Ala
                245                 250                 255

Ala Thr Tyr Asp Glu Ile Lys Lys Ala Ile Lys Glu Glu Ser Glu Gly
            260                 265                 270

Lys Leu Lys Gly Ile Leu Gly Tyr Thr Glu Asp Asp Val Val Ser Thr
        275                 280                 285

Asp Phe Val Gly Asp Ser Arg Ser Ser Ile Phe Asp Ala Lys Ala Gly
    290                 295                 300

Ile Ala Leu Ser Glu Asn Phe Val Lys Leu Val Ser Trp Tyr Asp Asn
305                 310                 315                 320

Glu Trp Gly Tyr Ser Thr Arg Val Val Asp Leu Ile Val His Met Ser
                325                 330                 335
```

Lys Ala

<210> SEQ ID NO 507
<211> LENGTH: 338
<212> TYPE: PRT
<213> ORGANISM: Arabidopsis thaliana

<400> SEQUENCE: 507

Met Ala Asp Lys Lys Ile Arg Ile Gly Ile Asn Gly Phe Gly Arg Ile
1               5                   10                  15

Gly Arg Leu Val Ala Arg Val Val Leu Gln Arg Asp Asp Val Glu Leu
            20                  25                  30

Val Ala Val Asn Asp Pro Phe Ile Thr Thr Glu Tyr Met Thr Tyr Met
        35                  40                  45

Phe Lys Tyr Asp Ser Val His Gly Gln Trp Lys His His Glu Leu Lys
    50                  55                  60

Val Lys Asp Asp Lys Thr Leu Leu Phe Gly Glu Lys Pro Val Thr Val
65                  70                  75                  80

Phe Gly Ile Arg Asn Pro Glu Asp Ile Pro Trp Gly Glu Ala Gly Ala
                85                  90                  95

Asp Phe Val Val Glu Ser Thr Gly Val Phe Thr Asp Lys Asp Lys Ala
            100                 105                 110

Ala Ala His Leu Lys Gly Gly Ala Lys Lys Val Val Ile Ser Ala Pro
        115                 120                 125

Ser Lys Asp Ala Pro Met Phe Val Val Gly Val Asn Glu His Glu Tyr
130                 135                 140

Lys Ser Asp Leu Asp Ile Val Ser Asn Ala Ser Cys Thr Thr Asn Cys
145                 150                 155                 160

Leu Ala Pro Leu Ala Lys Val Ile Asn Asp Arg Phe Gly Ile Val Glu
                165                 170                 175

Gly Leu Met Thr Thr Val His Ser Ile Thr Ala Thr Gln Lys Thr Val
            180                 185                 190

Asp Gly Pro Ser Met Lys Asp Trp Arg Gly Gly Arg Ala Ala Ser Phe
        195                 200                 205

Asn Ile Ile Pro Ser Ser Thr Gly Ala Ala Lys Ala Val Gly Lys Val
    210                 215                 220

Leu Pro Ser Leu Asn Gly Lys Leu Thr Gly Met Ser Phe Arg Val Pro
225                 230                 235                 240

Thr Val Asp Val Ser Val Val Asp Leu Thr Val Arg Leu Glu Lys Ala
                245                 250                 255

Ala Thr Tyr Asp Glu Ile Lys Lys Ala Ile Lys Glu Glu Ser Glu Gly
            260                 265                 270

Lys Met Lys Gly Ile Leu Gly Tyr Thr Glu Asp Asp Val Val Ser Thr
        275                 280                 285

Asp Phe Val Gly Asp Asn Arg Ser Ser Ile Phe Asp Ala Lys Ala Gly
    290                 295                 300

Ile Ala Leu Ser Asp Lys Phe Val Lys Leu Val Ser Trp Tyr Asp Asn
305                 310                 315                 320

Glu Trp Gly Tyr Ser Ser Arg Val Val Asp Leu Ile Val His Met Ser
                325                 330                 335

Lys Ala

<210> SEQ ID NO 508
<211> LENGTH: 338
<212> TYPE: PRT

<213> ORGANISM: Arabidopsis lyrata subsp. lyrata

<400> SEQUENCE: 508

Met Ala Asp Lys Lys Ile Arg Ile Gly Ile Asn Gly Phe Gly Arg Ile
1               5                   10                  15

Gly Arg Leu Val Ala Arg Val Val Leu Gln Arg Asp Asp Val Glu Leu
            20                  25                  30

Val Ala Val Asn Asp Pro Phe Ile Thr Thr Glu Tyr Met Thr Tyr Met
        35                  40                  45

Phe Lys Tyr Asp Ser Val His Gly Gln Trp Lys His His Glu Leu Lys
    50                  55                  60

Val Lys Asp Asp Lys Thr Leu Leu Phe Gly Glu Lys Pro Val Thr Val
65                  70                  75                  80

Phe Gly Ile Arg Asn Pro Glu Glu Ile Pro Trp Gly Glu Ala Gly Ala
                85                  90                  95

Asp Phe Val Val Glu Ser Thr Gly Val Phe Thr Asp Lys Asp Lys Ala
            100                 105                 110

Ala Ala His Leu Lys Gly Gly Ala Lys Lys Val Val Ile Ser Ala Pro
        115                 120                 125

Ser Lys Asp Ala Pro Met Phe Val Val Gly Val Asn Glu His Glu Tyr
130                 135                 140

Lys Ser Asp Leu Asp Ile Val Ser Asn Ala Ser Cys Thr Thr Asn Cys
145                 150                 155                 160

Leu Ala Pro Leu Ala Lys Val Ile Asn Asp Arg Phe Gly Ile Val Glu
                165                 170                 175

Gly Leu Met Thr Thr Val His Ser Ile Thr Ala Thr Gln Lys Thr Val
            180                 185                 190

Asp Gly Pro Ser Met Lys Asp Trp Arg Gly Gly Arg Ala Ala Ser Phe
        195                 200                 205

Asn Ile Ile Pro Ser Ser Thr Gly Ala Ala Lys Ala Val Gly Lys Val
    210                 215                 220

Leu Pro Ser Leu Asn Gly Lys Leu Thr Gly Met Ser Phe Arg Val Pro
225                 230                 235                 240

Thr Val Asp Val Ser Val Val Asp Leu Thr Val Arg Leu Glu Lys Ala
                245                 250                 255

Ala Thr Tyr Asp Glu Ile Lys Lys Ala Ile Lys Glu Glu Ser Glu Gly
            260                 265                 270

Lys Leu Lys Gly Ile Leu Gly Tyr Thr Glu Asp Asp Val Val Ser Thr
        275                 280                 285

Asp Phe Val Gly Asp Asn Arg Ser Ser Ile Phe Asp Ala Lys Ala Gly
    290                 295                 300

Ile Ala Leu Ser Asp Lys Phe Val Lys Leu Val Ser Trp Tyr Asp Asn
305                 310                 315                 320

Glu Trp Gly Tyr Ser Ser Arg Val Val Asp Leu Ile Val His Met Ser
                325                 330                 335

Lys Ala

<210> SEQ ID NO 509
<211> LENGTH: 337
<212> TYPE: PRT
<213> ORGANISM: Nicotiana tabacum

<400> SEQUENCE: 509

Met Ala Lys Val Lys Ile Gly Ile Asn Gly Phe Gly Arg Ile Gly Arg
1               5                   10                  15

Leu Val Ala Arg Val Ala Leu Gln Arg Asp Val Glu Leu Val Ala
                20                  25                  30

Val Asn Asp Pro Phe Ile Ser Val Glu Tyr Met Thr Tyr Met Phe Lys
             35                  40                  45

Tyr Asp Ser Val His Gly Gln Trp Lys His His Glu Leu Lys Val Lys
 50                  55                  60

Asp Asp Lys Thr Leu Leu Phe Gly Lys Ala Val Thr Val Phe Gly
 65                  70                  75                  80

Phe Arg Asn Pro Glu Glu Ile Pro Trp Gly Gln Thr Gly Ala Asp Tyr
                 85                  90                  95

Ile Val Glu Ser Thr Gly Val Phe Thr Asp Lys Asp Lys Ala Ala
                100                 105                 110

His Leu Lys Gly Gly Ala Lys Lys Val Ile Ile Ser Ala Pro Ser Lys
                115                 120                 125

Asp Ala Pro Met Phe Val Val Gly Val Asn Glu Lys Glu Tyr Lys Pro
130                 135                 140

Glu Leu Asn Ile Val Ser Asn Ala Ser Cys Thr Thr Asn Cys Leu Ala
145                 150                 155                 160

Pro Leu Ala Lys Val Ile Asn Asp Arg Phe Gly Ile Val Glu Gly Leu
                165                 170                 175

Met Thr Thr Val His Ser Ile Thr Ala Thr Gln Lys Thr Val Asp Gly
                180                 185                 190

Pro Ser Ala Lys Asp Trp Arg Gly Gly Arg Ala Ala Ser Phe Asn Ile
                195                 200                 205

Ile Pro Ser Ser Thr Gly Ala Ala Lys Ala Val Gly Lys Val Leu Pro
                210                 215                 220

Ala Leu Asn Gly Lys Leu Thr Gly Met Ala Phe Arg Val Pro Thr Val
225                 230                 235                 240

Asp Val Ser Val Val Asp Leu Thr Val Arg Leu Glu Lys Glu Ala Thr
                245                 250                 255

Tyr Asp Glu Ile Lys Ala Ala Ile Lys Glu Glu Ser Glu Gly Lys Leu
                260                 265                 270

Lys Gly Ile Leu Gly Tyr Thr Glu Asp Val Val Ser Thr Asp Phe
                275                 280                 285

Val Gly Asp Asn Arg Ser Ser Ile Phe Asp Ala Lys Ala Gly Ile Ala
                290                 295                 300

Leu Ser Lys Asn Phe Val Lys Leu Val Ser Trp Tyr Asp Asn Glu Trp
305                 310                 315                 320

Gly Tyr Ser Thr Arg Val Val Asp Leu Ile Lys His Met Ala Ser Val
                325                 330                 335

Gln

<210> SEQ ID NO 510
<211> LENGTH: 338
<212> TYPE: PRT
<213> ORGANISM: Arabidopsis thaliana

<400> SEQUENCE: 510

Met Ala Asp Lys Lys Ile Arg Ile Gly Ile Asn Gly Phe Gly Arg Ile
 1               5                  10                  15

Gly Arg Leu Val Ala Lys Val Val Leu Gln Arg Asp Asp Val Glu Leu
                20                  25                  30

Val Ala Val Asn Asp Pro Phe Ile Thr Thr Glu Tyr Met Thr Tyr Met
             35                  40                  45

```
Phe Lys Tyr Asp Ser Val His Gly Gln Trp Lys His His Glu Leu Lys
 50                  55                  60

Val Lys Asp Asp Lys Thr Leu Leu Phe Gly Glu Lys Pro Val Thr Val
 65                  70                  75                  80

Phe Gly Ile Arg Asn Pro Glu Asp Ile Pro Trp Gly Glu Ala Gly Ala
                 85                  90                  95

Asp Phe Val Val Glu Ser Thr Gly Val Phe Thr Asp Lys Asp Lys Ala
                100                 105                 110

Ala Ala His Leu Lys Gly Gly Ala Lys Lys Val Val Ile Ser Ala Pro
            115                 120                 125

Ser Lys Asp Ala Pro Met Phe Val Gly Val Asn Glu His Glu Tyr
    130                 135                 140

Lys Ser Asp Leu Asp Ile Val Ser Asn Ala Ser Cys Thr Thr Asn Cys
145                 150                 155                 160

Leu Ala Pro Leu Ala Lys Val Ile Asn Asp Arg Phe Gly Ile Val Glu
                165                 170                 175

Gly Leu Met Thr Thr Val His Ser Ile Thr Ala Thr Gln Lys Thr Val
                180                 185                 190

Asp Gly Pro Ser Met Lys Asp Trp Arg Gly Gly Arg Ala Ala Ser Phe
                195                 200                 205

Asn Ile Ile Pro Ser Ser Thr Gly Ala Ala Lys Ala Val Gly Lys Val
210                 215                 220

Leu Pro Ser Leu Asn Gly Lys Leu Thr Gly Met Ser Phe Arg Val Pro
225                 230                 235                 240

Thr Val Asp Val Ser Val Val Asp Leu Thr Val Arg Leu Glu Lys Ala
                245                 250                 255

Ala Thr Tyr Asp Glu Val Lys Lys Ala Ile Lys Glu Glu Ser Glu Gly
                260                 265                 270

Lys Met Lys Gly Ile Leu Gly Tyr Thr Glu Asp Asp Val Val Ser Thr
            275                 280                 285

Asp Phe Val Gly Asp Asn Arg Ser Ser Ile Phe Asp Ala Lys Ala Gly
    290                 295                 300

Ile Ala Leu Ser Asp Lys Phe Val Lys Leu Val Ser Trp Tyr Asp Asn
305                 310                 315                 320

Glu Trp Gly Tyr Ser Ser Arg Val Val Asp Leu Ile Val His Met Ser
                325                 330                 335

Lys Ala

<210> SEQ ID NO 511
<211> LENGTH: 326
<212> TYPE: PRT
<213> ORGANISM: Nicotiana tabacum

<400> SEQUENCE: 511

Gly Arg Ile Gly Arg Leu Val Ala Arg Val Ala Leu Gln Arg Asp Asp
  1               5                  10                  15

Val Glu Leu Val Ala Val Asn Asp Pro Phe Ile Ser Thr Asp Tyr Met
                 20                  25                  30

Thr Tyr Met Phe Lys Tyr Asp Ser Val His Gly Gln Trp Lys His His
             35                  40                  45

Glu Leu Lys Val Lys Asp Glu Lys Thr Leu Leu Phe Gly Glu Lys Ser
 50                  55                  60

Val Arg Val Phe Gly Ile Arg Asn Pro Glu Glu Ile Pro Trp Ala Glu
 65                  70                  75                  80
```

```
Ala Gly Ala Asp Phe Val Val Glu Ser Thr Gly Val Phe Thr Asp Lys
                85                  90                  95

Asp Lys Ala Ala Ala His Leu Lys Gly Gly Ala Lys Lys Val Val Ile
            100                 105                 110

Ser Ala Pro Ser Lys Asp Ala Pro Met Phe Val Gly Val Asn Glu
        115                 120                 125

Lys Glu Tyr Lys Pro Glu Tyr Asp Ile Val Ser Asn Ala Ser Cys Thr
130                 135                 140

Thr Asn Cys Leu Ala Pro Leu Ala Lys Val Ile Asn Asp Arg Phe Gly
145                 150                 155                 160

Ile Val Glu Gly Leu Met Thr Thr Val His Ser Leu Thr Ala Thr Gln
                165                 170                 175

Lys Thr Val Asp Gly Pro Ser Met Lys Asp Trp Arg Gly Gly Arg Ala
            180                 185                 190

Thr Ser Phe Asn Ile Ile Pro Ser Ser Thr Gly Ala Ala Lys Ala Val
        195                 200                 205

Gly Lys Val Leu Pro Ala Leu Asn Gly Lys Leu Thr Gly Met Ala Phe
    210                 215                 220

Arg Val Pro Thr Val Asp Val Ser Val Val Asp Leu Thr Val Arg Leu
225                 230                 235                 240

Glu Lys Glu Ala Ser Tyr Asp Asp Ile Lys Ala Ala Ile Lys Glu Glu
                245                 250                 255

Ser Glu Gly Lys Leu Lys Gly Ile Leu Gly Phe Thr Glu Asp Asp Val
            260                 265                 270

Val Ser Thr Asp Phe Val Gly Asp Ser Arg Ser Ser Ile Phe Asp Ala
        275                 280                 285

Lys Ala Gly Ile Ala Leu Ser Lys Asn Phe Val Lys Leu Val Ser Trp
    290                 295                 300

Tyr Asp Asn Glu Trp Gly Tyr Ser Ser Arg Val Ile Asp Leu Ile Cys
305                 310                 315                 320

His Met Ala Ser Val Ala
                325

<210> SEQ ID NO 512
<211> LENGTH: 338
<212> TYPE: PRT
<213> ORGANISM: Sinapis alba

<400> SEQUENCE: 512

Met Ala Asp Lys Lys Ile Lys Ile Gly Ile Asn Gly Phe Gly Arg Ile
1               5                   10                  15

Gly Arg Leu Val Ala Arg Val Ile Leu Gln Arg Asn Asp Val Glu Leu
            20                  25                  30

Val Ala Val Asn Asp Pro Phe Ile Thr Thr Glu Tyr Met Thr Tyr Met
        35                  40                  45

Phe Lys Tyr Asp Ser Val His Gly Gln Trp Lys His Asn Glu Leu Lys
    50                  55                  60

Val Lys Asp Glu Lys Thr Leu Leu Phe Gly Glu Lys Pro Val Thr Val
65                  70                  75                  80

Phe Gly Ile Arg Asn Pro Glu Asp Ile Pro Trp Gly Glu Ala Gly Ala
                85                  90                  95

Asp Phe Val Val Glu Ser Thr Gly Val Phe Thr Asp Lys Asp Lys Ala
            100                 105                 110

Ala Ala His Leu Lys Gly Gly Ala Lys Lys Val Val Ile Ser Ala Pro
```

```
                   115                 120                 125
Ser Lys Asp Ala Pro Met Phe Val Val Gly Val Asn Glu His Glu Tyr
    130                 135                 140

Lys Ser Asp Leu Asn Ile Val Ser Asn Ala Ser Cys Thr Thr Asn Cys
145                 150                 155                 160

Leu Ala Pro Leu Ala Lys Val Ile Asn Asp Arg Phe Gly Ile Val Glu
                165                 170                 175

Gly Leu Met Thr Thr Val His Ser Ile Thr Ala Thr Gln Lys Thr Val
            180                 185                 190

Asp Gly Pro Ser Met Lys Asp Trp Arg Gly Arg Ala Ala Ser Phe
        195                 200                 205

Asn Ile Ile Pro Ser Ser Thr Gly Ala Ala Lys Ala Val Gly Lys Val
    210                 215                 220

Leu Pro Gln Leu Asn Gly Lys Leu Thr Gly Met Ser Phe Arg Val Pro
225                 230                 235                 240

Thr Val Asp Val Ser Val Val Asp Leu Thr Val Arg Leu Glu Lys Ala
                245                 250                 255

Ala Thr Tyr Asp Glu Ile Lys Lys Ala Ile Lys Glu Glu Ser Gln Gly
            260                 265                 270

Lys Leu Lys Gly Ile Leu Gly Tyr Thr Glu Asp Asp Val Val Ser Thr
        275                 280                 285

Asp Phe Val Gly Asp Asn Arg Ser Ser Ile Phe Asp Ala Lys Ala Gly
    290                 295                 300

Ile Ala Leu Ser Asp Asn Phe Val Lys Leu Val Ser Trp Tyr Asp Asn
305                 310                 315                 320

Glu Trp Gly Tyr Ser Thr Arg Val Val Asp Leu Ile Ile His Met Ser
                325                 330                 335

Lys Ala
```

<210> SEQ ID NO 513
<211> LENGTH: 1194
<212> TYPE: DNA
<213> ORGANISM: Solanum tuberosum

<400> SEQUENCE: 513

```
atggccaatg gcaagatcaa aatcggaatc aacggattcg gtagaattgg tcgtttggtt    60
gctagagttg ctctgcagag ggatgatgtt gaactagttg cagtgaatga tccatttatt   120
tccactgatt acatgacata tatgtttaaa tatgattcag tacatggaca atggaagcac   180
catgagctta aggttaagga tgagaagacc cttctcttcg gtgagaaggc tgttacagtt   240
tttggaatca ggaaccctga agatatccca tgggggaag ctggtgctga cttcgtcgtt   300
gaatcaaccg tgtcttcac tgacaaggac aaggctgctg ctcacttgaa gggtggtgcc   360
aagaaggttg tgatctccgc tcctagcaaa gatgccccca tgtttgttgt gggtgtcaac   420
gagaatgaat acaagccaga gttggacatt gtctccaacg ctagttgcac tactaactgc   480
cttgcacctt tggctaaggt catcaatgac aggtttggca ttgtggaggg tctcatgacc   540
actgtccacg ccatgactgc cacccagaaa actgttgatg gtccatccat gaaggactgg   600
agaggtggaa gagctgcttc attcaacatc atccctagca gcactggagc agccaaggct   660
gttggaaaag tgctcccatc acttaacggc aaattgactg gaatggcctt cagagtacca   720
actgctgatg tttctgttgt cgaccttact gtaagacttg agaaagaagc tcatatgaa    780
gacatcaagg ctgcaatcaa ggaggaatca gagggtaaat tgaagggtat cttgggatac   840
```

| | | |
|---|---|---|
| actgaagatg atgtggtttc cacagacttt gttggtgaca gcaggtcaag cattttcgat | 900 | |
| gccaaggctg gaattgcttt gagcaagaac tttgtgaaac ttgtgtcatg gtatgacaac | 960 | |
| gaatggggtt acagttcccg tgtgattgat ttgatctgcc atatggccaa ggcttgattg | 1020 | |
| atgctgctgg ggagcagaag acaatctgtt ttagttttg cttgaagtat tagttttctg | 1080 | |
| ggccgggagt ggtctttctt gtttatgtgt aatggaataa ccagagagga acggaaccct | 1140 | |
| gttgttatct ttgaggatat cttttactgt ttgacttgtc atgaatgaat caaa | 1194 | |

<210> SEQ ID NO 514
<211> LENGTH: 1293
<212> TYPE: DNA
<213> ORGANISM: Solanum tuberosum

<400> SEQUENCE: 514

| | | |
|---|---|---|
| cactatacct aatttctctc tttacatatt ttcttagctt tcaccctttt tttcttagca | 60 | |
| atggccaatg caagatcaa aatcggaatc aacggattcg gtagaattgg tcgtttggtt | 120 | |
| gctagagttg ctctgcagag ggatgatgtt gaactagttg cagtgaatga tccatttatt | 180 | |
| tccactgatt acatgacata tatgtttaaa tatgattcag tacatggaca atggaagcac | 240 | |
| catgagctta aggttaagga tgagaagacc cttctcttcg gtgagaaggc tgttacagtt | 300 | |
| tttggaatca ggaaccctga agatatccca tgggggggaag ctggtgctga cttcgtcgtt | 360 | |
| gaatcaaccg tgtcttcac tgacaaggac aaggctgctg ctcacttgaa gggtggtgcc | 420 | |
| aagaaggttg tgatctccgc tcctagcaaa gatgccccca tgттттgттgт gggtgtcaac | 480 | |
| gagaatgaat acaagccaga gttggacatt gtctccaacg ctagttgcac tactaactgc | 540 | |
| cttgcacctt tggctaaggt catcaatgac aggtttggca ttgtggaggg tctcatgacc | 600 | |
| actgtccacg ccatgactgt cacccagaaa actgttgatg tccatccat gaaggactgg | 660 | |
| agaggtggaa gagctgcttc attcaacatc atccctagca gcactggagc agccaaggct | 720 | |
| gttgaaaag tgctcccatc acttaacggc aaaattgactg gaatggcctt cagagtacca | 780 | |
| actgctgatg tttctgttgt cgaccttact gtaagacttg agaaagaagc tcatatgaa | 840 | |
| gacatcaagg ctgcaatcaa ggaggaatca gagggtaaat tgaagggtat cttgggatac | 900 | |
| actgaagatg atgtggtttc cacagacttt gttggtgaca gcaggtcaag cattttcgat | 960 | |
| gccaaggctg gaattgcttt gagcaagaac tttgtgaaac ttgtgtcatg gtatgacaac | 1020 | |
| gaatggggtt acagttcccg tgtgattgat ttgatctgcc atatggccaa ggcttgattg | 1080 | |
| atgctgctgg ggagcagaag acaatctgtt ttagtttttg cttgaagtat тagтттттcтg | 1140 | |
| ggccgggagt ggtctttctt gtttatgtgt aatggaataa ccagagagga acggaaccct | 1200 | |
| gttgttatct ttgaggatat cтттттacтgт ttgacttgtc atgaatgaat caaactttac | 1260 | |
| tttttccagt aaaaaaaaaa aaaaaaaaaa aaa | 1293 | |

<210> SEQ ID NO 515
<211> LENGTH: 1328
<212> TYPE: DNA
<213> ORGANISM: Nicotiana langsdorffii x Nicotiana sanderae

<400> SEQUENCE: 515

| | | |
|---|---|---|
| cgacattcac tactattctt ttcactaagc aattttctct cctacatttc tttaaacccc | 60 | |
| ттттттттacc cctaagccat ggcatctgac aagaagatca agatcggaat caatggattt | 120 | |
| ggaaggattg tcgtttggt ggcaagagtt gctctgcaga gagatgatgt tgaactagtt | 180 | |
| gcagtgaacg acccatttat ctctactgat tacatgacat acatgtttaa gtatgattca | 240 | |

```
gttcatggac aatggaaaca ccatgagctt aaagtcaagg atgaaaagac ccttcttttt    300
ggtgagaagt ccgtcagagt ctttggaatc aggaaccctg aagaaattcc atgggctgag    360
gctggtgctg atttcgttgt ggagtccact ggtgtcttca ctgacaagga caaggctgct    420
gctcacttga agggtggtgc caagaaggtt gtgatctctg ctcctagcaa ggatgccccc    480
atgtttgttg tgggtgtcaa cgagaaggaa tacaagccag aatatgacat tgtctccaat    540
gccagttgca ctaccaactg ccttgcacct ttggctaagg tcatcaatga taggtttggc    600
attgtggagg gtctcatgac tactgtccac tcccttactg ccacccagaa gactgttgat    660
ggtccatcca tgaaggactg gagaggtgga agagctgctt cattcaacat cattcctagc    720
agcactggtg ctgccaaggc tgttggaaag gtgctcccag ctcttaatgg aaaattgact    780
ggaatggcct tcagagttcc aacagttgat gtttctgttg tggaccttac tgtaaggcta    840
gagaaagagg cctcttatga tgaaatcaaa gctgcaatca aggaggaatc agagggtaag    900
ttgaagggta tcttgggatt caccgaagat gatgtggttt ccacagactt tgttggtgac    960
agcaggtcaa gcattttcga tgccaaggct ggaattgcct tgagcaagaa ctttgtgaaa   1020
cttgtgtcgt ggtatgacaa tgaatggggt tacagctctc gtgtgattga tttgatctgc   1080
catatggctt ctgttgctta aggatttgat tgatgctggt gaaatggcct ctttagtttt   1140
tgattgaatc ataggggtat tagttttcta tggccgggag tggtcttctt gtttaattgt   1200
aatggaataa ccagagagga actgtgttat ctttgaggaa tgttgggctt ttttcgcttg   1260
acttgtcatg aatgaagaat tcaaacttta ctttttaaaa aaaaaaaaaa aaaaaaaaa    1320 aaaaaaaa                                                            1328

<210> SEQ ID NO 516
<211> LENGTH: 1344
<212> TYPE: DNA
<213> ORGANISM: Thellungiella halophila

<400> SEQUENCE: 516
gctcattttt cactgtgtaa aataccttct ctctgttaat ctcatcttca atttctctct     60
ctctcgcgta tttgattgaa aaatgactgg cgctaagatt aagatcggta tcaatggttt    120
cggaagaatc ggtcgtttgg tcgctagagt cgttcttcag agggacgatg ttgagctcgt    180
cgccgtcaac gatccgttca tcaccactga gtacatgacc tacatgttca agtacgacag    240
tgttcacggt caatggaaac accatgaact caaggtcaag gatgagaaga cccttctctt    300
cggtgagaag ccagtcactg tcttcggcat caagaaccct gaggatatcc catggggtga    360
ggctggagct gacttcgttg ttgagtctac cggtgttttc actgacaagg acaaagctgc    420
tgctcacttg aagggtggtg ccaagaaggt tgtcatctct gccccaagca aggacgctcc    480
catgtttgtt gttggtgtta acgagcacga atacaagtcc gacctagaca ttgtctccaa    540
cgccagttgc accactgact gccttgctcc ccttgccaag gttatcaacg acaggtttgg    600
aattgttgag ggtctttatga ctaccgtcca ctctatcact gctacacaga agactgttga    660
tggaccatcg atgaaggact ggagaggtgg aagagctgct tcattcaaca tcattcccag    720
cagcaccgga gctgccaagg ccgtcggaaa ggtgcttcca caactcaacg gaaagttgac    780
cggaatgtcc ttccgtgttc ccaccgttga tgtttcagtt gttgacctca cggttaggct    840
cgagaaagct gcaacctacg atgaaatcaa gaaggctatc aaggaggaat ctgaaggcaa    900
gctaaaggga atccttggtt acaccgagga tgatgttgtc tcaactgact cgttggtga    960
```

```
cagcaggtcg agcattttg acgccaaggc tggaattgcg ttgagcgaga acttcgtgaa      1020
actggtgtcg tggtatgaca acgaatgggg ttacagtacc cgtgtggtcg acttgattgt      1080
tcacatgtcc aaggcctaaa gctgagaaga aaatctcgag actgatgggg agggaggaat      1140
tcttatttct cgtcccttt aatgttctga gtttgtcgtt ttttgaataa attttcttg       1200 agatttaaaa ctcttttggt tttggcgaat ctcattcact tgagttgatg tgagtttgta      1260
gaccggttgt ttaaccgata gcccttatg tttggctttt gatatattgg atccacgtat       1320
ggtttatcaa aaaaaaaaaa aaaa                                              1344

<210> SEQ ID NO 517
<211> LENGTH: 1439
<212> TYPE: DNA
<213> ORGANISM: Arabidopsis thaliana

<400> SEQUENCE: 517
gccactcgat catatttca atttcatca tcacgttctt cttctctttt aaataacct         60 aaatcctcac caaacccaaa ccctcactca ctatttcac attctcttct ctctcgatat      120
catctaaatc tctctcgatc tcaatttcgc aaaatggctg acaagaagat cagaatcgga      180
atcaacggtt tcggaagaat cggtcgtttg gttgctagag ttgttcttca gagggatgat      240
gttgagctcg tcgctgttaa cgatcctttc atcaccaccg agtacatgac atacatgttt      300
aagtatgaca gtgttcacgg tcagtggaag caccatgagc ttaaggtgaa ggatgacaaa      360
actcttctct cggtgagaa gccagtcact gttttcggca tcaggaaccc tgaggacatc      420
ccatggggtg aggctggagc tgactttgtt gttgagtcta ctggtgtctt cactgacaaa      480
gacaaggctg ctgctcactt gaagggtggt gctaaaaagg ttgtcatctc tgccccaagc      540
aaagatgcgc ccatgttcgt tgttggtgtc aacgagcacg agtacaagtc tgaccttgac      600
attgtttcca acgctagttg caccactaac tgccttgctc ctcttgccaa ggttattaat      660
gacaggtttg gcattgttga gggactcatg accactgtcc actctatcac tgctactcag      720
aagacagttg atggtccatc aatgaaggac tggagaggtg aagagctgc ttccttcaac       780 attattccta gcagcactgg tgccgccaag gctgttggga agtgttgcc atcccctcaat       840 ggaaaattga ccggaatgtc ttttccgtgtt ccaaccgttg atgtctcagt tgttgatctc      900
accgttagac ttgagaaagc tgcaacatac gacgaaatca agaaggccat caaggaggaa      960
tctgaaggca aaatgaaggg aattttgga tacactgagg atgatgttgt gtctaccgac      1020
tttgttggtg acaacaggtc aagcattttc gatgccaagg ctgggattgc attgagcgac      1080
aagtttgtga agttggtgtc atggtacgac aacgaatggg gttacagttc tcgtgtcgtt      1140
gaccttatcg ttcacatgtc aaaggcctaa gcttacaccg gcgagagttt gtgtgtggtt      1200
gagttcgtac tgttctgaat aaaaaaaagg agaaagaaa actcgagttg ttatgttttt       1260
tcactgattc catgcgcagt catgagagtt tgtagctttt gtcttttgc tttctcttaa       1320 tgtttccctg ctttatttac tgaaaccatt ggtttggttt tttatgttaa ttaagttttt      1380
agttcattac ttttctcgtgc taactcaaac ccaactggca actggaacat tgaacgtcc       1439

<210> SEQ ID NO 518
<211> LENGTH: 1361
<212> TYPE: DNA
<213> ORGANISM: Arabidopsis lyrata subsp. lyrata

<400> SEQUENCE: 518
tttcatcatc acgttcttct tctctttta ataaccctaa agcctcacca aaccctcact         60
```

```
cactaatttc acattcttct ctctcgatat catctaaatc tctcgatctc aaatttcgaa        120
aatggctgac aagaagatca gaatcggaat caacggtttc ggaagaatcg gtcgtttggt        180
tgctagagtt gttcttcaga gggatgatgt tgagctcgtc gctgtcaacg atcctttcat        240
caccaccgag tacatgacat acatgtttaa gtatgacagt gttcatggtc agtggaagca        300
ccatgaactt aaggtcaagg atgataaaac tcttctcttc ggtgagaagc cagtcactgt        360
tttcggtatc aggaaccctg aggagatccc atggggtgag gctggagctg actttgttgt        420
tgagtctacc ggtgtgttca ctgacaagga caaggcagct gctcacttga agggtggtgc        480
taaaaaggtt gtcatctctg caccaagcaa agatgctccc atgtttgtcg ttggtgtcaa        540
cgagcatgaa tacaagtctg atcttgacat tgtttccaac gctagttgca ccactaactg        600
ccttgctcct cttgccaagg ttattaacga cagatttggt attgttgagg gactcatgac        660
cactgtccac tctatcactg ctactcagaa gactgttgat ggtccatcaa tgaaggactg        720
gagaggtgga agagctgctt ccttcaacat tattcctagc agcactggtg ccgccaaggc        780
tgttgggaaa gtgttgccat ccctcaatgg aaaattgact ggaatgtctt ccgtgttcc         840 aaccgttgat gtctcagttg ttgatctcac cgttagactt gagaaagctg caacatacga        900
tgaaatcaag aaggccatca aggaggaatc tgaaggcaaa ctgaagggaa ttttgggata        960
caccgaggat gatgttgtgt ctactgactt tgtcggtgac aaccggtcaa gcatattcga       1020
tgctaaggca gggattgcat tgagcgacaa gtttgtgaag ttggtgtcat ggtacgacaa       1080
cgagtggggt tacagttctc gtgtcgttga ccttatcgtt cacatgtcaa aggcctaagg       1140
ttacaccagc aagtgtttgt gtgttgagtc gtactgttct gaataaaaaa atttcactga       1200
ttccatgcgc agtcatgaga gtttgtagct tttttgcttt tttgctttct attaatgttt       1260
ccctgctttg aaagttgaaa ccattggttt ggttttatg ttaatgagtt tagttcattg       1320
attttcgtgg taactcaaac ccaactggca actgcaacat g                           1361
```

<210> SEQ ID NO 519
<211> LENGTH: 1420
<212> TYPE: DNA
<213> ORGANISM: Nicotiana tabacum

<400> SEQUENCE: 519

```
gcggcgcgaa ttgccggccg ccccgttgta tcaaacccct tccaccaactc tgaatccact         60 acactcttct acaaagccct tcaatcactc agtcagatcg gacttcgctc ctcctctcat        120
ttctcaaaaa tcatggccaa ggttaagatt ggaattaacg gatttggaag aattgggcga        180
ttagtggcca gggttgctct ccaaagagat gatgttgagc ttgtcgcagt taacgaccct        240
ttcatctctg ttgaatacat gacatatatg ttcaagtatg atagtgtaca cggccagtgg        300
aagcaccacg agctcaaggt taaggatgac aagacccttc tctttggtga aaggctgtt        360 actgttttg gctttaggaa cccagaggag attccatggg ccagactgg agcagattac        420 attgtggagt cgactggtgt cttcactgac aaggacaagg ctgctgctca cttgaagggt        480
ggtgccaaga aagtcatcat ttctgcccct agcaaggatg ctccgatgtt tgttgtcggt        540
gtcaatgaga aagaatacaa gcccgagctc aacattgttt caaatgctag ctgtaccaca        600
aattgccttg ctcccttggc caaggttata aatgacagat ttggaattgt tgagggtctc        660
atgaccacag tccactccat cacagccaca cagaaaactg ttgatgggcc atcagccaag        720
gactggaggg gtggaagagc tgcatcattc aatattattc cagcagtac tggagctgcc        780
```

```
aaggctgttg ggaaagtcct accagcattg aatggaaagt taaccggaat ggctttccga    840
gtcccaactg ttgatgtgtc cgtggttgac ctcacagtga ggctggagaa agaagctacc    900
tacgatgaaa tcaaggctgc cattaaggag gaatctgaag gaaaattgaa gggaattcta    960
ggttacactg aagatgatgt ggtgtccaca gacttcgtgg gagacaatag atcaagcata   1020
tttgatgcca aggctggaat tgcttttgagc aagaattttg ttaagctcgt ttcgtggtac   1080
gacaatgaat ggggttacag cacacgagtg gtggacttga ttaagcacat ggcatcagtt   1140
cagtaaaagt ggcagtttac tcattggtgg ccaagtgtag tggtgctgct gtgaggagtc   1200
tgttatttgt tactagataa agcagtttag aataaagtac tcactcggac tacaagtgag   1260
cggctctttg atgtaattta gggatatctg cactcttgga tatggtttga ggtcatcaat   1320
tgggttgttg tagacttccc cacacattcc gagacccagt cttttgcaact ctggatatgt   1380
ttcttgtttt tgttgtgtta tgaatgtgta ataagtttgg                         1420
```

<210> SEQ ID NO 520
<211> LENGTH: 1405
<212> TYPE: DNA
<213> ORGANISM: Arabidopsis thaliana
<400> SEQUENCE: 520

```
agccactcga tcatattttc aattttcatc atcacgttct tcttctcttt taaataaccc     60
taaatcctca ccaaacccaa accctcactc actattttca cattctcttc tctctcgata    120
tcatctaaaa ctctctcgat ctcaatttcg caaaatggct gacaagaaga tcagaatcgg    180
aatcaacggt ttcggaagaa tcggtcgttt ggttgctaaa gttgttcttc agagggatga    240
tgttgagctc gtcgctgtta acgatccttt catcaccacc gagtacatga catacatgtt    300
taagtatgac agtgttcacg gtcagtggaa gcaccatgag cttaaggtga aggatgacaa    360
aactcttctc ttcggtgaga agccagtcac tgttttcggc atcaggaacc ctgaggacat    420
cccatggggt gaggctggag ctgactttgt tgttgagtct actggtgtct tcactgacaa    480
agacaaggct gctgctcact tgaagggtgg tgctaaaaag gttgtcatct ctgccccaag    540
caaagatgcg cccatgttcg ttgttggtgt caacgagcac gagtacaagt ctgaccttga    600
cattgtttcc aacgctagtt gcaccactaa ctgccttgct cctcttgcca aggttattaa    660
tgacaggttt ggcattgttg agggactcat gaccactgtc cactctatca ctgctactca    720
gaagacagtt gatggtccat caatgaagga ctggagaggt ggaagagctg cttccttcaa    780
cattattcct agcagcactg gtgccgccaa ggctgttggg aaagtgttgc catccctcaa    840
tggaaaattg accggaatgt cttttccgtgt tccaaccgtt gatgtctcag ttgttgatct    900
caccgttaga cttgagaaag ctgcaacata cgacgaagtc aagaaggcca tcaaggagga    960
atctgaaggc aaaatgaagg gaattttggg atacactgag gatgatgttg tgtctaccga   1020
ctttgttggt gacaacaggt caagcatttt cgatgccaag gctgggattg cattgagcga   1080
caagtttgtg aagttggtgt catggtacga caacgaatgg ggttacagtt ctcgtgtcgt   1140
tgaccttatc gttcacatgt caaaggccta agcttacacc ggcgagagtt tgtgtgtggt   1200
tgagttcgta ctgttctgaa taaaaaaaag gagaaaagaa aactcgagtt gttatgtttt   1260
ttcactgatt ccatgcgcag tcatgagagt ttgtagcttt tgtcttttg ctttctctta   1320
atgttttcct gctttattta ctgaaaccat tggtttggtt ttttatgtta attaagtttt   1380
tagttcatta aaaaaaaaaa aaaaa                                         1405
```

```
<210> SEQ ID NO 521
<211> LENGTH: 21
<212> TYPE: DNA
<213> ORGANISM: artificial sequence
<220> FEATURE:
<223> OTHER INFORMATION: synthetic construct

<400> SEQUENCE: 521
tggaaggggc atgcagagga g                                       21

<210> SEQ ID NO 522
<211> LENGTH: 24
<212> TYPE: DNA
<213> ORGANISM: artificial sequence
<220> FEATURE:
<223> OTHER INFORMATION: synthetic construct

<400> SEQUENCE: 522
ggctagccaa ggatgacttg ccta                                    24

<210> SEQ ID NO 523
<211> LENGTH: 25
<212> TYPE: DNA
<213> ORGANISM: artificial sequence
<220> FEATURE:
<223> OTHER INFORMATION: synthetic construct

<400> SEQUENCE: 523
acatcaacgc tgctacactc aatga                                   25

<210> SEQ ID NO 524
<211> LENGTH: 25
<212> TYPE: DNA
<213> ORGANISM: artificial sequence
<220> FEATURE:
<223> OTHER INFORMATION: synthetic construct

<400> SEQUENCE: 524
acattaaagc tgctacaatc aatga                                   25

<210> SEQ ID NO 525
<211> LENGTH: 365
<212> TYPE: DNA
<213> ORGANISM: Brassica napus

<400> SEQUENCE: 525
tacattgtct ccaatgctag tcgcacaacc aactgtcggg caccttttgg taacgttatc    60
aatgatacgt ttggcattgt tgacggtctc atgaccactg tccacgccat gactgccacc   120
cagaaaactg ttgatggtcc atccatgaag gactggagag gtggaagagc tgcttcattc   180
aacatcatcc ctatcagcac tggtgcagcc aaggctgttg gaaaagtgct cccacaactt   240
aacggcaaat tgactggaat ggccttcaga gtaccaactg ctgatgtctc cgttgtcgat   300
cttactgtaa gactcgagaa agaagcctcc tatgaagaca ttaaagctgc tacaatcaat   360
gacga                                                              365

<210> SEQ ID NO 526
<211> LENGTH: 143
<212> TYPE: DNA
<213> ORGANISM: Zea mays

<400> SEQUENCE: 526
gtcattgagc gcagcgttga tgatgcggag catgtacgtc ttcccgggct tcactttcag    60
```

```
cttgaacgtg tctgcgtgca tgcatatcat aagtatggat atgagttagt ataaagaatc    120
atagccgtta gcgctcatta act                                            143

<210> SEQ ID NO 527
<211> LENGTH: 84
<212> TYPE: DNA
<213> ORGANISM: Zea mays

<400> SEQUENCE: 527
atcattgagc gcagcgttga tgagccagcc gccgtgcctc ccctgtcggc tgcggcggct     60
caccagcgct gcactcaatt acgc                                           84

<210> SEQ ID NO 528
<211> LENGTH: 181
<212> TYPE: DNA
<213> ORGANISM: Brachypodium distachyon

<400> SEQUENCE: 528
ggaagggtag gatacgttttt tgcttgcccg tggccgcgct aacattaggc ttggggacta    60
tggtgcagcc aaggatgact tgccgatcga acgatgcac aatatgcatc gatcggcgag    120
ttgttcttgg ctacatctta gctcctgccc ctcatgttag gccggcatgc ggtggtatgt   180
a                                                                   181

<210> SEQ ID NO 529
<211> LENGTH: 277
<212> TYPE: DNA
<213> ORGANISM: Brassica napus

<400> SEQUENCE: 529
gtttcaggca gtctccttgg ctatcttgac atgcttttt cttccatgtt ataccttctt     60
tctttgtatt tttcgaatcc aaataatatt ttttctata aatttactac gaaaatcctt    120
taaacaatct ctaacaaagt atgttattag aaaactacca cttttttgcat ttattacaaa  180 tgcatgtacg tggtgagtgt atgcattctt tagaaggaaa tgtcaaaggt gaatagaaga   240
atcatatttg gtagccaagg atgacttgcc tatttct                            277

<210> SEQ ID NO 530
<211> LENGTH: 85
<212> TYPE: DNA
<213> ORGANISM: Medicago truncatula

<400> SEQUENCE: 530
gaatgcagcc aagggtgatt tgccggcaga tatatatgaa tattcataga gatgcatgtg    60
tcggcaagtt cctcttggct acatt                                         85

<210> SEQ ID NO 531
<211> LENGTH: 240
<212> TYPE: DNA
<213> ORGANISM: Medicago truncatula

<400> SEQUENCE: 531
agatgaagcc aaggatgact tgccggtata atagtaattt gccacaaatc tagatagcta    60
ttagctatgt ttggatgggc ggtgagatta acaaaattac agcagcattg tgattttgtt   120
gatgctttaa agtgtagttt ttatcaaaat tacagtggtt cactgtaatt atgagaatct   180
caccgtcaat ctaaatatgc atttagtttc atttccggca ggtcatcctt cggctatatt   240
```

```
<210> SEQ ID NO 532
<211> LENGTH: 91
<212> TYPE: DNA
<213> ORGANISM: Sorghum bicolor

<400> SEQUENCE: 532
cagccaagga tgacttgccg atcgatcgat gcaaactcct ctgatgtctg atctcatcag      60
attatcgttg tcggcaagtt gttcttggct a                                    91

<210> SEQ ID NO 533
<211> LENGTH: 103
<212> TYPE: DNA
<213> ORGANISM: Sorghum bicolor

<400> SEQUENCE: 533
tggcgagagc ctgcctttgg tagccaagga tgacttgcct acatggcatt gcgagttccg      60
gttgcatggc cagttcagct gagtttgtgg gcggtcacct tgg                       103

<210> SEQ ID NO 534
<211> LENGTH: 109
<212> TYPE: DNA
<213> ORGANISM: Sorghum bicolor

<400> SEQUENCE: 534
tagccaagga tgacttgccg gcatttcttg ggtcggatga ctgagttgtt gagcctgggg      60
atgaacagac ccggatcgac ggccggccgg caagtcatct gtggctacg               109

<210> SEQ ID NO 535
<211> LENGTH: 98
<212> TYPE: DNA
<213> ORGANISM: Sorghum bicolor

<400> SEQUENCE: 535
tagccaagga tgacttgcct agctatatgc ctgagagcct gtctcttggt ggtaaatttg      60
tatgtgctga gcatataggc atgtcttcct tggctact                             98

<210> SEQ ID NO 536
<211> LENGTH: 97
<212> TYPE: DNA
<213> ORGANISM: Sorghum bicolor

<400> SEQUENCE: 536
tgatagccaa ggatgacttg cctgtgtcct ttgtgccgaa ggatcagaaa tgtgagcctt      60
tgagatagat ggttcatagg cagtctcctt ggctagc                              97

<210> SEQ ID NO 537
<211> LENGTH: 89
<212> TYPE: DNA
<213> ORGANISM: Zea mays

<400> SEQUENCE: 537
gtagccaggg atgatttgcc tgtggttcct gtcgttgcca tgccaatgcc tgtactgttc      60
gatctacggg caaatcatcc ctgctaccg                                       89

<210> SEQ ID NO 538
<211> LENGTH: 101
<212> TYPE: DNA
<213> ORGANISM: Zea mays

<400> SEQUENCE: 538
```

```
ttagccaaga atggcttgcc tatctccatt attttgttca tcgcaggaag cccttccgtg      60
atggatgaaa tgtggatgat ggcatccatt cttggctaag t                         101

<210> SEQ ID NO 539
<211> LENGTH: 104
<212> TYPE: DNA
<213> ORGANISM: Zea mays

<400> SEQUENCE: 539
ttagccaaga atggcttgcc tatctccact gtttggttcg tcttgggaga ccaccctgat      60
gatgggtgta ctgtgtggat gatggcaggc cttcttggct aagc                     104

<210> SEQ ID NO 540
<211> LENGTH: 138
<212> TYPE: DNA
<213> ORGANISM: Zea mays

<400> SEQUENCE: 540
gtagccaaga atgacttgcc tatgcacgcc ctctgttggc agttccgtcc ggcagccatg      60
gcgacggttg cacaaggtga gttttttgcgg cgtggatgat gcaatgtggc tgcatcggca   120
ggtcttcttg gctagcca                                                  138

<210> SEQ ID NO 541
<211> LENGTH: 65
<212> TYPE: DNA
<213> ORGANISM: Zea mays

<400> SEQUENCE: 541
gtagccaagg atgacttgcc ggcattatat ttcttggccc gccggcaagt catctggggc      60
tacgc                                                                 65

<210> SEQ ID NO 542
<211> LENGTH: 106
<212> TYPE: DNA
<213> ORGANISM: Zea mays

<400> SEQUENCE: 542
ttagccaaga atggcttgcc tatctccatt atttggtcca tcttcttggg agacctccct      60
catggtgtgg atggaatgtg gatggtggca ggccttctgg ctaagt                   106

<210> SEQ ID NO 543
<211> LENGTH: 126
<212> TYPE: DNA
<213> ORGANISM: Zea mays

<400> SEQUENCE: 543
gcagccaagg atgacttgcc gggtattttg agcatgcatg ttacagggga gcatatgcaa      60
tctgtttgga attttgagcc cataccgtgc ggtgcctgtc ttccggcaag ttgtccttgg    120
ctacat                                                               126
```

TRANSGENIC PLANTS WITH MODIFIED SUGAR CONTENT AND METHODS OF GENERATING SAME

CROSS-REFERENCE TO RELATED APPLICATIONS

This application is a U.S. National Stage Application of PCT/IL2013/050880, filed on Oct. 28, 2013, which claims the benefit under 35 U.S.C. § 119(3) of U.S. Provisional Application No. 61/719,415, filed on Oct. 28, 2012, which is incorporated by reference in its entirety herein.

INCORPORATION OF SEQUENCE LISTING

A computer readable form of a sequence listing is filed with this application by electronic submission and is incorporated into this application by reference in its entirety. The sequence listing is contained in the file named P34093US00_SEQ.txt, which is 164,836 bytes in size (measured in operating system MS windows) and was created on Apr. 27, 2015.

FIELD OF THE DISCLOSURE

Methods and compositions for improving plant sucrose levels or increasing sucrose to glucose ratio in a fruit of a plant are provided. Also provided are small RNAs and their target genes, and transgenic and non-transgenic uses thereof for improving plant sucrose levels or increasing sucrose to glucose ratio in a fruit of a plant.

BACKGROUND

MicroRNAs (miRNAs) are small, endogenous RNAs that regulate gene expression in plants and animals. In plants, they are processed from stem-loop regions of long primary transcripts by a Dicer-like enzyme and are loaded into silencing complexes, where they generally direct cleavage of complementary mRNAs. Although plant miRNAs have some conserved functions extending beyond development, the importance of miRNA-directed gene regulation during plant development is now becoming clear miRNAs are already known to play numerous crucial roles at each major stage of development, typically at the core of gene regulatory networks, targeting genes that are themselves regulators. So far, microRNAs have been found to be involved in plant development, regulation of abiotic and biotic stress responses and hormone signaling (Jones-Rhoades et al., 2006, *Ann. Rev. Plant Biol.*, 57:19-53).

A commonly-used approach in identifying the function of novel genes is through loss-of-function mutant screening. In many cases, functional redundancy exists between genes that are members of the same family. When this happens, a mutation in one gene member might have a reduced or even non-existing phenotype and the mutant lines might not be identified in the screening.

Using miRNAs, multiple members of the same gene family can be silenced simultaneously, giving rise to much more intense phenotypes. This approach is also superior to RNA interference (RNAi) techniques, in which typically 100-800 bp fragments of the gene of interest form a fold-back structure when expressed. These long fold-back RNAs form many different small RNAs and prediction of small RNA targets other than the perfectly complementary intended targets is therefore very difficult. miRNAs, in contrast, are produced from precursors, which are normally processed such that preferentially one single, stable small RNA is generated, thus significantly minimizing the "off-target" effect.

A second approach to functional screening is through over-expression of genes of interest and testing for their phenotypes. In many cases, attempting to over-express a gene which is under miRNA regulation results in no significant increase in the gene transcript. This can be overcome either by expressing a miRNA-resistant version of the gene or by down-regulating the miRNA itself.

Taste characteristics are a major determinant of fruit quality for both processing and fresh market tomatoes (see Stevens, M. A., 1986, "Inheritance of tomato fruit quality components," *Plant Breeding Reviews*, 4: 274-310). One of the major components of taste in tomatoes is soluble sugar content. The soluble sugar content of all known commercial cultivars of tomatoes primarily includes the hexose sugars glucose and fructose in near-equimolar ratios (1:1 to 1:1.3). In commercial tomato cultivars, the disaccharide sucrose is also present but at concentrations rarely exceeding 0.5% on a fresh weight basis. Certain wild species of tomato accumulate high concentrations of sucrose, which may reach 4% on a fresh weight basis. In the presence of high sucrose, these fruit accumulate low levels of the hexoses fructose and glucose, typically less than 1% each on a fresh weight basis and the ratio of fructose to glucose is unusually high, more than 1.5:1.

Typically, plant breeders seek to improve the sweetness component of tomato flavor by increasing total soluble solids (TSS) measured by refractometric determination of a sample of juice and expressed as Brix. This measurement, however, does not differentiate between the component sugars. Fructose is significantly sweeter than both glucose and sucrose giving a tomato with a relatively high fructose content distinct advantage in terms of superior taste characteristics.

SUMMARY

This application provides and discloses miRNAs and their target genes that are involved in controlling the levels of sucrose, glucose, and fructose and methods of modulating expression or activity of these miRNAs and target genes. This application further provides transgenic plants, plant parts, e.g., seeds, that have altered expression of these miRNAs and target genes and have increased levels of sucrose, increased sucrose to glucose ratios, increased sucrose to hexose ratios, altered carbohydrate levels, or increased Brix in fruit from transgenic plants. This application also provides methods of producing and growing transgenic plants or seeds that have increased levels of sucrose, increased sucrose to glucose ratios, increased sucrose to hexose ratios, altered carbohydrate levels, or increased Brix in fruit from transgenic plants. In specific embodiments, this application discloses miRNAs, miRNA target genes, and uses thereof to increase levels of sucrose, increase sucrose to glucose ratios, increase sucrose to hexose ratios, alter carbohydrate levels, or increase Brix in fruit from transgenic plants.

The present disclosure includes and provides for a method of increasing the sucrose level or increasing the sucrose to glucose ratio in a tomato plant by transgenically expressing a recombinant DNA construct having a heterologous promoter operably linked to a DNA encoding at least one miRNA precursor that yields a mature miR169.

The present disclosure further includes and provides for a method of increasing the sucrose level or increasing the sucrose to glucose ratio in a tomato plant by transgenically expressing a recombinant DNA construct having a heterologous promoter operably linked to at least one DNA of an miR397 target mimic, an miR528 target mimic, or an miR1110 target mimic.

The present disclosure further includes and provides for a method of increasing the sucrose level or increasing the sucrose to glucose ratio in a tomato plant by transgenically expressing a recombinant DNA construct having a heterologous promoter operably linked to at least one DNA of an miR397-, an miR528-, or an miR1110-resistant target gene, wherein the miR397-, miR528-, or miR1110-resistant target gene comprises an introduced silent mutation in a nucleotide sequence that is otherwise substantially identical to the nucleotide sequence of an endogenous gene that is natively regulated by miR397, miR528, or miR1110, and wherein said silent mutation prevents binding by a mature miR397, miR528, or miR1110 to a transcript of said miR397-, miR528-, or miR1110-resistant target gene.

The present disclosure further includes and provides for a method of modifying the carbohydrate content in an edible plant comprising transgenically expressing in an edible plant a recombinant DNA construct comprising a heterologous promoter operably linked to at least one DNA encoding at least one miRNA precursor that yields a mature miR169, miR397, miR528, or miR1110.

The present disclosure further includes and provides for a method of modifying the carbohydrate content in an edible plant comprising transgenically expressing in an edible plant a recombinant DNA construct comprising a heterologous promoter operably linked to at least one DNA of an miR397 target mimic, an miR528 target mimic, or an miR1110 target mimic.

The present disclosure further includes and provides for a method of modifying the carbohydrate content in an edible plant comprising transgenically expressing in an edible plant a recombinant DNA construct having a heterologous promoter operably linked to at least one DNA of an miR397-, an miR528-, or an miR1110-resistant target gene, wherein the miR397-, miR528-, or miR1110-resistant target gene comprises an introduced silent mutation in a nucleotide sequence that is otherwise substantially identical to the nucleotide sequence of an endogenous gene that is natively regulated by miR397, miR528, or miR1110, and wherein said silent mutation prevents binding by a mature miR397, miR528, or miR1110 to a transcript of said miR397-, miR528-, or miR1110-resistant target gene.

The present disclosure further includes and provides for a method of producing a transgenic tomato plant comprising transforming a tomato plant cell with a transgene having a heterologous promoter operably linked to at least one DNA encoding a mature miRNA having a sequence that has at least 90% sequence identity to a sequence as set forth in SEQ ID NOs: 3 or 42-255, and producing a transgenic tomato plant from said transformed cell, wherein the transgenic tomato plant has an increased sucrose level or an increased sucrose to glucose ratio compared to a control tomato plant lacking the transgene.

The present disclosure further includes and provides for a method of producing a transgenic tomato plant comprising transforming a tomato plant cell with a transgene having a heterologous promoter operably linked to at least one DNA encoding a mature miRNA having a sequence that has at least 90% sequence identity to a sequence as set forth in SEQ ID NOs: 1 or 9-35, and producing a transgenic tomato plant from said transformed cell, wherein the transgenic tomato plant has an increased sucrose level or an increased sucrose to glucose ratio compared to a control tomato plant lacking the transgene.

The present disclosure further includes and provides for a method of producing a transgenic tomato plant comprising transforming a tomato plant cell with a transgene having a heterologous promoter operably linked to at least one DNA encoding a mature miRNA having a sequence that has at least 90% sequence identity to a sequence as set forth in SEQ ID NOs: 2 or 36-41, and producing a transgenic tomato plant from said transformed cell, wherein the transgenic tomato plant has an increased sucrose level or an increased sucrose to glucose ratio compared to a control tomato plant lacking the transgene.

The present disclosure further includes and provides for a method of producing a transgenic tomato plant comprising transforming a tomato plant cell with a transgene having a heterologous promoter operably linked to at least one DNA encoding a mature miRNA having a sequence that has at least 90% sequence identity to a sequence as set forth in SEQ ID NO: 4, and producing a transgenic tomato plant from said transformed cell, wherein the transgenic tomato plant has an increased sucrose level or an increased sucrose to glucose ratio compared to a control tomato plant lacking the transgene.

The present disclosure further includes and provides for a method of producing a transgenic tomato plant comprising transforming a tomato plant cell with a transgene having a heterologous promoter operably linked to at least one DNA encoding a mature miRNA having a sequence that has at least 90% sequence identity to a sequence as set forth in SEQ ID NOs: 513-520, and producing a transgenic tomato plant from said transformed cell, wherein the transgenic tomato plant has an increased sucrose level or an increased sucrose to glucose ratio compared to a control tomato plant lacking the transgene.

The present disclosure further includes and provides for a transgenic tomato plant, or part thereof, having a transgene that encodes a mature miRNA having a sequence having at least 95% sequence identity to a sequence as set forth in SEQ ID NOs: 3 or 42-255, wherein the transgenic tomato plant has an increased sucrose level or an increased sucrose to glucose ratio compared to a non-transgenic control tomato plant.

The present disclosure further includes and provides for a transgenic tomato plant, or part thereof, having a transgene that encodes a miR397 target mimic, a miR528 target mimic, or a miR1110 target mimic, and the transgenic tomato plant has an increased sucrose level or an increased sucrose to glucose ratio compared to a non-transgenic control tomato plant.

The present disclosure further includes and provides for a transgenic tomato plant, or part thereof, having a transgene that encodes a miR397-, miR528-, or miR1110-resistant target gene, and the transgenic tomato plant has an increased sucrose level or an increased sucrose to glucose ratio compared to a non-transgenic control tomato plant.

The present disclosure further includes and provides for a transgenic tomato plant, or part thereof, having a transgene that encodes a mature miRNA having a sequence that has at least 95% sequence identity to a sequence as set forth in SEQ ID NOs: 3 or 42-255, wherein the transgenic tomato plant has an increased sucrose level or an increased total soluble solids compared to a non-transgenic control tomato plant.

The present disclosure further includes and provides for a transgenic tomato plant, or part thereof, having a transgene that encodes a miR397 target mimic, a miR528 target mimic, or a miR1110 target mimic, and the transgenic tomato plant has an increased total soluble solids compared to a non-transgenic control tomato plant.

The present disclosure further includes and provides for a transgenic tomato plant, or part thereof, having a transgene that encodes a mature miRNA having a sequence that has at least 95% sequence identity to a sequence as set forth in SEQ ID NOs: 1 or 9-35, wherein the transgenic tomato plant has a modified carbohydrate content compared to a non-transgenic control tomato plant.

The present disclosure further includes and provides for a transgenic tomato plant, or part thereof, having a transgene that encodes a mature miRNA having a sequence that has at least 95% identical to a sequence as set forth in SEQ ID NOs: 2 or 36-41, wherein the transgenic tomato plant has a modified carbohydrate content compared to a non-transgenic control tomato plant.

The present disclosure further includes and provides for a transgenic tomato plant, or part thereof, having a transgene that encodes a mature miRNA having a sequence that has at least 95% sequence identity to a sequence as set forth in SEQ ID NO: 4, wherein the transgenic tomato plant has a modified carbohydrate content compared to a non-transgenic control tomato plant.

According to an aspect of some embodiments of the present invention, there is provided a method of generating an edible plant with modified carbohydrate content, the method comprising: expressing within the plant an exogenous polynucleotide encoding a target polypeptide of miR169d, thereby generating an edible plant with modified carbohydrate content.

According to an aspect of some embodiments of the present invention, there is provided a method of generating an edible plant with modified carbohydrate content, the method comprising: expressing within the plant an exogenous polynucleotide for silencing expression miR169d or a precursor thereof, thereby generating an edible plant with modified carbohydrate content.

According to some embodiments of the invention, the expressing is effected by transforming a cell of the plant with the exogenous polynucleotide.

According to some embodiments of the invention, the transforming is effected by introducing to the plant cell a nucleic acid construct including the exogenous polynucleotide and at least one promoter capable of directing transcription of the exogenous polynucleotide in the plant cell.

According to some embodiments of the invention, the at least one promoter is a constitutive promoter.

DETAILED DESCRIPTION

Figure 1A:
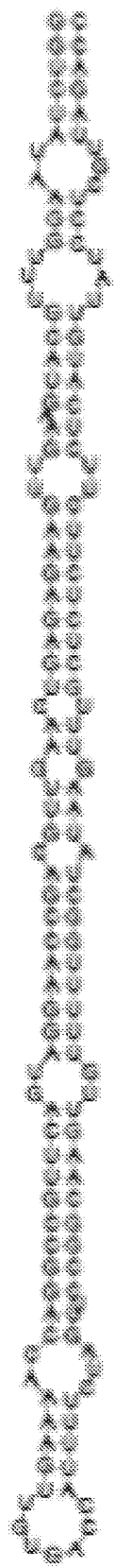
FIG. 1A is a diagram illustrating the secondary structure of a Sly-miR169d Pre-miR (SEQ ID NO: 7).
Figure 1B:
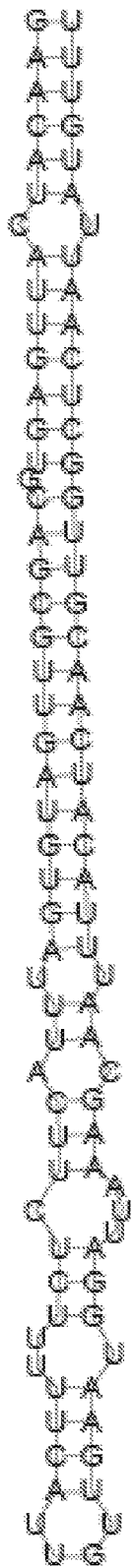
FIG. 1B is a diagram illustrating the secondary structure of a Bna-miR397a Pre-miR (SEQ ID NO: 5).
Figure 1C:
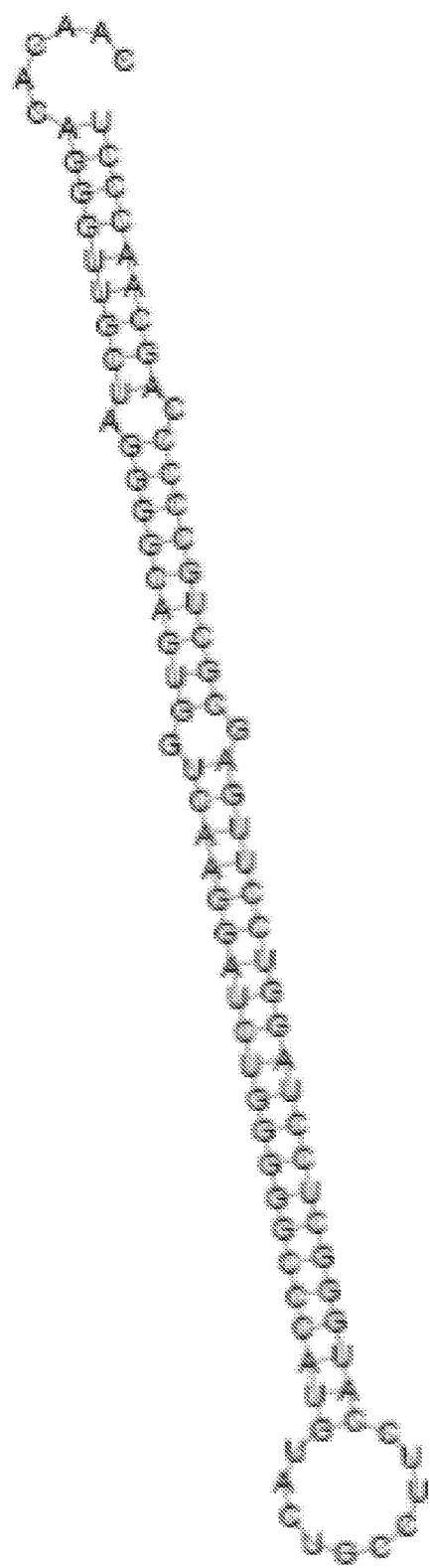
FIG. 1C is a diagram illustrating the secondary structure of a Smo-miR1110 Pre-miR (SEQ ID NO: 8).
Figure 1D:
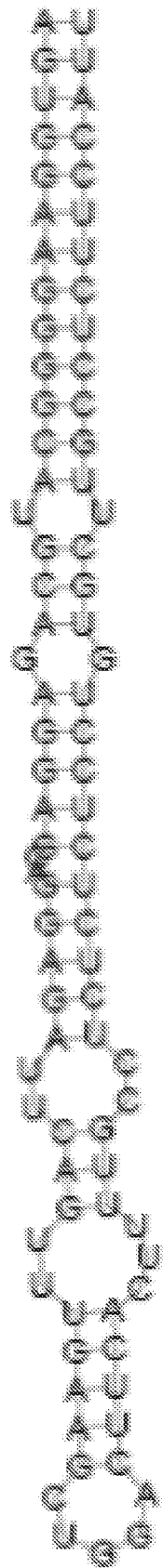
FIG. 1D is a diagram illustrating the secondary structure of a Osa-miR528 Pre-miR (SEQ ID NO: 6).

Unless defined otherwise, technical and scientific terms as used herein have the same meaning as commonly understood by one of ordinary skill in the art. One skilled in the art will recognize many methods can be used in the practice of the present disclosure. Indeed, the present disclosure is in no way limited to the methods and materials described. Any references cited herein are incorporated by reference in their entireties. For purposes of the present disclosure, the following terms are defined below.

It is understood that any Sequence Identification Number (SEQ ID NO) disclosed in the instant application can refer to either a DNA sequence or a RNA sequence, depending on the context where that SEQ ID NO is mentioned, even if that SEQ ID NO is expressed only in a DNA sequence format or a RNA sequence format. For example, SEQ ID NO: 1 is expressed in a DNA sequence format (e.g., reciting T for thymine), but it can refer to either a DNA sequence that corresponds to a mature Bna-miR397a molecule, or the RNA sequence of a mature Bna-miR397a molecule. Similarly, though SEQ ID NO: 5 is expressed in a RNA sequence format (e.g., reciting U for uracil), depending on the actual type of molecule being described, SEQ ID NO: 5 can refer to either the sequence of a RNA molecule comprising a stem-loop structure giving rise to a Bna-miR397a molecule, or the sequence of a DNA molecule that corresponds to the RNA sequence shown. In any event, both DNA and RNA molecules having the sequences disclosed with any substitutes are envisioned.

As used herein, "small RNA" refers to any RNA molecule that is about 15-30 nucleotides long, preferably 20-24 nucleotides long. A small RNA can be either double-stranded or single-stranded. Small RNA includes, without limitation, miRNA (microRNA), ta-siRNA (trans activating siRNA), siRNA, activating RNA (RNAa), nat-siRNA (natural anti-sense siRNA), hc-siRNA (heterochromatic siRNA), cis-acting siRNA, lmiRNA (long miRNA), lsiRNA (long siRNA) and easiRNA (epigenetically activated siRNA) and their respective precursors. Preferred siRNA molecules of the disclosure are miRNA molecules, ta-siRNA molecules and RNAa molecules and their respective precursors.

As used herein, the term "siRNA" (also referred to herein interchangeably as "small interfering RNA"), is a class of double-stranded RNA molecules, 20-25 nucleotides in length. Without being limited by any theory, a role of siRNA is its involvement in the RNA interference (RNAi) pathway, where it interferes with the expression of a specific gene.

As used herein, the term "microRNA" (also referred to herein interchangeably as "miRNA" or "miR") refers to a microRNA (miRNA) molecule acting as a post-transcriptional regulator. Typically, the miRNA molecules are RNA molecules of about 20 to 22 nucleotides in length which can be loaded into a RISC complex and which direct the cleavage of another RNA molecule (i.e., target), wherein the other RNA molecule comprises a nucleotide sequence essentially complementary to the nucleotide sequence of the miRNA molecule. It is understood that the combination of "miR" with a number, e.g., miR169, refers to one or more microRNAs including, without limitation, family members.

While not limited by a particular theory, a miRNA molecule is often processed from a "pre-miRNA" or as used herein a precursor of a miRNA molecule by proteins, such as DCL proteins. Pre-microRNA molecules are typically processed from pri-microRNA molecules (primary transcripts). The single stranded RNA segments flanking the pre-microRNA are important for processing of the pri-miRNA into the pre-miRNA. The cleavage site appears to be determined by the distance from the stem-ssRNA junction (Han et al., 2006, *Cell*, 125:887-901).

As used herein, a "pre-miRNA" molecule is an RNA molecule of about 100 to about 200 nucleotides, preferably about 100 to about 130 nucleotides, which can adopt a secondary structure comprising a double-stranded RNA stem and a single-stranded RNA loop (also referred to as "hairpin") and further comprising the nucleotide sequence of the miRNA (and its complement sequence) in the double-stranded RNA stem. According to a specific embodiment, the miRNA and its complement are located about 10 to about 20 nucleotides from the free ends of the miRNA double-stranded RNA stem. The length and sequence of the single-stranded loop region are not critical and may vary considerably, e.g., between 30 and 50 nt (nucleotide) in length. The complementarity between the miRNA and its complement need not be perfect and about 1 to 3 bulges of unpaired nucleotides can often be tolerated. The secondary structure adopted by an RNA molecule can be predicted by computer algorithms conventional in the art such as mFOLD. The particular strand of the double-stranded RNA stem from the pre-miRNA which is released by DCL activity and loaded onto the RISC complex is determined by the degree of complementarity at the 5' end, whereby the strand which at its 5' end is the least involved in hydrogen bonding between the nucleotides of the different strands of the cleaved dsRNA stem is loaded onto the RISC complex and will determine the sequence specificity of the target RNA molecule degradation. However, if empirically the miRNA molecule from a particular synthetic pre-miRNA molecule is not functional (because the "wrong" strand is loaded on the RISC complex), it will be immediately evident that this problem can be solved by exchanging the position of the miRNA molecule and its complement on the respective strands of the dsRNA stem of the pre-miRNA molecule.

As used herein, the term "target mimic" refers to a miR-specific inhibitor possessing at least one microRNA binding site, mimicking the microRNA target. In some embodiments, a target mimic may possess at least one nucleotide sequence comprising 6 consecutive nucleotides complementary to positions 2-8 of a corresponding small RNA. In some embodiments, the target mimic is a RNA molecule comprising a small RNA binding site modified to render it resistant to small RNA induced cleavage. In some embodiments, a variation is introduced in the nucleotide of the target sequence complementary to the nucleotides 10 or 11 of the small RNA resulting in a mismatch.

As used herein, the term "stem-loop precursor" refers to stem-loop precursor RNA structure from which the miRNA can be processed. In the case of siRNA, the precursor is typically devoid of a stem-loop structure.

As used herein, an "artificial microRNA" (amiRNA) is a type of miRNA which is derived by replacing native miRNA duplexes from a natural miRNA precursor. Generally, an artificial miRNA is a non-naturally-existing miRNA molecule produced from a pre-miRNA molecule scaffold engineered by exchanging a miRNA sequence of a naturally-existing pre-miRNA molecule for a sequence of interest which corresponds to the sequence of an artificial miRNA.

As used herein, with respect to a nucleic acid sequence, nucleic acid molecule, or a gene, the term "natural" or "native" means that the respective sequence or molecule is present in a wild-type plant cell, that has not been genetically modified or manipulated by man. A small RNA molecule naturally targeting a target gene means a small RNA molecule present in a wild-type plant cell, the cell has not been genetically modified or manipulated by man which is targeting a target gene naturally occurring in the respective plant cell.

As used herein, a "hybrid plant" refers to a plant, or a part thereof, resulting from a cross between two parent plants, wherein one or more parents are genetically engineered plants of the disclosure (transgenic plant expressing an exogenous small RNA sequence or a precursor thereof). Such a cross can occur by, for example, sexual reproduction, or in vitro nuclear fusion.

As used herein, the term "plant cell culture" refers to any type of native (naturally occurring) plant cells, plant cell lines and genetically modified plant cells, which are not assembled to form a complete plant, such that at least one biological structure of a plant is not present. Optionally, the plant cell culture of this aspect of the present disclosure may comprise a particular type of a plant cell or a plurality of different types of plant cells.

As used herein a "transgenic plant" means a plant whose genetic material has been altered from its naturally occurring composition. Alternations to genetic materials include, without limitation, the stable integration of recombinant DNA into a plant's nuclear genome. A transgenic plant as used herein further includes stable integration of recombinant DNA into the plant's chloroplast. A transgenic plant includes, without limitation, a plant developed from an originally-transformed plant cell and progeny transgenic plants from later generations or crosses of a transformed plant.

As used herein, the term "recombinant DNA" means DNA which has been genetically engineered and constructed outside of a cell.

As used herein, a "DNA construct" means a recombinant DNA having one or more of a promoter, a transcription terminator, an enhancer or other transcriptional regulatory element, post-transcriptional regulatory sequences including, for example, polyadenlyation and splicing signals. A DNA construct according to the present disclosure may further include targeting signals, for example sequences providing for homologous recombination with a target genome or sequences for intracellular target such as nuclear localization signals.

As used herein, the term "structural gene" means a DNA sequence that is transcribed into mRNA which is then translated into a sequence of amino acids characteristic of a specific polypeptide, and in one aspect, processed into one or more specific small RNA molecules of about 21 to 24 nucleotides long.

As used herein, the term "nucleotide sequence of interest" refers to any nucleotide sequence, the manipulation of which may be deemed desirable for any reason (e.g., confer improved qualities), by one of ordinary skill in the art.

As used herein, the term "expression" refers to the biosynthesis of a gene product. For example, in the case of a structural gene, expression involves transcription of the structural gene into mRNA and, optionally, the subsequent translation of mRNA into one or more polypeptides. In another example, expression may involve the transcription of a small RNA precursor and, optionally, the subsequent processing of the small RNA precursor to an miRNA, ta-siRNA, siRNA, activating RNA, nat-siRNA, hc-siRNA, cis-acting siRNA, lmiRNA, lsiRNA, easiRNA, or their respective intermediates.

As used herein, the term "heterologous" means not naturally occurring together.

As used herein, the terms "promoter," "promoter element," and "promoter sequence" refer to a DNA sequence which when ligated to a nucleotide sequence of interest is capable of controlling the transcription of the nucleotide sequence of interest into mRNA. A promoter is typically, though not necessarily, located 5' (i.e., upstream) of a nucleotide sequence of interest (e.g., proximal to the transcriptional start site of a structural gene) whose transcription into mRNA it controls, and provides a site for specific binding by RNA polymerase and other transcription factors for initiation of transcription. A repressible promoter's rate of transcription decreases in response to a repressing agent. An inducible promoter's rate of transcription increases in response to an inducing agent. A constitutive promoter's rate of transcription is not specifically regulated, though it can vary under the influence of general metabolic conditions.

As used herein, the terms "operable linkage" and "operably linked" are to be understood as meaning, for example, the sequential arrangement of a regulatory element (e.g., a promoter) with a nucleic acid sequence to be expressed and, if appropriate, further regulatory elements (such as e.g., a terminator) in such a way that each of the regulatory elements can fulfill its intended function to allow, modify, facilitate or otherwise influence expression of the nucleic acid sequence. The expression may result depending on the arrangement of the nucleic acid sequences in relation to sense or antisense RNA. To this end, direct linkage in the chemical sense is not necessarily required.

As used herein, the terms "transcription terminator" and "transcription terminator sequence" are intended to mean a sequence which leads to or initiates a stop of transcription of a nucleic acid sequence initiated from a promoter. Preferably, a transcription terminator sequences further comprises sequences which cause polyadenylation of the transcript.

As used herein, the term "transformation" refers to the introduction of genetic material (e.g., a transgene) into a cell. Transformation of a cell may be stable or transient. The term "transient transformation" or "transiently transformed" refers to the introduction of one or more transgenes into a cell in the absence of integration of the transgene into the host cell's genome. The term "transient transformant" refers to a cell which has transiently incorporated one or more transgenes.

In contrast, the terms "stable transformation" and "stably transformed" refer to the introduction and integration of one or more transgenes into the genome of a cell, preferably resulting in chromosomal integration and stable heritability through meiosis. Stable transformation of a cell may be detected by Southern blot hybridization of genomic DNA of the cell with nucleic acid sequences which are capable of binding to one or more of the transgenes. Alternatively, stable transformation of a cell may also be detected by the polymerase chain reaction of genomic DNA of the cell to amplify transgene sequences. The term "stable transformant" refers to a cell which has stably integrated one or more transgenes into the genomic DNA. Thus, a stable transformant is distinguished from a transient transformant in that, whereas genomic DNA from the stable transformant contains one or more transgenes, DNA from the transient transformant does not contain a transgene. In certain preferred embodiments, a stable transformant comprises one or more integrated transgenes that segregate together in a Mendelian fashion. Transformation also includes introduction of genetic material into plant cells in the form of plant viral vectors involving epichromosomal replication and gene expression which may exhibit variable properties with respect to meiotic stability. Stable transformation also includes introduction of genetic material into cells in the form of viral vectors involving epichromosomal replication and gene expression which may exhibit variable properties with respect to meiotic stability.

As used herein, the term "*Agrobacterium*" refers to a soil-borne, Gram-negative, rod-shaped phytopathogenic bacterium which causes crown gall. The term "*Agrobacterium*" includes, but is not limited to, the strains *Agrobacterium tumefaciens* (which typically causes crown gall in infected plants), and *Agrobacterium rhizogenes* (which causes hairy root disease in infected host plants).

As used herein, the term "heterozygous" means a genetic condition existing when two different alleles reside at a specific locus, but are positioned individually on corresponding pairs of homologous chromosomes in the cell of a diploid organism. Conversely, as used herein, the term "homozygous" means a genetic condition existing when two identical alleles reside at a specific locus, but are positioned individually on corresponding pairs of homologous chromosomes in the cell of a diploid organism.

As used herein, the terms "homology" and "identity," when used in relation to nucleic acids, describes the degree of similarity between two or more nucleotide sequences. The percentage of "sequence identity" between two sequences is determined by comparing two optimally aligned sequences over a comparison window, such that the portion of the sequence in the comparison window may comprise additions or deletions (gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. A sequence that is identical at every position in comparison to a reference sequence is said to be identical to the reference sequence and vice-versa. An alignment of two or more sequences may be performed using any suitable computer program. For example, a widely used and accepted computer program for performing sequence alignments is CLUSTALW v1.6 (Thompson, et al. Nucl. Acids Res., 22: 4673-4680, 1994).

As used herein, the term "exogenous polynucleotide" or "exogenous nucleic acid molecule" relative to a plant refers to a heterologous nucleic acid sequence which is not naturally expressed within that plant. An exogenous nucleic acid molecule may be introduced into a plant in a stable or transient manner. An exogenous nucleic acid molecule may comprise a nucleic acid sequence which is identical or partially homologous to an endogenous nucleic acid sequence of the plant.

As used herein, a "control plant" means a plant that does not contain the recombinant DNA that expresses a biomolecule (e.g., protein, small RNA, small RNA-resistant target mRNA, target mimic) that imparts an enhanced trait. Control plants are generally from same species and of the same developmental stage which is grown under the same growth conditions as the transformed plant. A suitable control plant can be a non-transgenic plant of the parental line used to generate a transgenic plant, i.e., devoid of recombinant DNA. A suitable control plant may in some cases be a progeny of a hemizygous transgenic plant line that is does not contain the recombinant DNA, known as a negative segregant.

As used herein, the term "wild-type" means, with respect to an organism, polypeptide, or nucleic acid sequence, that the organism, polypeptide, or nucleic acid sequence is naturally occurring or available in at least one naturally-occurring organism which is not changed, mutated, or otherwise manipulated by man.

As used herein, an "enhanced trait" means a characteristic of a transgenic plant that includes, but is not limited to, an enhanced agronomic trait characterized by enhanced plant morphology, physiology, growth and development, yield, nutritional enhancement, disease or pest resistance, or environmental or chemical tolerance. In more specific aspects of this disclosure, an enhanced trait is selected from the group of enhanced traits consisting of increased sucrose levels in a fruit of a plant, and increased sucrose to glucose ratios in a fruit of a plant.

As used herein the terms "biomass," "biomass of a plant," and "plant biomass" refer to the amount (e.g., measured in grams of air-dry tissue) of a tissue produced from the plant in a growing season. An increase in plant biomass can be in the whole plant or in parts thereof such as aboveground (e.g., harvestable) parts, vegetative biomass, roots and/or seeds.

As used herein the terms "vigor," "vigor of a plant," and "plant vigor" refer to the amount (e.g., measured by weight) of tissue produced by the plant in a given time. Increased vigor could determine or affect the plant yield or the yield per growing time or growing area. In addition, early vigor (e.g., seed and/or seedling) results in improved field stand.

As used herein the terms "yield," "yield of a plant," and "plant yield" refer to the amount (e.g., as determined by weight or size) or quantity (e.g., numbers) of tissues or organs produced per plant or per growing season. Increased yield of a plant can affect the economic benefit one can obtain from the plant in a certain growing area and/or growing time.

As used herein the terms "crop" and "crop of fruits" refer to the harvestable product of a plurality of plants growing in a field or greenhouse and grown according to standard horticultural methods. A crop according to the present disclosure may refer to either the fruits in the field or harvested from a plurality of plants.

As used herein, the terms "improving," "improved," "increasing," and "increased" refer to at least about 2%, at least about 3%, at least about 4%, at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, or greater increase, as compared to a control plant.

As used herein, "a reduction" of the level of an agent such as a protein or mRNA means that the level is reduced relative to a cell or organism lacking a dsRNA molecule capable of reducing the agent.

As used herein, the term "at least a partial reduction" of the level of an agent such as a protein or mRNA means that the level is reduced at least 25% relative to a cell or organism lacking a dsRNA molecule capable of reducing the agent.

As used herein, "a substantial reduction" of the level of an agent such as a protein or mRNA means that the level is reduced relative to a cell or organism lacking a dsRNA molecule capable of reducing the agent, where the reduction of the level of the agent is at least 75%.

As used herein, "an effective elimination" of an agent such as a protein or mRNA is relative to a cell or organism lacking a dsRNA molecule capable of reducing the agent, where the reduction of the level of the agent is greater than 95%. An agent, preferably a dsRNA molecule, is preferably capable of providing at least a partial reduction, more preferably a substantial reduction, or most preferably effective elimination of another agent such as a protein or mRNA, wherein the agent leaves the level of a second agent essentially unaffected, substantially unaffected, or partially unaffected.

As used herein, the terms "suppress," "repress," and "downregulate," when referring to the expression or activity of a nucleic acid molecule in a plant cell, are used equivalently herein and mean that the level of expression or activity of the nucleic acid molecule in a plant, a plant part, or plant cell after applying a method of the present disclosure is lower than its expression or activity in the plant, part of the plant, or plant cell before applying the method, or compared to a control plant lacking a recombinant nucleic acid molecule of the disclosure.

The terms "suppressed," "repressed" and "downregulated" as used herein are synonymous and mean herein lower, preferably significantly lower, expression or activity of the nucleic acid molecule to be expressed.

As used herein, a "suppression," "repression," or "downregulation" of the level or activity of an agent such as a protein, mRNA, or RNA means that the level or activity is reduced relative to a substantially identical plant, part of a plant, or plant cell grown under substantially identical conditions, lacking a recombinant nucleic acid molecule of the disclosure, for example, lacking the region complementary to at least a part of the precursor molecule of the small RNA, in a particular aspect a miRNA, the recombinant construct or recombinant vector of the disclosure. As used herein, "suppression," "repression," or "downregulation" of the level or activity of an agent, such as, for example, a preRNA, mRNA, rRNA, tRNA, snoRNA, snRNA expressed by the target gene, and/or of the protein product encoded by it, means that the amount is reduced by 10% or more, for example, 20% or more, preferably 30% or more, more preferably 50% or more, even more preferably 70% or more, most preferably 80% or more, for example, 90%, relative to a cell or organism lacking a recombinant nucleic acid molecule of the disclosure.

While not limited by a particular theory, two prevalent types of small RNAs, microRNAs (miRNAs) and small interfering RNAs (siRNAs) are similar in certain aspects and distinct in other aspects. For example, both promote specific down-regulation/silencing of a target gene through RNA interference (RNAi). Both miRNAs and siRNAs are oligonucleotides (20-24 bps) processed from longer RNA precursors by Dicer-like ribonucleases, although the source of their precursors is different (e.g., local single RNA molecules with imperfect stem-loop structures for miRNA, and long, double-stranded precursors potentially from bimolecular duplexes for snRNA). Additional characteristics that differentiate miRNAs from siRNAs are their sequence conservation level between related organisms (high in miRNAs, low to non-existent in siRNAs), regulation of genes unrelated to their locus of origin (typical for miRNAs, infrequent in siRNAs), and the genetic requirements for their respective functions are somewhat dissimilar in many organisms (Jones-Rhoades et al., 2006, *Ann. Rev. Plant Biol.*, 57:19-53). While not limited by a particular theory, despite all their differences, miRNAs and siRNAs are overall chemically and functionally similar, and both are incorporated into silencing complexes, wherein they can guide post-transcriptional repression of multiple target genes, and thus function catalytically.

Various approaches are contemplated herein to regulate, either upregulate or downregulate the expression or activity of a small RNA, including without limitation a miRNA. Upregulation of small RNA activity, including without limitation, miRNA activity, can be achieved either permanently or transiently. Nucleic acid agents that down-regulate small RNA activity include, but are not limited to, target mimics, small RNA, including without limitation miRNA, resistant target genes, and a small RNA, including without limitation a miRNA, inhibitor.

This application provides and discloses small RNAs, including without limitation miRNAs, and their target genes that are involved in controlling or modulating sucrose levels in a fruit of a plant, controlling or modulating glucose levels in a fruit of a plant, and controlling or modulating sucrose to glucose ratios in a fruit of a plant. This application further provides transgenic plants, plant parts, e.g., seeds that have altered expression of these small RNAs, including without limitation miRNAs, and target genes and have increased sucrose levels in a fruit of a plant, increased sucrose to glucose ratios in a fruit of a plant, or both. This application also provides methods of producing and growing transgenic plants or seeds that have increased sucrose levels in a fruit of a plant, increased sucrose to glucose ratios in a fruit of a plant, or both. In specific embodiments, this application discloses small RNAs, including without limitation miRNAs, small RNA target genes, including without limitation miRNA target genes, and uses thereof to increase sucrose levels in a fruit of a plant, increase sucrose to glucose ratios in a fruit of a plant or both.

In an aspect, the instant application discloses a method of increasing sucrose levels in a fruit of a plant, increasing sucrose to glucose ratios in a fruit of a plant, or both comprising transgenically expressing in the plant a recombinant DNA construct comprising encoding a small RNA including, without limitation, miRNA, ta-siRNA, siRNA, activating RNA, nat-siRNA, hc-siRNA, cis-acting siRNA, lmiRNA, lsiRNA, easiRNA or their respective intermediates and precursors. In certain aspects, the instant application discloses a method of increasing sucrose levels in a fruit of a tomato plant, increasing sucrose to glucose ratios in a fruit of a tomato plant, or both, comprising transgenically expressing in the tomato plant a recombinant DNA construct comprising encoding a small RNA including, without limitation, miRNA, ta-siRNA, siRNA, activating RNA, nat-siRNA, hc-siRNA, cis-acting siRNA, lmiRNA, lsiRNA, easiRNA, or their respective intermediates and precursors.

In aspects according to the instant application, transgene expression of a small RNA increases the sucrose level in a fruit of a plant over the level of sucrose in a fruit of a control plant lacking the transgene. In other aspects, transgene expression of a small RNA increases the sucrose level in a fruit of a plant over the level of sucrose in a fruit of a wild type plant lacking the transgene. In an aspect, a fruit of a transgenic tomato comprises more than 0.5% sucrose by fresh weight. In another aspect, a fruit of a transgenic tomato comprises more than 0.75% sucrose by fresh weight. In a further aspect, the sucrose level in a fruit of transgenic tomato may be more than 1% by weight. In an aspect, a fruit of a transgenic tomato comprises more than 1.5% sucrose by fresh weight. In other aspects, a fruit of a transgenic tomato comprises more than 2.0% sucrose by fresh weight. In yet another aspect, a transgenic tomato fruit may comprise more that 2.5% sucrose by weight. In a further aspect, a fruit of a transgenic tomato comprises more than 3.0% sucrose by fresh weight. In other aspects, a fruit of a transgenic tomato comprises more than 3.5% sucrose by fresh weight. In certain aspects, a transgenic tomato plant expressing a small RNA produces a fruit having more than 4% sucrose by fresh weight.

In aspects according to the instant disclosure, fruit of a transgenic plant expressing a recombinant DNA construct comprising encoding a small RNA including, without limitation, miRNA, ta-siRNA, siRNA, activating RNA, nat-siRNA, hc-siRNA, cis-acting siRNA, lmiRNA, lsiRNA, easiRNA or their respective intermediates may have more than 0.5% sucrose by fresh weight. In another aspect, the fruit may comprise more than 0.75% sucrose by fresh weight. In an aspect, the sucrose level in a fruit of transgenic plant may be more than 1% by weight. In an aspect, a fruit of a transgenic plant comprises more than 1.5% sucrose by fresh weight. In other aspects, a fruit may comprise more than 2.0% sucrose by fresh weight or more than 2.5% sucrose by weight. In a further aspect, a fruit of a transgenic plant comprises more than 3.0% sucrose by fresh weight. In other aspects, a fruit of a transgenic plant comprises more than 3.5% sucrose by fresh weight. In certain aspects, a transgenic plant expressing a small RNA produces a fruit having more than 4% sucrose by fresh weight.

In aspects according to the instant application, transgene expression of a small RNA increases the sucrose level in a fruit of a plant over the level of sucrose in a fruit of a control plant lacking the transgene. In other aspects, transgene expression of a small RNA increases the sucrose level in a fruit of a plant over the level of sucrose in a fruit of a wild type plant lacking the transgene. In an aspect, a fruit of a transgenic tomato comprises more than 5 milligrams sucrose per gram of fresh fruit. In another aspect, a fruit of a transgenic tomato comprises more than more than 6 milligrams sucrose per gram of fresh fruit or more than 7 milligrams sucrose per gram of fresh fruit. In other aspects, the fruit may be more than 8 or more than 9 milligrams sucrose per gram of fresh fruit. In some aspects, the sucrose per gram of fresh fruit may be more than 10 or 15 milligrams. In some aspects the sucrose may be more than 20, more than 25 or more than 30 milligrams per gram of fresh fruit. In some aspects, the transgenic fruit may have 40 or more milligrams sucrose per gram of fresh fruit.

In aspects according to the instant disclosure, transgene expression of a small RNA increases the ratio of sucrose to glucose in a fruit of a plant over the level of sucrose in a fruit of a control plant lacking the transgene. In other aspects, transgene expression of a small RNA increases the ratio of sucrose to glucose in a fruit of a plant over the ratio of sucrose to glucose in a fruit of a wild type plant lacking the transgene. In aspects according to the instant disclosure, transgene expression of a small RNA increases the ratio of sucrose to hexose (e.g., fructose and glucose) in a fruit of a plant over the ratio of sucrose to hexose in a fruit of a control plant lacking the transgene. In other aspects, transgene expression of a small RNA increases the ratio of sucrose to hexose in a fruit of a plant over the ratio of sucrose to glucose in a fruit of a wild type plant lacking the transgene.

In aspects according to the instant disclosure, transgene expression of a small RNA increases the ratio of sucrose to glucose in a fruit of a transgenic plant to be greater than 0.14. In an aspect the sucrose to glucose ratio in a transgenic plant to be greater than 0.15 or 0.16. In another aspect, the sucrose to glucose ratio in a transgenic plant may be greater than 0.17, 0.18, or 0.19. In an aspect the sucrose to glucose ratio in a transgenic plant may be greater than 0.20 or 0.25. In another aspect, the sucrose to glucose ratio in a transgenic plant may be greater than 0.3, 0.4, or 0.5. In another aspect, the sucrose to glucose ratio in a fruit of a transgenic plant may be greater than 0.3, 0.4, or 0.5. In other aspects, the sucrose to glucose ratio may be from 0.16 to 0.20, 0.16 to 0.25, 0.16 to 0.30, or 0.16 to 0.35. In yet other aspects, the sucrose to glucose ratio may be from 0.17 to 0.20, 0.17 to 0.25, 0.17 to 0.30, or 0.17 to 0.35. In yet other aspects, the sucrose to glucose ratio may be from 0.18 to 0.20, 0.18 to 0.25, 0.18 to 0.30, or 0.18 to 0.35.

In aspects according to the instant disclosure, transgene expression of a small RNA increases the ratio of sucrose to hexose in a fruit of a transgenic plant may be greater than 0.06. In an aspect the sucrose to hexose ratio in a transgenic plant may be greater than 0.07 or 0.08. In another aspect, the sucrose to hexose ratio in a transgenic plant may be greater than 0.9, 0.10, or 0.15. In an aspect the sucrose to hexose ratio in a transgenic plant may be greater than 0.20 or 0.25. In another aspect, the sucrose to hexose ratio in a fruit of a transgenic plant may be greater than 0.3, 0.4, or 0.5. In other aspects, the sucrose to hexose ratio may be from 0.06 to 0.10, 0.07 to 0.10, 0.09 to 0.15, or 0.10 to 0.15. In yet other aspects, the sucrose to hexose ratio may be from 0.08 to 0.10, 0.08 to 0.15, 0.08 to 0.2, or 0.08 to 0.25.

In aspects according to the instant application, transgene expression of a small RNA increases the carbohydrate level as measured by total soluble solids (e.g., Brix) in a fruit of a plant over the carbohydrate level as measured by total soluble solids in a fruit of a control plant lacking the transgene. In other aspects, transgene expression of a small RNA the carbohydrate level as measured by total soluble solids in a fruit of a plant over the carbohydrate level as measured by total soluble solids in a fruit of a wild type plant lacking the transgene. In an aspect, the Brix of a fruit of a transgenic tomato increases at least 5% over the Brix of a fruit from a control plant lacking the transgene. In an aspect, the Brix of a fruit of a transgenic tomato increases at least 7.5% over the Brix of a fruit from a control plant lacking the transgene. In an aspect, the Brix of a fruit of a transgenic tomato increases at least 10% over the Brix of a fruit from a control plant lacking the transgene. In an aspect, the Brix of a fruit of a transgenic tomato increases at least 15% over the Brix of a fruit from a control plant lacking the transgene. In an aspect, the Brix of a fruit of a transgenic tomato increases at least 20% over the Brix of a fruit from a control plant lacking the transgene. In an aspect, the Brix of a fruit of a transgenic tomato increases at least 30% over the Brix of a fruit from a control plant lacking the transgene. In an aspect, the Brix increases by 40%, 50%, or more over the Brix of a fruit from a plant lacking the transgene. In an aspect, the Brix increases by 60%, 70%, or more over the Brix of a fruit from a plant lacking the transgene. In other aspects, the Brix increases by 100% or more. In another aspect, the Brix increases 1.5× or more over the Brix of a fruit from a plant lacking the transgene. In an aspect, the Brix increases 2.0×, 2.5×, or more over the Brix of a fruit from a plant lacking the transgene.

In aspects according to the instant disclosure, fruit of a transgenic plant expressing a recombinant DNA construct encoding a small RNA including, without limitation, miRNA, ta-siRNA, siRNA, activating RNA, nat-siRNA, hc-siRNA, cis-acting siRNA, lmiRNA, lsiRNA, easiRNA or their respective intermediates may have more than 0.5% sucrose by fresh weight. In another aspect, the fruit may comprise more than 0.75% sucrose by fresh weight. In an aspect, the sucrose level in a fruit of transgenic plant may be more than 1% by weight. In an aspect, a fruit of a transgenic plant comprises more than 1.5% sucrose by fresh weight. In other aspects, a fruit may comprise more than 2.0% sucrose by fresh weight or more than 2.5% sucrose by weight. In a further aspect, a fruit of a transgenic plant comprises more than 3.0% sucrose by fresh weight. In other aspects, a fruit of a transgenic plant comprises more than 3.5% sucrose by fresh weight. In certain aspects, a transgenic plant expressing a small RNA produces a fruit having more than 4% sucrose by fresh weight.

In aspects according to the instant disclosure, transgenic plants expressing small RNA may produce a crop of fruit having an average of more than 5.0 mg sucrose/g fresh fruit. In other aspects, the transgenic plants of the instant disclosure may produce a crop of fruit having an average of more than 7.5 mg sucrose/g fresh fruit. In an aspect, the transgenic plants of the instant disclosure may produce a crop of fruit having an average of more than 10.0 m g sucrose/g fresh fruit. In an aspect, the transgenic plants of the instant disclosure may produce a crop of fruit having an average of more than 15.0 mg sucrose/g fresh fruit. In an aspect, the transgenic plants of the instant disclosure may produce a crop of fruit having an average of more than 20.0 mg sucrose/g fresh fruit. In an aspect, the transgenic plants of the instant disclosure may produce a crop of fruit having an average of more than 25.0 mg sucrose/g fresh fruit. In an aspect, the transgenic plants of the instant disclosure may produce a crop of fruit having an average of more than 30.0 mg sucrose/g fresh fruit. In an aspect, the transgenic plants of the instant disclosure may produce a crop of fruit having an average of more than 35.0 mg sucrose/g fresh fruit. In an aspect, the transgenic plants of the instant disclosure may produce a crop of fruit having an average of more than 40.0 mg sucrose/g fresh fruit.

In aspects according to the instant disclosure, a crop of fruits from transgenic plants expressing a recombinant DNA construct comprising a small RNA may have an average of 5 to 10 mg sucrose/g fresh fruit. In an aspect, a crop of fruits from transgenic plants expressing a recombinant DNA construct encoding a small RNA may have an average of 5 to 15 mg sucrose/g fresh fruit or 5 to 25 mg sucrose/g fresh fruit. In an aspect, a crop of fruits from transgenic plants expressing a recombinant DNA construct comprising a small RNA may have an average of 5 to 30 mg sucrose/g fresh fruit or 5 to 35 mg sucrose/g fresh fruit. In other aspects the average amount of sucrose in the fruit of a crop obtained from transgenic plants according to the instant disclosure may be from 10 to 20, 10 to 30, or 10 to 40 mg sucrose/g fresh fruit. In other aspects the average amount of sucrose in the fruit of a crop obtained from transgenic plants according to the instant disclosure may be from 20 to 30, 20 to 35, or 20 to 40 mg sucrose/g fresh fruit.

In aspects according to the instant disclosure, transgene expression of a small RNA increases the average ratio of sucrose to glucose in a crop of fruits from transgenic plants to be greater than 0.14. In an aspect the average sucrose to glucose ratio of a crop of fruit from transgenic plants is greater than 0.15 or 0.16. In another aspect, the average sucrose to glucose ratio a crop of fruits from transgenic plants may be greater than 0.17, 0.18, or 0.19. In an aspect the average sucrose to glucose ratio a crop of fruits from transgenic plants may be greater than 0.20 or 0.25. In another aspect, the average sucrose to glucose ratio a crop of fruits from transgenic plants may be greater than 0.3, 0.4, or 0.5. In another aspect, the average sucrose to glucose ratio a crop of fruits from transgenic plants may be greater than 0.3, 0.4, or 0.5. In other aspects, the average sucrose to glucose ratio may be from 0.16 to 0.20, 0.16 to 0.25, 0.16 to 0.30, or 0.16 to 0.35. In yet other aspects, the average sucrose to glucose ratio may be from 0.17 to 0.20, 0.17 to 0.25, 0.17 to 0.30, or 0.17 to 0.35. In yet other aspects, the average sucrose to glucose ratio may be from 0.18 to 0.20, 0.18 to 0.25, 0.18 to 0.30, or 0.18 to 0.35.

In aspects according to the instant disclosure, transgene expression of a small RNA increases the average ratio of sucrose to hexose in a crop of fruits from transgenic plants may be greater than 0.06. In an aspect the average sucrose to hexose ratio in a crop of fruits from transgenic plants may be greater than 0.07 or 0.08. In another aspect, the average sucrose to hexose ratio in a crop of fruits from transgenic plants may be greater than 0.9, 0.10, or 0.15. In an aspect the average sucrose to hexose ratio in a crop of fruits from transgenic plants may be greater than 0.20 or 0.25. In another aspect, the average sucrose to hexose ratio in a crop of fruits from transgenic plants may be greater than 0.3, 0.4, or 0.5. In other aspects, the average sucrose to hexose ratio may be from 0.06 to 0.10, 0.07 to 0.10, 0.09 to 0.15, or 0.10 to 0.15. In yet other aspects, the average sucrose to hexose ratio may be from 0.08 to 0.10, 0.08 to 0.15, 0.08 to 0.2, or 0.08 to 0.25.

In aspects according to the instant application, transgene expression of a small RNA increases the average carbohydrate level as measured by total soluble solids (e.g., Brix) in a crop of fruits from transgenic plants over the average carbohydrate level as measured by total soluble solids in a crop of fruits from control plants lacking the transgene. In other aspects, transgene expression of a small RNA increases the average carbohydrate level as measured by total soluble solids in a crop of fruits from transgenic plants over the average carbohydrate level as measured by total soluble solids in a crop of fruit of a wild type plants lacking the transgene. In an aspect, the average Brix in a crop of fruits from transgenic plants increases at least 5% over the average Brix of a crop of fruits from control plants lacking the transgene. In an aspect, the average Brix in a crop of fruits from transgenic plants increases at least 7.5% over the average Brix of non-transgenic crop fruit from a control plant. In an aspect, the average Brix in a crop of fruits from transgenic plants increases at least 10% over the Brix of a crop of fruit from control plants lacking the transgene. In an aspect, the average Brix in a crop of fruits from transgenic plants increases at least 15% over the average Brix of a crop of fruit from control plants lacking the transgene. In an aspect, the average Brix in a crop of fruits from transgenic plants increases at least 20% over the average Brix of a crop of fruit from control plants lacking the transgene. In an aspect, the average Brix in a crop of fruits from transgenic plants tomato increases at least 30% over the average Brix of a fruit crop from control plants lacking the transgene. In an aspect, the average Brix increases by 40%, 50%, or more over the average Brix of a fruit crop from plants lacking the transgene. In an aspect, the average Brix increases by 60%, 70%, or more over the average Brix of a fruit crop from plants lacking the transgene. In other aspects, the average Brix increases by 100% or more. In another aspect, the average Brix increases 1.5× or more over the average Brix of a crop of fruit from plants lacking the transgene. In an aspect, the average Brix increases 2.0×, 2.5×, or more over the average Brix of a fruit crop from plants lacking the transgene.

In one aspect, the instant application discloses a method of increasing sucrose levels in a fruit of a plant, increasing sucrose to glucose ratios in a fruit of a plant, or both, comprising transgenically expressing in the plant a recombinant DNA construct comprising a heterologous promoter operably linked to a DNA encoding at least one miRNA precursor that yields a mature miRNA. In another aspect, the instant application discloses a method of increasing sucrose levels in a fruit of a plant, increasing sucrose to glucose ratios in a fruit of a tomato plant, or both, comprising transgenically expressing in the plant a recombinant DNA construct comprising a heterologous promoter operably linked to a DNA encoding at least one miRNA precursor that yields a mature miRNA. In certain aspects, a recombinant DNA construct may further comprise a transcription terminator. In certain aspects, a DNA encoding at least one miRNA precursor comprises a nucleotide sequence having at least 80%, 85%, 88%, 90%, 92%, 95%, 96%, 97%, 98%, or 99% sequence identity to a sequence selected from the group consisting of SEQ ID NOs: 3 and 42-255. In another aspect, a DNA encoding at least one miRNA precursor comprises a nucleotide sequence selected from the group consisting of SEQ ID NOs: 3 and 42-255.

In one aspect, the instant application discloses a method of increasing sucrose levels in a fruit of a plant, increasing sucrose to glucose ratios in a fruit of a plant, or both, comprising transgenically expressing in the plant a recombinant DNA construct comprising a heterologous promoter operably linked to a DNA encoding at least one miRNA precursor that yields a mature miR169. In another aspect, the instant application discloses a method of increasing sucrose levels in a fruit of a plant, increasing sucrose to glucose ratios in a fruit of a tomato plant, or both, comprising transgenically expressing in the plant a recombinant DNA construct comprising a heterologous promoter operably linked to a DNA encoding at least one miRNA precursor that yields a mature miR169. In certain aspects, a recombinant DNA construct may further comprise a transcription terminator. In certain aspects, a DNA encoding at least one miRNA precursor that yields a mature miR169 comprises a nucleotide sequence having at least 80%, 85%, 88%, 90%, 92%, 95%, 96%, 97%, 98%, or 99% sequence identity to a sequence selected from the group consisting of SEQ ID NOs: 3 and 42-255. In another aspect, a DNA encoding at least one miRNA precursor that yields a mature miR169 comprises a nucleotide sequence selected from the group consisting of SEQ ID NOs: 3 and 42-255.

In one aspect, the instant application discloses a method of increasing sucrose levels in a fruit of a plant, increasing sucrose to glucose ratios in a fruit of a plant, or both, comprising transgenically expressing in the plant a recombinant DNA construct comprising a heterologous promoter operably linked to a DNA encoding a miR169 target mimic. In another aspect, the instant application discloses a method of increasing sucrose levels in a fruit of a plant, increasing sucrose to glucose ratios in a fruit of a tomato plant, or both, comprising transgenically expressing in the plant a recombinant DNA construct comprising a heterologous promoter operably linked to a DNA encoding a miR169 target mimic. In certain aspects, a recombinant DNA construct may further comprise a transcription terminator. In certain aspects, a DNA encoding a miR169 target mimic comprises a nucleotide sequence having at least 80%, 85%, 88%, 90%, 92%, 95%, 96%, 97%, 98%, or 99% sequence identity to a sequence selected from the group consisting of SEQ ID NOs: 3 and 42-255. In another aspect, a DNA encoding at least one miRNA precursor that yields a miR169 target mimic comprises a nucleotide sequence selected from the group consisting of SEQ ID NOs: 3 and 42-255.

In one aspect, the instant application discloses a method of increasing sucrose levels in a fruit of a plant, increasing sucrose to glucose ratios in a fruit of a plant, or both, comprising transgenically expressing in the plant a recombinant DNA construct comprising a heterologous promoter operably linked to a DNA encoding a miR528 target mimic. In another aspect, the instant application discloses a method of increasing sucrose levels in a fruit of a plant, increasing sucrose to glucose ratios in a fruit of a tomato plant, or both, comprising transgenically expressing in the plant a recombinant DNA construct comprising a heterologous promoter operably linked to a DNA encoding a miR528 target mimic. In certain aspects, a recombinant DNA construct may further comprise a transcription terminator. In certain aspects, a DNA encoding a miR528 target mimic comprises a nucleotide sequence having at least 80%, 85%, 88%, 90%, 92%, 95%, 96%, 97%, 98%, or 99% sequence identity to a sequence selected from the group consisting of SEQ ID NOs: 2 or 36-41. In another aspect, a DNA encoding at least one miRNA precursor that yields a miR528 target mimic comprises a nucleotide sequence selected from the group consisting of SEQ ID NOs: 2 or 36-41.

In one aspect, the instant application discloses a method of increasing sucrose levels in a fruit of a plant, increasing sucrose to glucose ratios in a fruit of a plant, or both, comprising transgenically expressing in the plant a recombinant DNA construct comprising a heterologous promoter operably linked to a DNA encoding a miR1110 target mimic. In another aspect, the instant application discloses a method of increasing sucrose levels in a fruit of a plant, increasing sucrose to glucose ratios in a fruit of a tomato plant, or both, comprising transgenically expressing in the plant a recombinant DNA construct comprising a heterologous promoter operably linked to a DNA encoding a miR1110 target mimic. In certain aspects, a recombinant DNA construct may further comprise a transcription terminator. In certain aspects, a DNA encoding a miR1110 target mimic comprises a nucleotide sequence having at least 80%, 85%, 88%, 90%, 92%, 95%, 96%, 97%, 98%, or 99% sequence identity to a sequence selected from the group consisting of SEQ ID NO: 4. In another aspect, a DNA encoding at least one miRNA precursor that yields a miR1110 target mimic comprises a nucleotide sequence selected from the group consisting of SEQ ID NO: 4.

In a further aspect, the instant application discloses a method of increasing sucrose levels in a fruit of a plant, increasing sucrose to glucose ratios in a fruit of a plant, or both, comprising transgenically expressing in the plant a recombinant DNA construct comprising a heterologous promoter operably linked to a DNA encoding a miR397-, miR528-, or miR1110-resistant target gene, wherein the miR397-, miR528-, or miR1110-resistant target gene comprises an introduced silent mutation in a nucleotide sequence that is otherwise substantially identical to the nucleotide sequence of an endogenous gene that is natively regulated by miR397, miR528, or miR1110, and wherein the silent mutation prevents binding by a mature miR397, miR528, or miR1110 to a transcript of the miR397, miR528-, or miR1110-resistant target gene. In certain aspects, a recombinant DNA construct may further comprise a transcription terminator. In certain aspects, a DNA encoding a miR397-resistant target gene comprises a nucleotide sequence having at least 80%, 85%, 88%, 90%, 92%, 95%, 96%, 97%, 98%, or 99% sequence identity to a sequence selected from the group consisting of SEQ ID NOs: 513-520 and 523-525.

In one aspect, a heterologous promoter used herein is selected from the group consisting of a constitutive promoter, a tissue-specific promoter, and an inducible promoter. In one aspect, a constitutive promoter is the CaMV 35S promoter. In another aspect, a promoter is an abiotic stress inducible promoter.

In one aspect, a method of improving abiotic stress tolerance in a soybean plant disclosed herein further involves transgenically expressing a recombinant DNA construct encoding a protein that provides tolerance to an herbicide selected from the group consisting of glyphosate, 2,4-dichloropropionic acid, bromoxynil, sulfonylurea, imidazolinone, triazolopyrimidine, pyrimidyloxybenzoates, phthalide, bialaphos, phosphinothricin, glufosinate, atrazine, dicamba, cyclohexanedione (sethoxydim), and aryloxyphenoxypropionate (haloxyfop). A recombinant DNA construct providing herbicide resistance and a recombinant DNA construct providing abiotic stress tolerance disclosed herein can be part of a single transgene which has a single site in the genome, or belong to separate transgenes that are located at different sites in the genome.

In another aspect, the instant application discloses a method of producing a transgenic plant, the method comprising transforming a plant cell with a transgene comprising a heterologous promoter operably linked to at least one DNA encoding a mature miRNA, comprising a sequence having at least 80%, 85%, 88%, 90%, 92%, 95%, 96%, 97%, 98%, or 99% sequence identity to a sequence selected from the group consisting of SEQ ID NOs: 3 and 42-255, and producing a transgenic plant from the transformed cell, wherein the transgenic plant has increased sucrose levels, increased sucrose to glucose ratios, or both, compared to a control plant lacking the transgene. In certain aspects, the transgene may further comprise a transcription terminator sequence.

In another aspect, the instant application discloses a method of producing a transgenic tomato plant, the method comprising transforming a tomato plant cell with a transgene comprising a heterologous promoter operably linked to at least one DNA encoding a mature miRNA, comprising a sequence having at least 80%, 85%, 88%, 90%, 92%, 95%, 96%, 97%, 98%, or 99% sequence identity to a sequence selected from the group consisting of SEQ ID NOs: 3 or 42-255, and producing a transgenic tomato plant from the transformed cell, wherein the transgenic tomato plant has increased sucrose levels, increased sucrose to glucose ratios, or both, compared to a control tomato plant lacking the transgene. In certain aspects, the transgene may further comprise a transcription terminator sequence.

In another aspect, the instant application discloses a method of producing a transgenic plant, the method comprising transforming a plant cell with a transgene comprising a heterologous promoter operably linked to at least one DNA encoding a mature miRNA, comprising a sequence having at least 80%, 85%, 88%, 90%, 92%, 95%, 96%, 97%, 98%, or 99% sequence identity to a sequence selected from the group consisting of SEQ ID NOs: 3 or 42-255, and producing a transgenic plant from the transformed cell, wherein the transgenic plant has increased sucrose levels, increased sucrose to glucose ratios, or both compared to a control plant lacking the transgene. In certain aspects, the transgene may further comprise a transcription terminator sequence.

In another aspect, the instant application discloses a method of producing a transgenic tomato plant, the method comprising transforming a tomato plant cell with a transgene comprising a heterologous promoter operably linked to at least one DNA encoding a mature miRNA, comprising a sequence having at least 80%, 85%, 88%, 90%, 92%, 95%, 96%, 97%, 98%, or 99% sequence identity to a sequence selected from the group consisting of SEQ ID NOs: 3 or 42-255, and producing a transgenic tomato plant from the transformed tomato cell, wherein the transgenic tomato plant has increased sucrose levels, increased sucrose to glucose ratios, or both, compared to a control tomato plant lacking the transgene. In certain aspects, the transgene may further comprise a transcription terminator sequence.

In another aspect, the instant application discloses a method of producing a transgenic plant, the method comprising transforming a plant cell with a transgene comprising a heterologous promoter operably linked to at least one DNA encoding a pre-miRNA or target mimic RNA, comprising a sequence having at least 80%, 85%, 88%, 90%, 92%, 95%, 96%, 97%, 98%, or 99% sequence identity to a sequence selected from the group consisting of SEQ ID NOs: 1, 2, 4, 9-41, and 523-525, and producing a transgenic plant from the transformed cell, wherein the transgenic plant has increased sucrose levels, increased sucrose to glucose ratios, or both, compared to a control plant lacking the transgene. In certain aspects, the transgene may further comprise a transcription terminator sequence.

In another aspect, the instant application discloses a method of producing a transgenic tomato plant, the method comprising transforming a tomato plant cell with a transgene comprising a heterologous promoter operably linked to at least one DNA encoding a pre-miRNA or target mimic RNA, comprising a sequence having at least 80%, 85%, 88%, 90%, 92%, 95%, 96%, 97%, 98%, or 99% sequence identity to a sequence selected from the group consisting of SEQ ID NOs: 1, 2, 4, 9-41, and 523-525, and producing a transgenic tomato plant from the transformed cell, wherein the transgenic tomato plant has increased sucrose levels, increased sucrose to glucose ratios, or both, compared to a control tomato plant lacking the transgene. In certain aspects, the transgene may further comprise a transcription terminator sequence.

In another aspect, the instant application discloses a method of producing a transgenic plant, the method comprising transforming a plant cell with a transgene comprising a heterologous promoter operably linked to at least one DNA having at least 80%, 85%, 88%, 90%, 92%, 95%, 96%, 97%, 98%, or 99% sequence identity to a sequence selected from the group consisting of SEQ ID NOs: 513-520, and producing a transgenic plant from the transformed cell, wherein the transgenic plant has increased sucrose levels, increased sucrose to glucose ratios, or both, compared to a control plant lacking the transgene. In certain aspects, the transgene may further comprise a transcription terminator sequence.

In another aspect, the instant application discloses a method of producing a transgenic tomato plant, the method comprising transforming a tomato plant cell with a transgene comprising a heterologous promoter operably linked to at least one DNA having at least 80%, 85%, 88%, 90%, 92%, 95%, 96%, 97%, 98%, or 99% sequence identity to a sequence selected from the group consisting of SEQ ID NOs: 513-520, and producing a transgenic tomato plant from the transformed cell, wherein the transgenic tomato plant has increased sucrose levels, increased sucrose to glucose ratios, or both, compared to a control tomato plant lacking the transgene. In certain aspects, the transgene may further comprise a transcription terminator sequence.

In one aspect, the instant application discloses a transgenic plant, or part thereof, comprising a transgene that encodes a mature miRNA comprising a sequence having at least 80%, 85%, 88%, 90%, 92%, 95%, 96%, 97%, 98%, or 99% sequence identity to a sequence selected from the group consisting of SEQ ID NOs: 3 and 42-255, wherein the transgenic plant has increased sucrose levels, increased sucrose to glucose ratios, or both, compared to a non-transgenic control plant.

In another aspect, the instant application discloses a transgenic plant, or part thereof, comprising a transgene that encodes a miR397 target mimic, a miR528 target mimic, or a miR1110 target mimic, and the transgenic plant has increased sucrose levels, increased sucrose to glucose ratios, or both, compared to a non-transgenic control plant.

In another aspect, the instant application discloses a transgenic tomato plant, or part thereof, comprising a transgene that encodes a miR397 target mimic, a miR528 target mimic, or a miR1110 target mimic, and the transgenic tomato plant has increased sucrose levels, increased sucrose to glucose ratios, or both, compared to a non-transgenic control tomato plant.

In a further aspect, the instant application discloses a transgenic plant, or part thereof, comprising a transgene that encodes a miR397-, miR528-, or miR1110-resistant target gene, wherein the miR397-, miR528-, or miR1110-resistant target gene comprises a sequence having at least 80%, 85%, 88%, 90%, 92%, 95%, 96%, 97%, 98%, or 99% sequence identity to a sequence selected from the group consisting of SEQ ID NOs: 513-520, and the transgenic plant has increased sucrose levels, increased sucrose to glucose ratios, or both, compared to a non-transgenic control plant.

In a further aspect, the instant application discloses a transgenic tomato plant, or part thereof, comprising a transgene that encodes a miR397-, miR528-, or miR1110-resistant target gene, wherein the miR397-, miR528-, or miR1110-resistant target gene comprises a sequence having at least 80%, 85%, 88%, 90%, 92%, 95%, 96%, 97%, 98%, or 99% sequence identity to a sequence selected from the group consisting of SEQ ID NOs: 513-520, and the transgenic tomato plant has increased sucrose levels, increased sucrose to glucose ratios, or both, compared to a non-transgenic control tomato plant.

In one aspect, the instant application discloses a method of producing a transgenic plant, the method comprising transforming a plant cell with a transgene comprising a sequence having at least 80%, 85%, 88%, 90%, 92%, 95%, 96%, 97%, 98%, or 99% sequence identity to a sequence selected from the group consisting of SEQ ID NOs: 1 to 4, 9 to 255, 513 to 520, and 523-525, and producing a transgenic plant from the transformed cell, wherein the transgenic plant has increased sucrose levels, increased sucrose to glucose ratios, or both, compared to a control plant lacking the transgene.

In one aspect, the instant application discloses a method of producing a transgenic plant, the method comprising transforming a plant cell with a transgene encoding a polypeptide sequence having at least 80%, 85%, 88%, 90%, 92%, 95%, 96%, 97%, 98%, or 99% sequence identity to a sequence selected from the group consisting of SEQ ID NOs: 503-512, and producing a transgenic plant from the transformed cell, wherein the transgenic plant has increased sucrose levels, increased sucrose to glucose ratios, or both, compared to a control plant lacking the transgene.

In one aspect, the instant application discloses a method of producing a transgenic plant, the method comprising transforming a plant cell with a transgene encoding a small RNA comprising a sequence having at least 80%, 85%, 88%, 90%, 92%, 95%, 96%, 97%, 98%, or 99% sequence identity to a sequence selected from the group consisting of SEQ ID NOs: 1 to 4, 9 to 255, 513 to 520, and 523-525, and producing a transgenic plant from the transformed cell, wherein the transgenic plant has increased sucrose levels, increased sucrose to glucose ratios, or both, compared to a control plant lacking the transgene. In a further aspect, a method of the instant application further comprises collecting a seed from the transgenic plant.

In another aspect, a method of producing a transgenic plant disclosed herein produces a transgenic plant having a transgene stably integrated into the nuclear genome of the transgenic plant. In a further aspect, a method of producing a transgenic plant disclosed herein produces a transgenic plant having a transgene stably integrated into the chloroplast of the transgenic plant.

In another aspect, a method of producing a transgenic plant disclosed herein uses a transgene comprising a promoter selected from the group consisting of a constitutive promoter, a tissue-specific promoter, and an inducible promoter. In one aspect, a constitutive promoter is the CaMV 35S promoter. In another aspect, a promoter is an abiotic stress inducible promoter.

In one aspect, the instant application discloses a method of producing a transgenic plant, the method comprising transforming a plant cell with a transgene encoding a target nucleic acid molecule that is complementary to a small RNA comprising a sequence having at least 80%, 85%, 88%, 90%, 92%, 95%, 96%, 97%, 98%, or 99% sequence identity to a sequence selected from the group consisting of SEQ ID NOs: 1 to 4, 9 to 255, 513 to 520, and 523-525, and producing a transgenic plant from the transformed cell, wherein the transgenic plant has increased sucrose levels, increased sucrose to glucose ratios, or both, compared to a non-transgenic control plant. In another aspect, a transgene used in a method of producing a transgenic plant disclosed herein expresses a small RNA, in a particular aspect a miRNA, target nucleic acid molecule that is substantially resistant to small RNA-, in a particular aspect a miRNA, mediated cleavage. In a further aspect, a small RNA target nucleic acid molecule used in a method disclosed herein is constitutively expressed.

In one aspect, a small RNA, in a particular aspect a miRNA, target nucleic acid molecule used in a method disclosed herein comprises a sequence having at least 80%, 85%, 88%, 90%, 92%, 95%, 96%, 97%, 98%, or 99% sequence identity to a sequence selected from the group consisting of SEQ ID NOs: 3 or 42-255.

In one aspect, a small RNA, in a particular aspect a miRNA, target nucleic acid molecule used in a method disclosed herein comprises a sequence at least 80%, 85%, 88%, 90%, 92%, 95%, 96%, 97%, 98%, or 99% sequence identity to a sequence selected from the group consisting of SEQ ID NOs: 1. 9-35, and 523-525.

In one aspect, a small RNA, in a particular aspect a miRNA, target nucleic acid molecule used in a method disclosed herein comprises a sequence at least 80%, 85%, 88%, 90%, 92%, 95%, 96%, 97%, 98%, or 99% sequence identity to a sequence selected from the group consisting of SEQ ID NOs: 2 and 36-41.

In another aspect, a small RNA, in a particular aspect a miRNA, target nucleic acid molecule used in a method disclosed herein encodes a polypeptide having at least 80%, 85%, 88%, 90%, 92%, 95%, 96%, 97%, 98%, or 99% sequence identity to a sequence selected from the group consisting of SEQ ID NOs: 503-512.

In one aspect, a small RNA, in a particular aspect a miRNA, target nucleic acid molecule used in a method disclosed herein is a target mimic. In one aspect, a target mimic is capable of binding the small RNA, in a particular aspect a miRNA, without being cleaved, and thus sequestering the small RNA, in a particular aspect a miRNA, and preventing the small RNA, in a particular aspect a miRNA, from binding other target molecules of the small RNA. In another aspect, a target mimic comprises extra nucleotides within a small RNA, in a particular aspect a miRNA, binding site between two nucleotides that are complementary to bases 10 and 11 of the small RNA, in a particular aspect a miRNA. In a further aspect, extra nucleotides contained in a target mimic consist of Adenine, Uracil, and Cytosine (AUC).

In one aspect, a target mimic of a small RNA, in a particular aspect a miRNA, or a small RNA, in a particular aspect a miRNA-resistant target nucleic acid molecule used herein is operably linked to a promoter naturally associated with a precursor of the small RNA, in a particular aspect a miRNA. In this way, without being bound to any scientific theory or mechanism, the target mimic or small RNA, in a particular aspect a miRNA-resistant target nucleic acid molecule will be expressed under the same circumstances as the small RNA, in a particular aspect a miRNA. In turn, the target mimic or small RNA, in a particular aspect a miRNA-resistant target nucleic acid molecule will compete with an endogenous target RNA for binding to the small RNA, in a particular aspect a miRNA, and thus prevent cleavage or downregulation of the endogenous target RNA.

In one aspect, the instant application discloses a method of producing a transgenic plant, the method comprising transforming a plant cell with a transgene that regulates the expression of a target nucleic acid molecule that is complementary to a small RNA, in a particular aspect a miRNA, comprising a sequence having at least 80%, 85%, 88%, 90%, 92%, 95%, 96%, 97%, 98%, or 99% sequence identity to a sequence selected from the group consisting of SEQ ID NOs:1 to 4, 9 to 255, 513 to 520, and 523-525, and producing a transgenic plant from the transformed cell, wherein the transgenic plant has improved drought tolerance compared to a non-transgenic control plant. In another aspect, a transgene used in a method disclosed herein regulates the expression of a small RNA, in a particular aspect a miRNA, target nucleic acid molecule via an artificial miRNA complementary with the small RNA target nucleic acid molecule. In a further aspect, a transgene used in a method disclosed herein regulates the expression of a small RNA, in a particular aspect a miRNA, target nucleic acid molecule via RNA interference.

In one aspect, an exogenous nucleic acid molecule used herein is, or encodes, a small RNA, in a particular aspect a miRNA, which controls or modulates sucrose levels in a fruit of a plant, controls or modulates glucose levels in a fruit of a plant, or controls or modulates sucrose to glucose ratios in a fruit of a plant. In a further aspect, an exogenous nucleic acid molecule used herein is or encodes a dsRNA molecule. In another aspect, an exogenous nucleic acid molecule used herein is or encodes an artificial miRNA. In a further aspect, an exogenous nucleic acid molecule used herein is or encodes an siRNA. In one aspect, an exogenous nucleic acid molecule used herein is or encodes a precursor of a small RNA. In another aspect, an exogenous nucleic acid molecule used herein is or encodes a precursor of a miRNA or siRNA. In one aspect, an exogenous nucleic acid molecule used herein is a naturally-occurring molecule. In another aspect, an exogenous nucleic acid molecule used herein is a synthetic molecule.

In one aspect, an exogenous nucleic acid molecule used herein is or encodes a stem-loop precursor of a small RNA, in a particular aspect a miRNA, comprising a sequence having at least 80%, 85%, 88%, 90%, 92%, 95%, 96%, 97%, 98%, or 99% sequence identity to a sequence selected from the group consisting of SEQ ID NOs: 3 and 42-255. A stem-loop precursor used herein comprises a sequence having at least 60%, 65%, 70%, 75%, 80%, 85%, 88%, 90%, 92%, 95%, 96%, 97%, 98%, or 99% sequence identity to a sequence selected from the group consisting of SEQ ID NOs: 5 to 8, and 256 to 502.

In one aspect, an exogenous nucleic acid molecule used herein is naked RNA or expressed from a nucleic acid expression construct, where it is operably linked to a regulatory sequence. In one aspect, a recombinant DNA construct or a transgene disclosed herein further comprises a transcription terminator.

In one aspect, *Agrobacterium*-mediated transformation is used in a method disclosed. In another aspect, a transgenic plant disclosed herein is produced by *agrobacterium*-mediated transformation.

In one aspect, a transgenic plant, or part thereof, disclosed herein is homozygous for the transgene. In another aspect, a transgenic plant, or part thereof, disclosed herein is heterozygous for the transgene.

In one aspect, a transgenic plant, or part thereof, disclosed herein has a single insertion of the transgene. In one aspect, a transgenic plant, or part thereof, disclosed herein has multiple insertions of the transgene at different genomic loci or at a single site in a tandem manner.

In one aspect, a transgenic plant disclosed herein comprises one or more additional enhanced traits. In one aspect, a transgenic plant disclosed herein comprises increased vigor over that of a control plant. In another aspect, a transgenic plant disclosed herein comprises higher yield than a control plant.

In one aspect, the transgenic expression of miR169 causes a reduction in the expression or activity of at least one target gene of miR169 in at least one cell type. In another aspect, the transgenic expression of miR169 causes a partial reduction in the expression or activity of at least one target gene of miR169 in at least one cell type. In a further aspect, the transgenic expression of miR169 causes a substantial reduction in the expression or activity of at least one target gene of miR169 in at least one cell type. In another aspect, the transgenic expression of miR169 causes an effective elimination of the expression or activity of at least one target gene of miR169 in at least one cell type.

In one aspect, the transgenic expression of miR169 causes a reduction in one or more cell types of the expression or activity of one gene encoding an amino acid sequence having at least 80%, 85%, 88%, 90%, 92%, 95%, 96%, 97%, 98%, or 99% sequence identity to a sequence selected from the group consisting of SEQ ID NOs: 503-512.

In one aspect, the transgenic expression of miR169 causes a substantial reduction in one or more cell types of the expression or activity of one gene encoding an amino acid sequence having at least 80%, 85%, 88%, 90%, 92%, 95%, 96%, 97%, 98%, or 99% sequence identity to a sequence selected from the group consisting of SEQ ID NOs: 503-512.

In one aspect, the transgenic expression of miR169 causes in one or more cell type an effective elimination of the expression or activity of one gene encoding an amino acid sequence having at least 80%, 85%, 88%, 90%, 92%, 95%, 96%, 97%, 98%, or 99% sequence identity to a sequence selected from the group consisting of SEQ ID NOs: 503-512.

In one aspect, the transgenic expression of a miR397 mimic, a miR528 mimic, or a miR1110 mimic causes an increase in the expression or activity of at least one target gene of miR397, miR528, or miR1110 in at least one cell type.

In another aspect, the transgenic expression of a miR397 mimic, a miR528 mimic, or a miR1110 mimic causes an increase of at least 20%, 40%, 60%, 80%, 100%, 200%, 300%, 400%, or 500% in the expression or activity of at least one gene encoding an amino acid sequence having at least 80%, 85%, 88%, 90%, 92%, 95%, 96%, 97%, 98%, or 99% sequence identity to a sequence selected from the group consisting of SEQ ID NOs: 503-512.

In a further aspect, an exogenous nucleic acid molecule used herein is a synthetic single-stranded nucleic acid molecule known as a miRNA inhibitor. A miRNA inhibitor is typically between about 17 to 25 nucleotides in length and comprises a 5' to 3' sequence that is at least 90% complementary to the 5' to 3' sequence of a mature miRNA. In certain embodiments, a miRNA inhibitor molecule is 17, 18, 19, 20, 21, 22, 23, 24, or 25 nucleotides in length, or any range derivable therein. Moreover, a miRNA inhibitor has a sequence (from 5' to 3') that is or is at least 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or 100% complementary, or any range derivable therein, to the 5' to 3' sequence of a mature miRNA, particularly a mature, naturally-occurring miRNA.

The instant application further discloses a transgenic plant or part thereof produced by a method disclosed herein. In an aspect, a transgenic plant or part thereof disclosed herein is a hybrid plant.

In one aspect, a transgenic plant, or part thereof, disclosed herein comprises a transgene comprising a sequence having at least 80%, 85%, 88%, 90%, 92%, 95%, 96%, 97%, 98%, or 99% sequence identity to a sequence selected from the group consisting of SEQ ID NOs: 1 to 4, 9 to 255, 513 to 520, and 523 to 525, wherein the transgenic plant has increased sucrose levels, increased sucrose to glucose ratios, or both, compared to a control plant lacking the transgene.

In another aspect, a transgenic plant, or part thereof, disclosed herein comprises a transgene encoding a polypeptide sequence having at least 80%, 85%, 88%, 90%, 92%, 95%, 96%, 97%, 98%, or 99% sequence identity to a sequence selected from the group consisting of SEQ ID NOs: 503 to 512, wherein the transgenic plant has increased sucrose levels, increased sucrose to glucose ratios, or both, compared to a control plant lacking the transgene.

In one aspect, a transgenic plant, or part thereof, disclosed herein comprises a transgene encoding a small RNA comprising a sequence having at least 80%, 85%, 88%, 90%, 92%, 95%, 96%, 97%, 98%, or 99% sequence identity to a sequence selected from the group consisting of SEQ ID NOs: 1 to 4, 9 to 255, 513 to 520, and 523 to 525, wherein the transgenic plant has increased sucrose levels, increased sucrose to glucose ratios, or both, compared to a control plant lacking the transgene.

In another aspect, a transgenic plant, or part thereof, disclosed herein comprises a transgene stably integrated into the nuclear genome of the transgenic plant. In a further aspect, a method of producing a transgenic plant disclosed herein produces a transgenic plant having a transgene stably integrated into the chloroplast of the transgenic plant.

In another aspect, a transgenic plant, or part thereof, disclosed herein comprises a transgene comprising a promoter selected from the group consisting of a constitutive promoter, a tissue-specific promoter, and an inducible promoter. In one aspect, a constitutive promoter is the CaMV 35S promoter. In another aspect, a promoter is an abiotic stress-inducible promoter.

In one aspect, a transgenic plant, or part thereof, disclosed herein comprises a transgene encoding a small RNA, in a particular aspect a miRNA, target nucleic acid molecule that is complementary to a small RNA comprising a sequence having at least 80%, 85%, 88%, 90%, 92%, 95%, 96%, 97%, 98%, or 99% sequence identity to a sequence selected from the group consisting of SEQ ID NOs: 1 to 4, 9 to 255, 513 to 520, and 523 to 525, wherein the transgenic plant has increased sucrose levels, increased sucrose to glucose ratios, or both, compared to a non-transgenic control plant.

In another aspect, a transgenic plant, or part thereof, disclosed herein comprises a small RNA, in a particular aspect a miRNA, target nucleic acid molecule that is substantially resistant to small RNA-mediated cleavage. In a further aspect, a small RNA, in a particular aspect a miRNA, target nucleic acid molecule used in a method disclosed herein is constitutively expressed. In one aspect, a small RNA, in a particular aspect a miRNA, target nucleic acid molecule produced from a transgene of a transgenic plant, or part thereof, disclosed herein comprises a sequence having at least 80%, 85%, 88%, 90%, 92%, 95%, 96%, 97%, 98%, or 99% sequence identity to a sequence selected from the group consisting of SEQ ID NOs: 513 to 520.

In another aspect, a small RNA, in a particular aspect a miRNA, target nucleic acid molecule produced by a transgene in a transgenic plant, or part thereof, disclosed herein encodes a polypeptide having at least 80%, 85%, 88%, 90%, 92%, 95%, 96%, 97%, 98%, or 99% sequence identity to a sequence selected from the group consisting of SEQ ID NOs: 503-512.

In one aspect, a transgenic plant, or part thereof, disclosed herein comprises a transgene encoding a small RNA, in a particular aspect a miRNA, target mimic. In one aspect, a small RNA, in a particular aspect a miRNA, target mimic is expressed in a transgenic plant, or part thereof, disclosed herein, and is capable of binding a small RNA, in a particular aspect a miRNA, without being cleaved, and thus sequestering the small RNA, in a particular aspect a miRNA, and preventing the small RNA from binding other target molecules of the small RNA, in a particular aspect a miRNA. In another aspect, a target mimic comprises extra nucleotides within a small RNA, in a particular aspect a miRNA, binding site between two nucleotides that are complementary to bases 10 and 11 of the small RNA, in a particular aspect a miRNA. In a further aspect, extra nucleotides contained in a target mimic consist of Adenine, Uracil, and Cytosine (AUC).

In one aspect, the instant application discloses a transgenic plant, or part thereof, comprising a transgene that regulates the expression of a small RNA, in a particular aspect a miRNA, target nucleic acid molecule that is complementary to a small RNA, in a particular aspect a miRNA, comprising a sequence having at least 80%, 85%, 88%, 90%, 92%, 95%, 96%, 97%, 98%, or 99% sequence identity to a sequence selected from the group consisting of SEQ ID NOs: 1 to 4, 9 to 255, 513 to 520, and 523-525, wherein the transgenic plant has increased sucrose levels, increased sucrose to glucose ratios, or both, compared to a non-transgenic control plant. In another aspect, a transgenic plant, or part thereof, disclosed herein comprises a transgene encoding an artificial miRNA complementary with a small RNA target nucleic acid molecule. In a further aspect, a transgenic plant, or part thereof, disclosed herein comprises a transgene that regulates the expression of a small RNA target nucleic acid molecule via RNA interference.

In one aspect, a transgenic plant, or part thereof, disclosed herein further comprises a transgene encoding a protein that provides tolerance to an herbicide. A transgene providing herbicide resistance and a transgene provide an enhanced trait disclosed herein can be part of a single transgene which has a single site in the genome, or belong to separate transgenes that are located at different sites in the genome.

In another aspect, a transgenic plant, or part thereof, disclosed herein is resistant to an herbicide selected from the group consisting of glyphosate, 2,4-dichloropropionic acid, bromoxynil, sulfonylurea, imidazolinone, triazolopyrimidine, pyrimidyloxybenzoates, phthalide, bialaphos, phosphinothricin, glufosinate, atrazine, dicamba, cyclohexanedione (sethoxydim), and aryloxyphenoxypropionate (haloxyfop).

In a further aspect, a transgenic plant part disclosed herein is selected from the group consisting of a leaf, a stem, a root, a seed, a flower, pollen, an anther, an ovule, a pedicel, a fruit, a meristem, a cotyledon, a hypocotyl, a pod, an embryo, endosperm, an explant, a callus, a tissue culture, a shoot, a cell, and a protoplast.

In one aspect, the instant disclosure provides a non-reproductive plant cell or part, for example a leaf, a stem, a root, a pedicel, a cotyledon, or a hypocotyl. In another aspect, the instant disclosure provides a plant part or cell that cannot regenerate into a complete plant. In another aspect, the instant disclosure provides a plant part or cell that cannot regenerate into a new plant as a means to reproduce or propagate a plant.

In one aspect, the instant disclosure provides a population of transgenic plants provided herein which have improved drought tolerance compared to a non-transgenic control plant. In another aspect, the instant disclosure also provides a container of transgenic seeds provided herein which have improved drought tolerance compared to a non-transgenic control seed.

In one aspect, the instant disclosure provides a population of transgenic plants provided herein which have increased sucrose levels in a fruit of a plant, increased sucrose to glucose ratios in a fruit of a plant, or both compared to a non-transgenic control plant. In another aspect, the instant disclosure also provides a container of transgenic seeds provided herein which have increased sucrose levels in a fruit of a plant, increased sucrose to glucose ratios in a fruit of a plant, or both compared to a non-transgenic control seed.

A container of transgenic seeds of the instant disclosure may contain any number, weight, or volume of seeds. For example, a container can contain at least, or greater than, 100, 200, 300, 400, 500, 600, 700, 800, 900, 1000, 1500, 2000, 2500, 3000, 3500, 4000 or more seeds. Alternatively, the container can contain at least, or greater than, 1 ounce, 5 ounces, 10 ounces, 1 pound, 2 pounds, 3 pounds, 4 pounds, 5 pounds or more seeds. Containers of seeds may be any container available in the art. By way of non-limiting example, a container may be a box, a bag, a packet, a pouch, a tape roll, or a tube.

In one aspect, the instant disclosure provides a population of transgenic tomato plants provided herein which have increased sucrose levels in a fruit of a plant, increased sucrose to glucose ratios in a fruit of a plant, or both compared to a non-transgenic control tomato plant. In another aspect, the instant disclosure also provides a container of transgenic tomato seeds provided herein which have increased sucrose levels in a fruit of a plant, increased sucrose to glucose ratios in a fruit of a plant, or both compared to a non-transgenic control tomato seed.

A container of transgenic tomato seeds of the instant disclosure may contain any number, weight or volume of seeds. For example, a container can contain at least, or greater than, 100, 200, 300, 400, 500, 600, 700, 800, 900, 1000, 1500, 2000, 2500, 3000, 3500, 4000 or more seeds. Alternatively, the container can contain at least, or greater than, 1 ounce, 5 ounces, 10 ounces, 1 pound, 2 pounds, 3 pounds, 4 pounds, 5 pounds or more seeds. Containers of tomato seeds may be any container available in the art. By way of non-limiting example, a container may be a box, a bag, a packet, a pouch, a tape roll, or a tube.

In one aspect, the instant disclosure also provides a food or feed comprising the plants or a portion thereof of the present disclosure. In a further aspect, a transgenic plants, or part thereof disclosed herein is comprised in a food or feed product (e.g., dry, liquid, paste). A food or feed product is any ingestible preparation containing the transgenic plants, or parts thereof, of the present disclosure, or preparations made from these plants. Thus, the plants or preparations are suitable for human (or animal) consumption, e.g., the transgenic plants or parts thereof are more readily digested. Feed products of the present disclosure further include an oil or a beverage adapted for animal consumption.

In another aspect, a transgenic plant disclosed herein can be used directly as feed products, or alternatively can be incorporated or mixed with feed products for consumption. Furthermore, the food or feed products can be processed or used as is. Exemplary feed products comprising the transgenic plants, or parts thereof, include, but are not limited to, grains, cereals, such as oats, e.g., black oats, barley, wheat, or rye; sorghum; corn; vegetables; leguminous plants, especially soybeans, root vegetables, and cabbage; or green forage, such as grass or hay.

Also contemplated in the present disclosure are hybrids produced from a transgenic plant disclosed herein.

Promoters may be constitutive or regulatable. The term "constitutive" when made in reference to a promoter means that the promoter is capable of directing transcription of an operably linked nucleic acid sequence in the absence of a stimulus (e.g., heat shock, chemicals, light, etc.). Typically, constitutive promoters are capable of directing expression of a transgene in substantially any cell and any tissue. In contrast, a "regulatable" promoter is one which is capable of directing a level of transcription of an operably linked nucleic acid sequence in the presence of a stimulus (e.g., heat shock, chemicals, light, etc.) which is different from the level of transcription of the operably linked nucleic acid sequence in the absence of the stimulus. In an aspect, a transgenic plant of the present disclosure can include DNA constructs having constitutive or regulatable promoters that provide transient or constitutive expression of one or more siRNAs or siRNA precursors. In certain aspects, transgenic plants can include DNA constructs having both a constitutive promoter and a regulatable promoter.

Any promoter that functions in a plant cell to cause the production of a RNA molecule, such as those promoters described herein, without limitation, can be used. In a preferred embodiment, the promoter is a plant promoter.

Tissue-specific or cell-type-specific expression of a nucleic acid molecule disclosed herein can be achieved by tissue-specific or cell-type-specific promoters. The term "tissue specific" as it applies to a promoter refers to a promoter that is capable of directing selective expression of a nucleotide sequence of interest to a specific type of tissue (e.g., petals) in the relative absence of expression of the same nucleotide sequence of interest in a different type of tissue (e.g., roots). The term "cell type specific" as applied to a promoter refers to a promoter which is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue.

Root-specific promoters may also be used. An example of such a promoter is the promoter for the acid chitinase gene (Samac et al., *Plant Mol. Biol.*, 25:587-596 (1994)). Expression in root tissue could also be accomplished by utilizing the root specific subdomains of the CaMV35S promoter that have been identified (Lam et al., *PNAS USA* 86:7890-7894 (1989)). Other root-cell-specific promoters include those reported by Conkling et al. (*Plant Physiol.*, 93:1203-1211 (1990)).

In an aspect according to the instant specification, tissue-specific or cell-type-specific expression of a nucleic acid molecule disclosed herein can be achieved by tissue-specific or cell-type-specific enhancer sequences. The term "tissue specific" as it applies to an enhancer refers to an enhancer that is capable of directing selective expression of a nucleotide sequence of interest to a specific type of tissue (e.g., petals) in the relative absence of expression of the same nucleotide sequence of interest in a different type of tissue (e.g., roots). The term "cell type specific" as applied to an enhancer refers to an enhancer which is capable of directing selective expression of a nucleotide sequence of interest in a specific type of cell in the relative absence of expression of the same nucleotide sequence of interest in a different type of cell within the same tissue. The term "cell type specific" when applied to an enhancer also means an enhancer capable of promoting selective expression of a nucleotide sequence of interest in a region within a single tissue.

In a further aspect, a nucleic acid molecule disclosed herein can be applied to the surface of a plant (e.g., leaf surface), or treated to a plant seed to induce a physiological response in a plant, including without limitation, providing improved tolerance to abiotic stresses (e.g., drought or salinity). Methods and composition components for applying a nucleic acid molecule to the surface of a plant was disclosed in US 2011/0296556 A1, which publication is incorporated by reference in its entirety.

Any commercially or scientifically valuable plant is envisaged in accordance with these embodiments of the disclosure. Plants that are particularly useful in the methods of the disclosure include all plants which belong to the super family Viridiplantae, in particular monocotyledonous and dicotyledonous plants including a fodder or forage legume, ornamental plant, food crop, tree, or shrub selected from the list comprising *Acacia* spp., *Acer* spp., *Actinidia* spp., *Aesculus* spp., *Agathis australis, Albizia amara, Alsophila tricolor, Andropogon* spp., *Arachis* spp., *Areca catechu, Astelia fragrans, Astragalus cicer, Baikiaea plurijuga, Betula* spp., *Brassica* spp., *Bruguiera gymnorrhiza, Burkea africana, Butea frondosa, Cadaba farinosa, Calliandra* spp, *Camellia sinensis, Canna indica, Capsicum* spp., *Cassia* spp., *Centroema pubescens, Chacoomeles* spp., *Cinnamomum cassia, Coffea arabica, Colophospermum mopane, Coronillia varia, Cotoneaster serotina, Crataegus* spp., *Cucumis* spp., *Cupressus* spp., *Cyathea dealbata, Cydonia oblonga, Cryptomeria japonica, Cymbopogon* spp., *Cynthea dealbata, Cydonia oblonga, Dalbergia monetaria, Davallia divaricata, Desmodium* spp., *Dicksonia squarosa, Dibeteropogon amplectens, Dioclea* spp, *Dolichos* spp., *Dorycnium rectum, Echinochloa pyramidalis, Ehraffia* spp., *Eleusine coracana, Eragrestis* spp., *Erythrina* spp., *Eucalyptus* spp., *Euclea schimperi, Eulalia vi/losa, Pagopyrum* spp., *Feijoa sellowlana, Fragaria* spp., *Flemingia* spp, *Freycinetia banksli, Geranium thunbergii, Ginkgo biloba, Glycine javanica, Gliricidia* spp, *Gossypium hirsutum, Grevillea* spp., *Guibourtia coleosperma, Hedysarum* spp., *Hemaffhia altissima, Heteropogon contoffus, Hordeum vulgare, Hyparrhenia rufa, Hypericum erectum, Hypeffhelia dissolute, Indigo incamata, Iris* spp., *Leptarrhena pyrolifolia, Lespediza* spp., *Lettuca* spp., *Leucaena leucocephala, Loudetia simplex, Lotonus bainesli, Lotus* spp., *Macro tyloma axillare, Malus* spp., *Manihot esculenta, Medicago saliva, Metasequoia glyptostroboides, Musa sapientum, Nicotianum* spp., *Ono-

*brychis* spp., *Ornithopus* spp., *Oryza* spp., *Peltophorum africanum, Pennisetum* spp., *Persea gratissima, Petunia* spp., *Phaseolus* spp., *Phoenix canadensis, Phormium cookianum, Photinia* spp., *Picea glauca, Pinus* spp., *Pisum sativam, Podocarpus totara, Pogonarthria fleckii, Pogonaffhria squarrosa, Populus* spp., *Prosopis cineraria, Pseudotsuga menziesii, Pterolobium stellatum, Pyrus communis, Quercus* spp., *Rhaphiolepis umbellata, Rhopalostylis sapida, Rhus natalensis, Ribes grossularia, Ribes* spp., *Robinia pseudoacacia, Rosa* spp., *Rubus* spp., *Salix* spp., *Schyzachyrium sanguineum, Sciadopitys vefficillata, Sequoia sempervirens, Sequoiadendron giganteum, Sorghum bicolor, Spinacia* spp., *Sporobolus fimbriatus, Stiburus alopecuroides, Stylosanthos humilis, Tadehagi* spp., *Taxodium distichum, Themeda triandra, Trifolium* spp., *Triticum* spp., *Tsuga heterophylla, Vaccinium* spp., *Vicia* spp., *Vitis vinifera, Watsonia pyramidata, Zantedeschia aethiopica, Zea mays*, amaranth, artichoke, asparagus, broccoli, Brussels sprouts, cabbage, canola, carrot, cauliflower, celery, collard greens, flax, kale, lentil, oilseed rape, okra, onion, potato, rice, soybean, straw, sugar beet, sugar cane, sunflower, tomato, squash tea, maize, wheat, barley, rye, oat, peanut, pea, lentil and alfalfa, cotton, rapeseed, canola, pepper, sunflower, tobacco, eggplant, *eucalyptus*, a tree, an ornamental plant, a perennial grass and a forage crop. Alternatively, algae and other non-Viridiplantae can be used for the methods of the present disclosure.

In aspects according to the present disclosure, a transgenic plant may be any plant. In certain aspects, a transgenic plant may preferably be a tomato plant.

Genetic material provided in the present disclosure may be introduced into any species, for example, without limitation, monocotyledons or dicotyledons, including, but not limited to alfalfa, apple, *Arabidopsis*, banana, barley, *Brassica campestris*, canola, castor bean, *chrysanthemum*, coffee, cotton, cottonseed, corn, *crambe*, cranberry, cucumber, dendrobium, *dioscorea, eucalyptus*, fescue, flax, *gladiolus*, liliacea, linseed, millet, muskmelon, mustard, oat, oil palm, oilseed rape, *papaya*, peanut, perennial, *Phaseolus*, potato, rapeseed, rice, rye, ryegrass, safflower, sesame, sorghum, soybean, sugarbeet, sugarcane, sunflower, tobacco, tomato, turfgrass, or wheat (Christou, I N O: *Particle Bombardment for Genetic Engineering of Plants*, Biotechnology Intelligence Unit. Academic Press, San Diego, Calif. (1996)), with alfalfa, *Arabidopsis, Brassica campestris*, canola, castor bean, corn, cotton, cottonseed, *crambe*, flax, linseed, mustard, oil palm, oilseed rape, peanut, potato, rapeseed, sunflower, sesame, soybean, sunflower, tobacco, tomato, and wheat preferred, and *Brassica campestris*, canola, corn, oil palm, oilseed rape, peanut, rapeseed, safflower, soybean, and sunflower more preferred. In a more preferred aspect, genetic material is transferred into a fruit species. In another more preferred aspect, genetic material is transferred into vegetable species. In another particularly preferred embodiment, genetic material is transferred into a tomato plant.

A transgenic tomato plant of the instant disclosure can be from any maturity group or any variety. Transgenic plants of the present disclosure may be prepared from elite tomato lines or plants, wild type tomato lines or plants, and heirloom variety tomato lines or plants. As used herein, the term "elite tomato," "elite tomato plant" or "elite tomato variety or cultivar" refers to a tomato variety that has been cultivated and bred for performance and to have commercially desirable characteristics (e.g., suitable for mass production and marketing, a "supermarket tomato"). Elite tomatoes are used by breeders to create commercial tomato varieties. Commercial tomatoes are usually hybrids, produced by controlled pollination with elite tomatoes, which may involve artificial techniques (e.g., by hand, by machine, etc.) to control the pollination. Thus, "elite tomato variety" or "elite hybrid tomato parent" may refer to the parent of a hybrid commercial tomato or a tomato that is being bred to become a commercial tomato line. Elite tomatoes have been bred for characteristics such as fruit shape, color, hardiness, uniformity of size, disease resistance, uniformity of fruit set, and the like. Elite tomatoes may be determinate or indeterminate. A "commercial tomato" is a descendent of an "elite tomato" that has been commercialized (e.g., sold in commerce), though as used herein "commercial tomato" may also refer to a tomato variety that is being bred for commercial traits even if it has not yet been sold in commerce. As used herein the term "elite tomato" includes lines used in breeding commercial tomatoes as well as lines used in breeding tomatoes that are not yet commercialized. The intent is not to limit the disclosure to only to commercial varieties descended from elite tomatoes. For purposes of the present disclosure, "elite tomatoes" do not include "heirloom tomatoes" and vice versa.

Plants of the present disclosure can be part of or generated from a breeding program, or subject to further breeding. The choice of breeding method depends on the mode of plant reproduction, the heritability of the trait(s) being improved, and the type of cultivar used commercially (e.g., $F_1$ hybrid cultivar, pureline cultivar, etc). Selected, non-limiting approaches, for breeding the plants of the present disclosure are set forth below. A breeding program can be enhanced using marker-assisted selection of the progeny of any cross. It is further understood that any commercial and non-commercial cultivars can be utilized in a breeding program. Factors such as, for example, emergence vigor, vegetative vigor, stress tolerance, disease resistance, branching, flowering, seed set, seed size, seed density, standability, and threshability will generally dictate the choice.

For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection. In a preferred embodiment, a backcross or recurrent breeding program is undertaken.

The complexity of inheritance influences choice of the breeding method. Backcross breeding can be used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Breeding lines can be tested and compared to appropriate standards in environments representative of the commercial target area(s) for two or more generations. The best lines are candidates for new commercial cultivars; those still deficient in traits may be used as parents to produce new populations for further selection.

One method of identifying a superior plant is to observe its performance relative to other experimental plants and to a widely grown standard cultivar. If a single observation is inconclusive, replicated observations can provide a better estimate of its genetic worth. A breeder can select and cross two or more parental lines, followed by repeated selfing and selection, producing many new genetic combinations.

The development of new cultivars requires the development and selection of varieties, the crossing of these varieties and the selection of superior hybrid crosses. The hybrid seed can be produced by manual crosses between selected male-fertile parents or by using male sterility systems. Hybrids are selected for certain single gene traits such as pod color, flower color, seed yield, pubescence color, or herbicide resistance, which indicate that the seed is truly a hybrid. Additional data on parental lines, as well as the phenotype of the hybrid, influence the breeder's decision whether to continue with the specific hybrid cross.

Pedigree breeding and recurrent selection breeding methods can be used to develop cultivars from breeding populations. Breeding programs combine desirable traits from two or more cultivars or various broad-based sources into breeding pools from which cultivars are developed by selfing and selection of desired phenotypes. New cultivars can be evaluated to determine which have commercial potential.

Pedigree breeding is used commonly for the improvement of self-pollinating crops. Two parents who possess favorable, complementary traits are crossed to produce an $F_1$. A $F_2$ population is produced by selfing one or several $F_1$'s. Selection of the best individuals from the best families is carried out. Replicated testing of families can begin in the $F_4$ generation to improve the effectiveness of selection for traits with low heritability. At an advanced stage of inbreeding (e.g., $F_6$ and $F_7$), the best lines or mixtures of phenotypically similar lines are tested for potential release as new cultivars.

Backcross breeding has been used to transfer genes for a simply inherited, highly heritable trait into a desirable homozygous cultivar or inbred line, which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting parent is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, breeders commonly harvest one or more pods from each plant in a population and thresh them together to form a bulk. Part of the bulk is used to plant the next generation and part is put in reserve. The procedure has been referred to as modified single-seed descent or the pod-bulk technique.

The multiple-seed procedure has been used to save labor at harvest. It is faster to thresh pods with a machine than to remove one seed from each by hand for the single-seed procedure. The multiple-seed procedure also makes it possible to plant the same number of seed of a population each generation of inbreeding.

A transgenic plant of the present disclosure may also be reproduced using apomixis. Apomixis is a genetically-controlled method of reproduction in plants where the embryo is formed without union of an egg and a sperm. There are three basic types of apomictic reproduction: 1) apospory where the embryo develops from a chromosomally unreduced egg in an embryo sac derived from the nucleus, 2) diplospory where the embryo develops from an unreduced egg in an embryo sac derived from the megaspore mother cell, and 3) adventitious embryony where the embryo develops directly from a somatic cell. In most forms of apomixis, pseudogamy or fertilization of the polar nuclei to produce endosperm is necessary for seed viability. In apospory, a nurse cultivar can be used as a pollen source for endosperm formation in seeds. The nurse cultivar does not affect the genetics of the aposporous apomictic cultivar since the unreduced egg of the cultivar develops parthenogenetically, but makes possible endosperm production. Apomixis is economically important, especially in transgenic plants, because it causes any genotype, no matter how heterozygous, to breed true. Thus, with apomictic reproduction, heterozygous transgenic plants can maintain their genetic fidelity throughout repeated life cycles. Methods for the production of apomictic plants are known in the art. See, e.g., U.S. Pat. No. 5,811,636.

Transgenic plants comprising or derived from plant cells of this disclosure transformed with recombinant DNA can be further enhanced with stacked traits, e.g., a crop plant having an enhanced trait resulting from expression of DNA disclosed herein in combination with herbicide and/or pest resistance traits. For example, genes of the current disclosure can be stacked with other traits of agronomic interest, such as a trait providing herbicide resistance, or insect resistance, such as using a gene from *Bacillus thuringensis* to provide resistance against lepidopteran, coliopteran, homopteran, hemiopteran, and other insects. Herbicides for which transgenic plant tolerance has been demonstrated and the method of the present disclosure can be applied include, but are not limited to, glyphosate, dicamba, glufosinate, sulfonylurea, bromoxynil, and norflurazon herbicides.

This disclosure also envisages expressing a plurality of exogenous polynucleotides in a single plant to thereby achieve superior effect on multiple traits, for example, nitrogen use efficiency, biotic or abiotic stress tolerance, yield, vigor, and biomass. Expressing a plurality of exogenous polynucleotides in a single plant can be effected by co-introducing multiple nucleic acid constructs, each including a different exogenous polynucleotide, into a single plant cell. The transformed cell can then be regenerated into a mature plant using the methods described hereinabove. Alternatively, expressing a plurality of exogenous polynucleotides in a single host plant can be effected by co-introducing into a single plant-cell a single nucleic-acid construct including a plurality of different exogenous polynucleotides. Such a construct can be designed with a single promoter sequence which can transcribe a polycistronic messenger RNA including all the different exogenous polynucleotide sequences. Alternatively, the construct can include several promoter sequences each linked to a different exogenous polynucleotide sequence.

Alternatively, expressing a plurality of exogenous polynucleotides can be effected by introducing different nucleic acid constructs, including different exogenous polynucleotides, into a plurality of plants. The regenerated transformed plants can then be cross-bred and the resultant progeny selected for superior yield or fiber traits as described above, using conventional plant breeding techniques.

In one aspect, a plant expressing the exogenous polynucleotide(s) disclosed herein may be grown under stress (nitrogen or abiotic) or normal conditions (e.g., biotic conditions and/or conditions with sufficient water, and nutrients such as nitrogen and fertilizer). Such conditions, which depend on the plant being grown, are known to those skilled in the art of agriculture, and are further described above. The instant disclosure also contemplates a method of growing a plant expressing the exogenous polynucleotide(s) disclosed herein under abiotic stress or nitrogen-limiting conditions. Non-limiting examples of abiotic stress conditions include water deprivation, drought, excess of water (e.g., flood, waterlogging), freezing, low temperature, high temperature, strong winds, heavy metal toxicity, anaerobiosis, nutrient deficiency, nutrient excess, salinity, atmospheric pollution, intense light, insufficient light, UV irradiation, etiolation, and atmospheric pollution.

Methods of determining the level in a plant of an exogenous polynucleotide disclosed herein are well known in the art and include, for example, Northern blot analysis, reverse transcription polymerase chain reaction (RT-PCR) analysis (including quantitative, semi-quantitative, or real-time RT-PCR), and RNA-in situ hybridization.

Plants exogenously expressing the polynucleotide of the disclosure can be screened to identify those that show the greatest increase of a desired plant trait. In one aspect, the present disclosure also provides a method of evaluating a trait of a plant, the method comprising: (a) expressing in a plant or a portion thereof the nucleic acid construct and (b) evaluating a trait of a plant as compared to a wild type plant of the same type, thereby evaluating the trait of the plant.

The effect of a transgene or an exogenous polynucleotide on different plant characteristics may be determined by any method known to one of ordinary skill in the art.

The biomass, vigor and yield of the plant can also be evaluated using any method known to one of ordinary skill in the art. Thus, for example, plant vigor can be calculated by the increase in growth parameters such as leaf area, fiber length, rosette diameter, plant fresh weight and the like per time.

As mentioned, the increase of plant yield can be determined by various parameters. For example, increased yield of rice may be manifested by an increase in one or more of the following: number of plants per growing area, number of panicles per plant, number of spikelets per panicle, number of flowers per panicle, seed filling rate, thousand kernel weight (1000-weight), oil content per seed, and starch content per seed, among others. An increase in yield may also result in modified architecture, or may occur because of modified architecture. Similarly, increased yield of soybean may be manifested by an increase in one or more of the following: number of plants per growing area, number of pods per plant, number of seeds per pod, seed filling rate, thousand seed weight (1000-weight), oil content per seed, and protein content per seed, among others. Alternatively, an increase in yield of soybean may also be manifested by a reduction of pod shattering. An increase in yield may also result in modified architecture, or may occur because of modified architecture.

In an aspect, a transgenic plant of the present disclosure can show enhanced performance based on one or more of the assays set forth herein, including without limitation, in the Examples. In an aspect, a transgenic plant of the present disclosure can be a homozygous plant showing enhanced performance based on one or more of the assays set forth herein, including without limitation, in the Examples. In an aspect, a transgenic plant of the present disclosure can be hybrid plant showing enhanced performance based on one or more of the assays set forth herein, including without limitation, in the Examples. In an aspect, a transgenic plant of the present disclosure can be a heterozygous plant showing enhanced performance based on one or more of the assays set forth herein, including without limitation, in the Examples.

In an aspect, a transgenic plant of the present disclosure can exhibit transiently or constitutively one or more traits or phenotypes selected from an enhanced trait, including without limitation, increased sucrose levels in a fruit of a plant, increased sucrose to glucose ratios in a fruit of a plant, or both.

In an aspect, a transgenic plant of the present disclosure can be a homozygous plant that exhibits transiently or constitutively one or more traits or phenotypes selected from an enhanced trait, including without limitation, increased sucrose levels in a fruit of a plant, increased sucrose to glucose ratios in a fruit of a plant, or both.

In an aspect a transgenic plant of the present disclosure can be a hybrid plant that exhibits transiently or constitutively one or more traits or phenotypes selected from an enhanced trait, including without limitation, increased sucrose levels in a fruit of a plant, increased sucrose to glucose ratios in a fruit of a plant, or both.

In an aspect, a transgenic plant of the present disclosure can be a heterozygous plant that exhibits transiently or constitutively one or more traits or phenotypes selected from an enhanced trait, including without limitation, increased sucrose levels in a fruit of a plant, increased sucrose to glucose ratios in a fruit of a plant, or both.

The following Examples are presented for the purposes of illustration and should not be construed as limitations.

EXAMPLES

Example 1

Differential Expression of miRNAs in Two Tomato Plant Varieties M82 and PIMP

Plant Material

Tomato seeds are germinated and plants are grown at 28° C. under 16 hours light: 8 hours dark regime. The M82 variety is used as the cultivated tomato, and has innate high sugar content, and PIMP is used as the wild tomato.

Total RNA Extraction

Total RNA of leaf samples from four biological repeats are extracted using the mirVana™ kit (Ambion, Austin, Tex.) by pooling 3-4 plants to one biological repeat.

Microarray Design

Custom microarrays are manufactured by Agilent Technologies by in situ synthesis of DNA oligonucleotide probes for 890 plant and algal microRNAs, with each probe being printed in triplicate.

Results

The following table presents sequences that are found to be differentially expressed between the M82 and PIMP varieties. Up regulated means the sequence is induced in the sugar-enriched M82 variety and down regulated means the sequence is repressed in the M82 variety.

TABLE 1

Differentially Expressed Small RNAs in Cultivated Tomato Plants of M82 Variety.

| Mir Name | Mature Sequence/ SEQ ID NO: | Stem Loop/ SEQ ID NO: | Direction | Fold Change | P value |
|---|---|---|---|---|---|
| Bna-miR397a | 1 | 5 | Down | 10.36 | 7.2e−005 |
| Osa-miR528 | 2 | 6 | Down | 1.79 | 4.60E-02 |
| Sly-miR169d | 3 | 7 | Up | 2.11 | 2.8e−002 |
| Smo-miR1110 | 4 | 8 | Down | 1.83 | 1.40E-02 |

Example 2

Identification of Homologous and Orthologous Sequences of Differential Small RNAs Associated with Enhanced Sugar Content in Tomato Plants The small RNA sequences of the invention that are either down- or up-regulated in the cultivated tomato variety M82 are examined for homologous and orthologous sequences using the miRBase database (available on the internet at www.mirbase.org/) and the Plant MicroRNA Database (PMRD, available on the internet at bioinformatics.cau.edu.cn/PMRD). The mature miRNA sequences that are homologous or orthologous to the miRNAs of the invention (listed in Table 1) are found using miRNA public databases, having at least 80% identity of the entire small RNA length, and are summarized in Table 2 below.

TABLE 2

Summary of Homologs/Orthologs of Small RNA Probes of Table 1.

| Small RNA Name | Mature sequence/ SEQ ID No: | Mir Length | Stem-loop sequence/ SEQ ID No: | Homolog Name | Homolog sequence/ SEQ ID No: | Homolog length | % Identity | Homolog Stem-loop Sequence/ SEQ ID No: |
|---|---|---|---|---|---|---|---|---|
| bna-miR397a | 1 | 22 | 5 | aly-miR397a | 9 | 21 | 0.95 | 256 |
| bna-miR397a | 1 | 22 | 5 | aly-miR397b | 10 | 21 | 0.95 | 257 |
| bna-miR397a | 1 | 22 | 5 | ath-miR397a | 11 | 21 | 0.95 | 258 |
| bna-miR397a | 1 | 22 | 5 | ath-miR397b | 12 | 21 | 0.91 | 259 |
| bna-miR397a | 1 | 22 | 5 | bdi-miR397 | 13 | 21 | 0.95 | 260 |
| bna-miR397a | 1 | 22 | 5 | bdi-miR397a | 14 | 21 | 0.95 | 261 |
| bna-miR397a | 1 | 22 | 5 | bdi-miR397b | 15 | 21 | 0.86 | 262 |
| bna-miR397a | 1 | 22 | 5 | bna-miR397b | 16 | 22 | 1 | 263 |
| bna-miR397a | 1 | 22 | 5 | csi-miR397 | 17 | 21 | 0.95 | 264 |
| bna-miR397a | 1 | 22 | 5 | ghr-miR397a | 18 | 22 | 0.86 | 265 |
| bna-miR397a | 1 | 22 | 5 | hvu-miR397 | 19 | 21 | 0.86 | 266 |
| bna-miR397a | 1 | 22 | 5 | osa-miR397a | 20 | 21 | 0.95 | 267 |
| bna-miR397a | 1 | 22 | 5 | osa-miR397a.2 | 21 | 21 | 0.82 | 268 |
| bna-miR397a | 1 | 22 | 5 | osa-miR397b | 22 | 21 | 0.91 | 269 |
| bna-miR397a | 1 | 22 | 5 | osa-miR397b.2 | 23 | 21 | 0.82 | 270 |
| bna-miR397a | 1 | 22 | 5 | pab-miR397 | 24 | 21 | 0.91 | 271 |
| bna-miR397a | 1 | 22 | 5 | ptc-miR397a | 25 | 21 | 0.95 | 272 |
| bna-miR397a | 1 | 22 | 5 | ptc-miR397b | 26 | 21 | 0.91 | 273 |
| bna-miR397a | 1 | 22 | 5 | ptc-miR397c | 27 | 21 | 0.86 | 274 |
| bna-miR397a | 1 | 22 | 5 | rco-miR397 | 28 | 21 | 0.95 | 275 |
| bna-miR397a | 1 | 22 | 5 | sbi-miR397 | 29 | 21 | 0.95 | 276 |
| bna-miR397a | 1 | 22 | 5 | sly-miR397 | 30 | 20 | 0.86 | 277 |
| bna-miR397a | 1 | 22 | 5 | tcc-miR397 | 31 | 21 | 0.95 | 278 |
| bna-miR397a | 1 | 22 | 5 | vvi-miR397a | 32 | 21 | 0.95 | 279 |
| bna-miR397a | 1 | 22 | 5 | vvi-miR397b | 33 | 21 | 0.95 | 280 |
| bna-miR397a | 1 | 22 | 5 | zma-miR397a | 34 | 21 | 0.91 | 281, 526 |
| bna-miR397a | 1 | 22 | 5 | zma-miR397b | 35 | 21 | 0.91 | 282, 527 |
| osa-miR528 | 2 | 21 | 6 | bdi-miR528 | 36 | 21 | 1 | 283 |
| osa-miR528 | 2 | 21 | 6 | mtr-miR528 | 37 | 21 | 0.86 | 284 |
| osa-miR528 | 2 | 21 | 6 | sbi-miR528 | 38 | 21 | 1 | 285 |
| osa-miR528 | 2 | 21 | 6 | ssp-miR528 | 39 | 21 | 1 | 286 |
| osa-miR528 | 2 | 21 | 6 | zma-miR528a | 40 | 21 | 1 | 287 |
| osa-miR528 | 2 | 21 | 6 | zma-miR528b | 41 | 21 | 1 | 288 |
| sly-miR169d | 3 | 21 | 7 | aly-miR169a | 42 | 21 | 0.9 | 289 |
| sly-miR169d | 3 | 21 | 7 | aly-miR169b | 43 | 21 | 0.86 | 290 |
| sly-miR169d | 3 | 21 | 7 | aly-miR169c | 44 | 21 | 0.86 | 291 |
| sly-miR169d | 3 | 21 | 7 | aly-miR169d | 45 | 21 | 0.86 | 292 |
| sly-miR169d | 3 | 21 | 7 | aly-miR169e | 46 | 21 | 0.86 | 293 |
| sly-miR169d | 3 | 21 | 7 | aly-miR169f | 47 | 21 | 0.86 | 294 |
| sly-miR169d | 3 | 21 | 7 | aly-miR169g | 48 | 21 | 0.86 | 295 |
| sly-miR169d | 3 | 21 | 7 | aly-miR169h | 49 | 21 | 0.95 | 296 |
| sly-miR169d | 3 | 21 | 7 | aly-miR169i | 50 | 21 | 0.95 | 297 |
| sly-miR169d | 3 | 21 | 7 | aly-miR169j | 51 | 21 | 0.95 | 298 |
| sly-miR169d | 3 | 21 | 7 | aly-miR169k | 52 | 21 | 0.95 | 299 |
| sly-miR169d | 3 | 21 | 7 | aly-miR169l | 53 | 21 | 0.95 | 300 |
| sly-miR169d | 3 | 21 | 7 | aly-miR169m | 54 | 21 | 0.95 | 301 |
| sly-miR169d | 3 | 21 | 7 | aly-miR169n | 55 | 21 | 0.9 | 302 |
| sly-miR169d | 3 | 21 | 7 | ama-miR169 | 56 | 20 | 0.9 | 303 |
| sly-miR169d | 3 | 21 | 7 | aqc-miR169a | 57 | 21 | 1 | 304 |
| sly-miR169d | 3 | 21 | 7 | aqc-miR169b | 58 | 21 | 0.95 | 305 |
| sly-miR169d | 3 | 21 | 7 | aqc-miR169c | 59 | 21 | 0.86 | 306 |
| sly-miR169d | 3 | 21 | 7 | ata-miR169 | 60 | 21 | 0.86 | 307 |

TABLE 2-continued

Summary of Homologs/Orthologs of Small RNA Probes of Table 1.

| Small RNA Name | Mature sequence/ SEQ ID No: | Mir Length | Stem-loop sequence/ SEQ ID No: | Homolog Name | Homolog sequence/ SEQ ID No: | Homolog length | % Identity | Homolog Stem-loop Sequence/ SEQ ID No: |
|---|---|---|---|---|---|---|---|---|
| sly-miR169d | 3 | 21 | 7 | ath-miR169a | 61 | 21 | 0.9 | 308 |
| sly-miR169d | 3 | 21 | 7 | ath-miR169b | 62 | 21 | 0.86 | 309 |
| sly-miR169d | 3 | 21 | 7 | ath-miR169c | 63 | 21 | 0.86 | 310 |
| sly-miR169d | 3 | 21 | 7 | ath-miR169d | 64 | 21 | 0.86 | 311 |
| sly-miR169d | 3 | 21 | 7 | ath-miR169e | 65 | 21 | 0.86 | 312 |
| sly-miR169d | 3 | 21 | 7 | ath-miR169f | 66 | 21 | 0.86 | 313 |
| sly-miR169d | 3 | 21 | 7 | ath-miR169g | 67 | 21 | 0.86 | 314 |
| sly-miR169d | 3 | 21 | 7 | ath-miR169h | 68 | 21 | 0.95 | 315 |
| sly-miR169d | 3 | 21 | 7 | ath-miR169i | 69 | 21 | 0.95 | 316 |
| sly-miR169d | 3 | 21 | 7 | ath-miR169j | 70 | 21 | 0.95 | 317 |
| sly-miR169d | 3 | 21 | 7 | ath-miR169k | 71 | 21 | 0.95 | 318 |
| sly-miR169d | 3 | 21 | 7 | ath-miR169l | 72 | 21 | 0.95 | 319 |
| sly-miR169d | 3 | 21 | 7 | ath-miR169m | 73 | 21 | 0.95 | 320 |
| sly-miR169d | 3 | 21 | 7 | ath-miR169n | 74 | 21 | 0.95 | 321 |
| sly-miR169d | 3 | 21 | 7 | bdi-miR169a | 75 | 21 | 0.9 | 322, 528 |
| sly-miR169d | 3 | 21 | 7 | bdi-miR169b | 76 | 21 | 0.9 | 323 |
| sly-miR169d | 3 | 21 | 7 | bdi-miR169c | 77 | 21 | 0.86 | 324 |
| sly-miR169d | 3 | 21 | 7 | bdi-miR169d | 78 | 21 | 0.95 | 325 |
| sly-miR169d | 3 | 21 | 7 | bdi-miR169e | 79 | 21 | 0.95 | 326 |
| sly-miR169d | 3 | 21 | 7 | bdi-miR169f | 80 | 21 | 0.86 | 327 |
| sly-miR169d | 3 | 21 | 7 | bdi-miR169g | 81 | 21 | 0.95 | 328 |
| sly-miR169d | 3 | 21 | 7 | bdi-miR169h | 82 | 21 | 1 | 329 |
| sly-miR169d | 3 | 21 | 7 | bdi-miR169i | 83 | 22 | 0.86 | 330 |
| sly-miR169d | 3 | 21 | 7 | bdi-miR169j | 84 | 21 | 0.86 | 331 |
| sly-miR169d | 3 | 21 | 7 | bdi-miR169k | 85 | 22 | 0.9 | 332 |
| sly-miR169d | 3 | 21 | 7 | bna-miR169a | 86 | 21 | 0.9 | 333 |
| sly-miR169d | 3 | 21 | 7 | bna-miR169b | 87 | 21 | 0.9 | 334 |
| sly-miR169d | 3 | 21 | 7 | bna-miR169c | 88 | 21 | 1 | 335 |
| sly-miR169d | 3 | 21 | 7 | bna-miR169d | 89 | 21 | 1 | 336 |
| sly-miR169d | 3 | 21 | 7 | bna-miR169e | 90 | 21 | 1 | 337, 529 |
| sly-miR169d | 3 | 21 | 7 | bna-miR169f | 91 | 21 | 1 | 338 |
| sly-miR169d | 3 | 21 | 7 | bna-miR169g | 92 | 22 | 0.95 | 339 |
| sly-miR169d | 3 | 21 | 7 | bna-miR169h | 93 | 22 | 0.95 | 340 |
| sly-miR169d | 3 | 21 | 7 | bna-miR169i | 94 | 22 | 0.95 | 341 |
| sly-miR169d | 3 | 21 | 7 | bna-miR169j | 95 | 22 | 0.95 | 342 |
| sly-miR169d | 3 | 21 | 7 | bna-miR169k | 96 | 22 | 0.95 | 343 |
| sly-miR169d | 3 | 21 | 7 | bna-miR169l | 97 | 22 | 0.95 | 344 |
| sly-miR169d | 3 | 21 | 7 | bna-miR169m | 98 | 21 | 0.81 | 345 |
| sly-miR169d | 3 | 21 | 7 | csi-miR169 | 99 | 21 | 0.86 | 346 |
| sly-miR169d | 3 | 21 | 7 | far-miR169 | 100 | 21 | 1 | 347 |
| sly-miR169d | 3 | 21 | 7 | ghb-miR169a | 101 | 21 | 0.95 | 348 |
| sly-miR169d | 3 | 21 | 7 | gma-miR169a | 102 | 21 | 0.86 | 349 |
| sly-miR169d | 3 | 21 | 7 | gma-miR169b | 103 | 21 | 0.9 | 350 |
| sly-miR169d | 3 | 21 | 7 | gma-miR169c | 104 | 21 | 0.9 | 351 |
| sly-miR169d | 3 | 21 | 7 | gma-miR169d | 105 | 23 | 0.86 | 352 |
| sly-miR169d | 3 | 21 | 7 | gma-miR169e | 106 | 20 | 0.86 | 353 |
| sly-miR169d | 3 | 21 | 7 | gma-miR169p | 107 | 21 | 0.86 | 354 |
| sly-miR169d | 3 | 21 | 7 | gso-miR169a | 108 | 21 | 0.86 | 355 |
| sly-miR169d | 3 | 21 | 7 | hvu-miR169 | 109 | 21 | 0.86 | 356 |
| sly-miR169d | 3 | 21 | 7 | mtr-miR169a | 110 | 21 | 0.9 | 357 |
| sly-miR169d | 3 | 21 | 7 | mtr-miR169b | 111 | 21 | 0.9 | 358 |
| sly-miR169d | 3 | 21 | 7 | mtr-miR169c | 112 | 21 | 0.81 | 359, 530 |
| sly-miR169d | 3 | 21 | 7 | mtr-miR169d | 113 | 21 | 0.86 | 360, 531 |
| sly-miR169d | 3 | 21 | 7 | mtr-miR169e | 114 | 21 | 0.86 | 361 |
| sly-miR169d | 3 | 21 | 7 | mtr-miR169f | 115 | 21 | 0.95 | 362 |
| sly-miR169d | 3 | 21 | 7 | mtr-miR169g | 116 | 21 | 0.86 | 363 |
| sly-miR169d | 3 | 21 | 7 | mtr-miR169h | 117 | 21 | 0.81 | 364 |
| sly-miR169d | 3 | 21 | 7 | mtr-miR169i | 118 | 21 | 0.81 | 365 |
| sly-miR169d | 3 | 21 | 7 | mtr-miR169j | 119 | 21 | 0.86 | 366 |
| sly-miR169d | 3 | 21 | 7 | mtr-miR169l | 120 | 21 | 0.86 | 367 |
| sly-miR169d | 3 | 21 | 7 | mtr-miR169m | 121 | 21 | 0.86 | 368 |
| sly-miR169d | 3 | 21 | 7 | mtr-miR169n | 122 | 21 | 0.81 | 369 |
| sly-miR169d | 3 | 21 | 7 | mtr-miR169o | 123 | 21 | 0.81 | 370 |
| sly-miR169d | 3 | 21 | 7 | osa-miR169c | 124 | 21 | 0.86 | 371 |
| sly-miR169d | 3 | 21 | 7 | osa-miR169d | 125 | 21 | 0.86 | 372 |
| sly-miR169d | 3 | 21 | 7 | osa-miR169e | 126 | 21 | 0.9 | 373 |
| sly-miR169d | 3 | 21 | 7 | osa-miR169f | 127 | 21 | 1 | 374 |
| sly-miR169d | 3 | 21 | 7 | osa-miR169g | 128 | 21 | 1 | 375 |
| sly-miR169d | 3 | 21 | 7 | osa-miR169h | 129 | 21 | 0.95 | 376 |
| sly-miR169d | 3 | 21 | 7 | osa-miR169i | 130 | 21 | 0.95 | 377 |
| sly-miR169d | 3 | 21 | 7 | osa-miR169j | 131 | 21 | 0.95 | 378 |
| sly-miR169d | 3 | 21 | 7 | osa-miR169k | 132 | 21 | 0.95 | 379 |

TABLE 2-continued

Summary of Homologs/Orthologs of Small RNA Probes of Table 1.

| Small RNA Name | Mature sequence/ SEQ ID No: | Mir Length | Stem-loop sequence/ SEQ ID No: | Homolog Name | Homolog sequence/ SEQ ID No: | Homolog length | % Identity | Homolog Stem-loop Sequence/ SEQ ID No: |
|---|---|---|---|---|---|---|---|---|
| sly-miR169d | 3 | 21 | 7 | osa-miR169l | 133 | 21 | 0.95 | 380 |
| sly-miR169d | 3 | 21 | 7 | osa-miR169m | 134 | 21 | 0.95 | 381 |
| sly-miR169d | 3 | 21 | 7 | osa-miR169n | 135 | 21 | 0.95 | 382 |
| sly-miR169d | 3 | 21 | 7 | osa-miR169o | 136 | 21 | 0.95 | 383 |
| sly-miR169d | 3 | 21 | 7 | osa-miR169p | 137 | 22 | 0.81 | 384 |
| sly-miR169d | 3 | 21 | 7 | osa-miR169q | 138 | 21 | 0.86 | 385 |
| sly-miR169d | 3 | 21 | 7 | phy-miR169 | 139 | 21 | 0.86 | 386 |
| sly-miR169d | 3 | 21 | 7 | ptc-miR169a | 140 | 21 | 0.9 | 387 |
| sly-miR169d | 3 | 21 | 7 | ptc-miR169ab | 141 | 21 | 0.9 | 388 |
| sly-miR169d | 3 | 21 | 7 | ptc-miR169ac | 142 | 21 | 0.9 | 389 |
| sly-miR169d | 3 | 21 | 7 | ptc-miR169ad | 143 | 21 | 0.9 | 390 |
| sly-miR169d | 3 | 21 | 7 | ptc-miR169ae | 144 | 21 | 0.9 | 391 |
| sly-miR169d | 3 | 21 | 7 | ptc-miR169af | 145 | 21 | 0.9 | 392 |
| sly-miR169d | 3 | 21 | 7 | ptc-miR169b | 146 | 21 | 0.9 | 393 |
| sly-miR169d | 3 | 21 | 7 | ptc-miR169c | 147 | 21 | 0.9 | 394 |
| sly-miR169d | 3 | 21 | 7 | ptc-miR169d | 148 | 21 | 0.86 | 395 |
| sly-miR169d | 3 | 21 | 7 | ptc-miR169e | 149 | 21 | 0.86 | 396 |
| sly-miR169d | 3 | 21 | 7 | ptc-miR169f | 150 | 21 | 0.86 | 397 |
| sly-miR169d | 3 | 21 | 7 | ptc-miR169g | 151 | 21 | 0.86 | 398 |
| sly-miR169d | 3 | 21 | 7 | ptc-miR169h | 152 | 21 | 0.86 | 399 |
| sly-miR169d | 3 | 21 | 7 | ptc-miR169i | 153 | 21 | 0.95 | 400 |
| sly-miR169d | 3 | 21 | 7 | ptc-miR169j | 154 | 21 | 0.95 | 401 |
| sly-miR169d | 3 | 21 | 7 | ptc-miR169k | 155 | 21 | 0.95 | 402 |
| sly-miR169d | 3 | 21 | 7 | ptc-miR169l | 156 | 21 | 0.95 | 403 |
| sly-miR169d | 3 | 21 | 7 | ptc-miR169m | 157 | 21 | 0.95 | 404 |
| sly-miR169d | 3 | 21 | 7 | ptc-miR169n | 158 | 21 | 0.86 | 405 |
| sly-miR169d | 3 | 21 | 7 | ptc-miR169o | 159 | 21 | 0.9 | 406 |
| sly-miR169d | 3 | 21 | 7 | ptc-miR169p | 160 | 21 | 0.9 | 407 |
| sly-miR169d | 3 | 21 | 7 | ptc-miR169q | 161 | 21 | 0.9 | 408 |
| sly-miR169d | 3 | 21 | 7 | ptc-miR169r | 162 | 21 | 1 | 409 |
| sly-miR169d | 3 | 21 | 7 | ptc-miR169s | 163 | 21 | 0.86 | 410 |
| sly-miR169d | 3 | 21 | 7 | ptc-miR169t | 164 | 21 | 0.81 | 411 |
| sly-miR169d | 3 | 21 | 7 | ptc-miR169u | 165 | 21 | 0.95 | 412 |
| sly-miR169d | 3 | 21 | 7 | ptc-miR169v | 166 | 21 | 0.95 | 413 |
| sly-miR169d | 3 | 21 | 7 | ptc-miR169w | 167 | 21 | 0.95 | 414 |
| sly-miR169d | 3 | 21 | 7 | ptc-miR169x | 168 | 21 | 0.86 | 415 |
| sly-miR169d | 3 | 21 | 7 | ptc-miR169y | 169 | 21 | 0.86 | 416 |
| sly-miR169d | 3 | 21 | 7 | ptc-miR169z | 170 | 21 | 0.76 | 417 |
| sly-miR169d | 3 | 21 | 7 | ptr-miR169a | 171 | 21 | 0.9 | 418 |
| sly-miR169d | 3 | 21 | 7 | ptr-miR169b | 172 | 21 | 0.86 | 419 |
| sly-miR169d | 3 | 21 | 7 | rco-miR169a | 173 | 21 | 0.86 | 420 |
| sly-miR169d | 3 | 21 | 7 | rco-miR169b | 174 | 21 | 0.86 | 421 |
| sly-miR169d | 3 | 21 | 7 | rco-miR169c | 175 | 21 | 0.86 | 422 |
| sly-miR169d | 3 | 21 | 7 | sbi-miR169a | 176 | 21 | 0.9 | 423, 532 |
| sly-miR169d | 3 | 21 | 7 | sbi-miR169b | 177 | 21 | 0.86 | 424 |
| sly-miR169d | 3 | 21 | 7 | sbi-miR169c | 178 | 21 | 1 | 425 |
| sly-miR169d | 3 | 21 | 7 | sbi-miR169d | 179 | 21 | 1 | 426, 533 |
| sly-miR169d | 3 | 21 | 7 | sbi-miR169e | 180 | 21 | 0.95 | 427, 534 |
| sly-miR169d | 3 | 21 | 7 | sbi-miR169f | 181 | 21 | 0.95 | 428 |
| sly-miR169d | 3 | 21 | 7 | sbi-miR169g | 182 | 21 | 0.95 | 429 |
| sly-miR169d | 3 | 21 | 7 | sbi-miR169h | 183 | 21 | 1.00 | 430, 535 |
| sly-miR169d | 3 | 21 | 7 | sbi-miR169i | 184 | 21 | 0.95 | 431 |
| sly-miR169d | 3 | 21 | 7 | sbi-miR169j | 185 | 21 | 0.9 | 432 |
| sly-miR169d | 3 | 21 | 7 | sbi-miR169k | 186 | 21 | 0.86 | 433 |
| sly-miR169d | 3 | 21 | 7 | sbi-miR169l | 187 | 21 | 0.95 | 434, 536 |
| sly-miR169d | 3 | 21 | 7 | sbi-miR169m | 188 | 21 | 1 | 435 |
| sly-miR169d | 3 | 21 | 7 | sbi-miR169n | 189 | 21 | 1 | 436 |
| sly-miR169d | 3 | 21 | 7 | sbi-miR169o | 190 | 21 | 0.9 | 437 |
| sly-miR169d | 3 | 21 | 7 | sbi-miR169p | 191 | 21 | 0.9 | 438 |
| sly-miR169d | 3 | 21 | 7 | sbi-miR169q | 192 | 21 | 0.9 | 439 |
| sly-miR169d | 3 | 21 | 7 | sly-miR169a | 193 | 21 | 0.86 | 440 |
| sly-miR169d | 3 | 21 | 7 | sly-miR169b | 194 | 21 | 0.95 | 441 |
| sly-miR169d | 3 | 21 | 7 | sly-miR169c | 195 | 21 | 0.9 | 442 |
| sly-miR169d | 3 | 21 | 7 | sof-miR169 | 196 | 21 | 0.9 | 443 |
| sly-miR169d | 3 | 21 | 7 | ssp-miR169 | 197 | 21 | 0.9 | 444 |
| sly-miR169d | 3 | 21 | 7 | tcc-miR169a | 198 | 21 | 0.9 | 445 |
| sly-miR169d | 3 | 21 | 7 | tcc-miR169b | 199 | 21 | 0.86 | 446 |
| sly-miR169d | 3 | 21 | 7 | tcc-miR169c | 200 | 21 | 0.9 | 447 |
| sly-miR169d | 3 | 21 | 7 | tcc-miR169d | 201 | 21 | 1 | 448 |
| sly-miR169d | 3 | 21 | 7 | tcc-miR169e | 202 | 21 | 0.9 | 449 |
| sly-miR169d | 3 | 21 | 7 | tcc-miR169f | 203 | 21 | 0.86 | 450 |
| sly-miR169d | 3 | 21 | 7 | tcc-miR169g | 204 | 21 | 0.95 | 451 |

TABLE 2-continued

Summary of Homologs/Orthologs of Small RNA Probes of Table 1.

| Small RNA Name | Mature sequence/ SEQ ID No: | Mir Length | Stem-loop sequence/ SEQ ID No: | Homolog Name | Homolog sequence/ SEQ ID No: | Homolog length | % Identity | Homolog Stem-loop Sequence/ SEQ ID No: |
|---|---|---|---|---|---|---|---|---|
| sly-miR169d | 3 | 21 | 7 | tcc-miR169h | 205 | 21 | 0.95 | 452 |
| sly-miR169d | 3 | 21 | 7 | tcc-miR169i | 206 | 21 | 0.9 | 453 |
| sly-miR169d | 3 | 21 | 7 | tcc-miR169j | 207 | 21 | 0.95 | 454 |
| sly-miR169d | 3 | 21 | 7 | tcc-miR169k | 208 | 21 | 0.86 | 455 |
| sly-miR169d | 3 | 21 | 7 | tcc-miR169l | 209 | 21 | 0.86 | 456 |
| sly-miR169d | 3 | 21 | 7 | tcc-miR169m | 210 | 21 | 0.86 | 457 |
| sly-miR169d | 3 | 21 | 7 | vvi-miR169a | 211 | 21 | 0.86 | 458 |
| sly-miR169d | 3 | 21 | 7 | vvi-miR169b | 212 | 21 | 0.81 | 459 |
| sly-miR169d | 3 | 21 | 7 | vvi-miR169c | 213 | 21 | 0.86 | 460 |
| sly-miR169d | 3 | 21 | 7 | vvi-miR169e | 214 | 22 | 0.95 | 461 |
| sly-miR169d | 3 | 21 | 7 | vvi-miR169f | 215 | 21 | 0.9 | 462 |
| sly-miR169d | 3 | 21 | 7 | vvi-miR169g | 216 | 21 | 0.9 | 463 |
| sly-miR169d | 3 | 21 | 7 | vvi-miR169h | 217 | 21 | 0.81 | 464 |
| sly-miR169d | 3 | 21 | 7 | vvi-miR169i | 218 | 21 | 0.81 | 465 |
| sly-miR169d | 3 | 21 | 7 | vvi-miR169j | 219 | 21 | 0.86 | 466 |
| sly-miR169d | 3 | 21 | 7 | vvi-miR169k | 220 | 21 | 0.86 | 467 |
| sly-miR169d | 3 | 21 | 7 | vvi-miR169l | 221 | 21 | 0.86 | 468 |
| sly-miR169d | 3 | 21 | 7 | vvi-miR169m | 222 | 21 | 0.86 | 469 |
| sly-miR169d | 3 | 21 | 7 | vvi-miR169n | 223 | 21 | 0.86 | 470 |
| sly-miR169d | 3 | 21 | 7 | vvi-miR169o | 224 | 21 | 0.86 | 471 |
| sly-miR169d | 3 | 21 | 7 | vvi-miR169p | 225 | 21 | 0.86 | 472 |
| sly-miR169d | 3 | 21 | 7 | vvi-miR169q | 226 | 21 | 0.86 | 473 |
| sly-miR169d | 3 | 21 | 7 | vvi-miR169r | 227 | 21 | 0.81 | 474 |
| sly-miR169d | 3 | 21 | 7 | vvi-miR169s | 228 | 21 | 0.86 | 475 |
| sly-miR169d | 3 | 21 | 7 | vvi-miR169t | 229 | 21 | 0.81 | 476 |
| sly-miR169d | 3 | 21 | 7 | vvi-miR169u | 230 | 21 | 0.81 | 477 |
| sly-miR169d | 3 | 21 | 7 | vvi-miR169v | 231 | 21 | 0.81 | 478 |
| sly-miR169d | 3 | 21 | 7 | vvi-miR169w | 232 | 21 | 0.86 | 479 |
| sly-miR169d | 3 | 21 | 7 | vvi-miR169x | 233 | 21 | 1 | 480 |
| sly-miR169d | 3 | 21 | 7 | vvi-miR169y | 234 | 21 | 0.95 | 481 |
| sly-miR169d | 3 | 21 | 7 | zma-miR169a | 235 | 21 | 0.9 | 482 |
| sly-miR169d | 3 | 21 | 7 | zma-miR169b | 236 | 21 | 0.9 | 483 |
| sly-miR169d | 3 | 21 | 7 | zma-miR169c | 237 | 21 | 0.86 | 484 |
| sly-miR169d | 3 | 21 | 7 | zma-miR169d | 238 | 21 | 0.9 | 485 |
| sly-miR169d | 3 | 21 | 7 | zma-miR169e | 239 | 21 | 0.9 | 486 |
| sly-miR169d | 3 | 21 | 7 | zma-miR169f | 240 | 21 | 1 | 487 |
| sly-miR169d | 3 | 21 | 7 | zma-miR169g | 241 | 21 | 1 | 488 |
| sly-miR169d | 3 | 21 | 7 | zma-miR169h | 242 | 21 | 1 | 489 |
| sly-miR169d | 3 | 21 | 7 | zma-miR169i | 243 | 21 | 0.95 | 490 |
| sly-miR169d | 3 | 21 | 7 | zma-miR169j | 244 | 21 | 0.95 | 491 |
| sly-miR169d | 3 | 21 | 7 | zma-miR169k | 245 | 21 | 0.95 | 492 |
| sly-miR169d | 3 | 21 | 7 | zma-miR169l | 246 | 21 | 1.00 | 493, 537 |
| sly-miR169d | 3 | 21 | 7 | zma-miR169m | 247 | 21 | 1.00 | 494, 538 |
| sly-miR169d | 3 | 21 | 7 | zma-miR169n | 248 | 21 | 0.9 | 495, 539 |
| sly-miR169d | 3 | 21 | 7 | zma-miR169o | 249 | 21 | 0.95 | 496, 540 |
| sly-miR169d | 3 | 21 | 7 | zma-miR169p | 250 | 21 | 0.9 | 497, 541 |
| sly-miR169d | 3 | 21 | 7 | zma-miR169q | 251 | 21 | 0.9 | 498, 542 |
| sly-miR169d | 3 | 21 | 7 | zma-miR169r | 252 | 21 | 0.86 | 499, 543 |
| sly-miR169d | 3 | 21 | 7 | zma-miR169s | 253 | 21 | 0.9 | 500 |
| sly-miR169d | 3 | 21 | 7 | zma-miR169t | 254 | 21 | 0.9 | 501 |
| sly-miR169d | 3 | 21 | 7 | zma-miR169u | 255 | 21 | 0.9 | 502 |
| smo-miR1110 | 4 | 21 | 8 | NA | NA | NA | NA | NA |

Example 3

Identification of miRNAs Associated with Increased Sugar Content and Target Prediction Using Bioinformatics Tools Small RNAs that are potentially associated with improved sugar content can be identified by proprietary computational algorithms that analyze RNA expression profiles alongside publicly available gene and protein databases. A high throughput screening is performed on microarrays loaded with miRNAs that were found to be differential under multiple stress and optimal environmental conditions and in different plant tissues. The initial trait-associated miRNAs are later validated by quantitative Real Time PCR (qRT-PCR).

Target prediction homologous or orthologous genes to the genes of interest in tomato are found through a proprietary tool that analyzes publicly available genomic as well as expression and gene annotation databases from multiple plant species. Homologous and orthologous protein and nucleotide sequences of target genes of the small RNA sequences of the invention, were found using BLAST having at least 70% identity on at least 60% of the entire master gene length, and are summarized in Table 3 below.

TABLE 3

Target Genes of Small RNA Molecules Associated with Increased Sugar Content in Tomato Plants.

| Mir name | Mir sequence SEQ ID NO | Mir Binding Position | HomologNCBI Accession | Organism | Protein Sequence SEQ ID NO | Nucleotide Sequence SEQ ID NO |
|---|---|---|---|---|---|---|
| bna-miR397a | 1 | 338-359 | AAM92008 | Solanum tuberosum | 503 | 513 |
| bna-miR397a | 1 | | ABB72804 | Solanum tuberosum | 504 | 514 |
| bna-miR397a | 1 | | ABV02033 | Nicotiana langsdorffii × Nicotiana sanderae | 505 | 515 |
| bna-miR397a | 1 | | BAJ33926 | Thellungiella halophila | 506 | 516 |
| bna-miR397a | 1 | | NP_172801 | Arabidopsis thaliana | 507 | 517 |
| bna-miR397a | 1 | | XP_002892749 | Arabidopsis lyrata subsp. lyrata | 508 | 518 |
| bna-miR397a | 1 | | CAB39974 | Nicotiana tabacum | 509 | 519 |
| bna-miR397a | 1 | | BAH20011 | Arabidopsis thaliana | 510 | 520 |
| bna-miR397a | 1 | | P09094 | Nicotiana tabacum | 511 | |
| bna-miR397a | 1 | | P04796 | Sinapis alba | 512 | |

Example 4

Verification of Expression of Small RNA Molecules Associated with Increased Sugar Content in Tomato Plants Following identification of small RNA molecules potentially involved in improvement of sugar content in tomato plants using bioinformatics tools, as described in Example 3 above, the actual mRNA levels in an experiment are determined using reverse transcription assay followed by quantitative Real-Time PCR (qRT-PCR) analysis. RNA levels are compared between different tissues, developmental stages, growing conditions and/or genetic backgrounds incorporated in each experiment. A correlation analysis between mRNA levels in different experimental conditions/genetic backgrounds is applied and used as evidence for the role of the gene in the plant.

Methods

Leaf samples are freshly excised from tomato plants grown as described above. Total RNA is extracted using mirVana™ commercial kit (Ambion) following the protocol provided by the manufacturer. For measurement and verification of messenger RNA (mRNA) expression level of all genes, reverse transcription followed by quantitative real time PCR (qRT-PCR) is performed on total RNA extracted from leaves. To elaborate, reverse transcription is performed on 1 µg total RNA, using a miScript Reverse Transcriptase kit (Qiagen), following the protocol suggested by the manufacturer. Quantitative RT-PCR is performed on cDNA (0.1 ng/µl final concentration), using a miScript SYBR GREEN PCR (Qiagen) forward (based on the miR sequence itself) and reverse primers (supplied with the kit). All qRT-PCR reactions are performed in triplicates using an ABI7500 real-time PCR machine, following the recommended protocol for the machine. To normalize the expression level of miRNAs associated with enhanced abiotic stress tolerance between the different tissues and growing conditions of the soybean plants, normalizer miRNAs are selected and used for comparison. Normalizer miRNAs, which are miRNAs with unchanged expression level between tissues and growing conditions, are custom selected for each experiment. The normalization procedure consists of second-degree polynomial fitting to a reference data (which is the median vector of all the data—excluding outliers) as described by Rosenfeld et al (2008, Nat Biotechnol, 26(4):462-469). A summary of primers for the differential small RNA molecules that will be used in the qRT-PCR validation and analysis is presented in Table 4 below.

TABLE 4

Primers for qRT-PCR Analysis of Small RNA Molecules Differentially Expressed under Drought Stress.

| Mir Name | Mir Sequence/ SEQ ID No. | Primer Sequence/ SEQ ID No. | Primer Length |
|---|---|---|---|
| Osa-miR528 | 2 | 521 | 21 |
| Sly-miR169d | 3 | 522 | 24 |

Example 5

Method for Generating Transgenic Plants with Manipulated Expression of microRNAs Synthetic DNA fragments that contain the pre-miR sequences of selected microRNAs can be synthesized and cloned into an expression vector suitable for genetic transformation of plants. Examples for such vectors are pORE-E2 (Accession number: AY562535), vectors of the pCAMBIA series that can be obtained from Cambia (wwwdotcambiadotorg/daisy/cambia/homedothtml), pROK2, and others.

The resulting vectors can be transformed by electroporation into *Agrobacterium tumefaciens* strain GV3101. Single colonies can be grown and used to transform plants. To test the effect of a microRNA on the sugar content of tomato fruit, tomato plants can be genetically transformed so that the expression of a specific microRNA is manipulated. Genetic transformation of tomato can be achieved by a method such as the one described in (Cortina. C and Culiáñez-Macià, F A, Plant Cell, Tissue and Organ Culture Volume 76, Number 3). Using this method, transgenic plants are typically ready to be planted in soil after about two months. Transgenic plants are analyzed by PCR to validate integration of the transgene into the genome and by quantitative RT-PCR to validate over-expression of the relevant mature microRNA.

5.1. Method for Generating Transgenic Plants with Reduced microRNA Regulation

Target prediction enables manipulation of microRNA regulation by introducing silent mutations into the microRNA-binding site, leading to the expression of a microRNA-resistant target, thereby bypassing microRNA regulation. Alternatively, manipulation of microRNA regulation can be performed by microRNA over-expression. Both these strategies have been used in plants and have resulted in significant phenotype alterations.

Reducing microRNA regulation of target genes can potentially be achieved by two methods, either by expressing a microRNA-resistant gene or by expressing a target-mimic sequence.

(a) Expressing a microRNA-Resistant Target

In this method, silent mutations are introduced in the microRNA binding site of the target gene so that the DNA and resulting RNA sequences are changed in a way that prevents microRNA binding, but the amino acid sequence of the protein is unchanged.

(b) Expressing a Target-Mimic Sequence

Plant microRNAs usually lead to cleavage of their targeted gene, with this cleavage typically occurring between bases 10 and 11 of the microRNA. This position is therefore especially sensitive to mismatches between the microRNA and the target. It was found that expressing a DNA sequence that could potentially be targeted by a microRNA, but contains two extra nucleotides between the two nucleotides that are predicted to hybridize with bases 10-11 of the microRNA (thus creating a bulge in that position), can inhibit the regulation of that microRNA on its native targets.

This type of sequence is referred to as a "target-mimic". Inhibition of the microRNA regulation is presumed to occur through physically capturing the microRNA by the target-mimic sequence and titering-out the microRNA, thereby reducing its abundance. This method was used to reduce the amount and, consequentially, the regulation of microRNA 399 in *Arabidopsis* (Franco-Zorilla J M et al., Nature Genetics 2007; 39(8):1033-1037).

TABLE 5 miRNA-Resistant Target Examples for Selected miRNAs which were Downregulated in Cultivated Tomato Variety.

| Mir name | Mir sequence/ SEQ ID No. | Bulge Reverse Complement miR/ SEQ ID No. | Bulge in Target Binding Sequence/ SEQ ID No. | Full Target Mimic Nucleotide Sequence/ SEQ ID No. |
|---|---|---|---|---|
| bna-miR397a | 1 | 523 | 524 | 525 |

TABLE 6

Abbreviations of Plant Species

| Abbreviation | Organism Full Name | Common Name |
|---|---|---|
| aly | *Arabidopsis lyrata* | *Arabidopsis lyrata* |
| aqc | *Aquilegia coerulea* | Rocky Mountain Columbine |
| ama | *Antirrhinum majus* | |
| ata | *Aegilops tauschii* | Tausch's goatgrass |
| ath | *Arabidopsis thaliana* | *Arabidopsis thaliana* |
| bdi | *Brachypodium distachyon* | Grass |
| bna | *Brassica napus* | *Brassica napus* canola ("liftit") |
| csi | *Citrus sinensis* | Orange |
| far | *Festuca arundinacea* | Tall fescue |
| ghb | *Gossypium herbaceum* | *Gossypium herbecium* levant cotton |
| ghr | *Gossypium hirsutum* | *Gossypium hirsutum* cotton |
| gma | *Glycine max* | *Glycine max* |
| gso | *Glycine soja* | Wild soybean |
| hvu | *Hordeum vulgare* | Barley |
| mtr | *Medicago truncatula* | *Medicago truncatula* - Barrel Clover ("tiltan") |
| osa | *Oryza sativa* | *Oryza sativa* |
| pab | *Picea abies* | European spruce |
| phy | *Petunia* x *hybrida* | garden petunia |
| ptc | *Populus trichocarpa* | *Populus trichocarpa* - black cotton wood |
| ptr | *Phaeodactylum tricornutum* | *Phaeodactylum tricornutum* |
| rco | *Ricinus communis* | Castor Bean |
| sbi | *Sorghum bicolor* | *Sorghum bicolor* Dura |
| sly | *Solanum lycopersicum* | *Solanum lycopersicum* tomato |
| smo | *Selaginella moellendorffii* | *Selaginella moellendorffii* |
| sof | *Saccharum officinarum* | Sugarcane |
| ssp | *Saccharum* spp. | Sugarcane |
| tcc | *Theobroma cacao* | cacao tree |
| vvi | *Vitis vinifera* | *Vitis vinifera* Grapes |
| zma | *Zea mays* | corn |

Example 6

Testing for Changes in Tomato Fruit Sugar Content

The following procedure can be carried out for soluble sugar determination. Fruit portions of about 500 mg fresh weight are placed in 80% ethanol and soluble sugars are extracted from the tissue by heating to 70° C., as described in Miron and Schaffer (Plant Physiol. 1991 February; 95(2): 623-7). Sugars can be chromatographically separated by HPLC for example using a Bio-Rad Fast Carbohydrate column according to manufacturer's directions. Sucrose, glucose, and fructose can be identified by their retention times and quantified in comparison to sugar standards.

What is claimed is:

1. A method of increasing the sucrose level or increasing the sucrose to glucose ratio in a tomato plant comprising expressing in said tomato plant
a DNA encoding a miR397-, miR528-, or miR1110-resistant target gene, wherein said miR397-, miR528-, or miR1110-resistant target gene comprises an introduced silent mutation in a nucleotide sequence that is otherwise substantially identical to the nucleotide sequence of an endogenous gene that is natively regulated by miR397, miR528, or miR1110, and wherein said silent mutation prevents binding by a mature miR397, miR528, or miR1110 to a transcript of said miR397-, miR528-, or miR1110-resistant target gene, wherein the sucrose level or the sucrose-to-glucose ratio is increased in said tomato plant.

2. The method of claim 1, wherein said at least one DNA comprises a miR397-resistant target gene encoding an amino acid sequence having at least 90% sequence identity to a sequence selected from the group consisting of SEQ ID NOs: 503-512.

3. The method of claim 1, wherein said method achieves a tomato fruit comprising more than 0.5%, more than 0.75%, more than 1%, more than 1.5%, more than 2%, more than 2.5%, more than 3%, more than 3.5%, or more than 4% sucrose by fresh weight.

4. The method of claim 1, wherein the heterologous promoter is a constitutive promoter or an inducible promoter.

5. The method of claim 1, wherein the heterologous promoter is a CaMV 35S promoter or a tomato fruit specific promoter.

6. A method of modifying the carbohydrate content in an edible plant comprising expressing in said edible plant at least one DNA selected from the group consisting of
   a DNA encoding a miR397-, miR528-, or miR1110-resistant target gene, wherein said miR169-, miR397-, miR528-, or miR1110-resistant target gene comprises an introduced silent mutation in a nucleotide sequence that is otherwise substantially identical to the nucleotide sequence of an endogenous gene that is natively regulated by miR169, miR397, miR528, or miR1110, and wherein said silent mutation prevents binding by a mature miR169, miR397, miR528, or miR1110 to a transcript of said miR169-, miR397-, miR528-, or miR1110-resistant target gene,
   wherein the carbohydrate content of said edible plant is modified.

7. The method of claim 6, wherein said at least one DNA comprises a miR397-resistant target gene encoding an amino acid sequence having at least 90% sequence identity to a sequence selected from the group consisting of SEQ ID NOs: 503-512.

8. The method of claim 6, wherein said edible plant comprises more than 0.5%, more than 0.75%, more than 1%, more than 1.5%, more than 2%, more than 2.5%, more than 3%, more than 3.5%, or more than 4% sucrose in a fruit by fresh weight.

* * * * *